(12) United States Patent
Callahan et al.

(10) Patent No.: US 6,825,188 B2
(45) Date of Patent: Nov. 30, 2004

(54) VITRONECTIN RECEPTOR ANTAGONISTS

(75) Inventors: James Francis Callahan, Philadelphia, PA (US); Russell Donovan Cousins, Oxford, PA (US); Richard McCulloch Keenan, Malvern, PA (US); Chet Kwon, King of Prussia, PA (US); William Henry Miller, Schwenksville, PA (US); Irene Nijole Uzinskas, Villanova, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/691,241

(22) Filed: Oct. 22, 2003

(65) Prior Publication Data

US 2004/0082559 A1 Apr. 29, 2004

Related U.S. Application Data

(63) Continuation of application No. 10/320,084, filed on Dec. 16, 2002, now abandoned, which is a continuation of application No. 09/973,973, filed on Oct. 9, 2001, now abandoned, which is a continuation of application No. 09/668,962, filed on Sep. 25, 2000, now abandoned, which is a continuation of application No. 09/269,824, filed as application No. PCT/US97/18001 on Oct. 1, 1997, now abandoned.

(60) Provisional application No. 60/043,776, filed on Apr. 11, 1997, and provisional application No. 60/027,320, filed on Oct. 2, 1996.

(51) Int. Cl.$^7$ ...................... A61K 31/44; C07D 223/16; C07D 243/14; C07D 401/12
(52) U.S. Cl. .................. 514/212.07; 540/531
(58) Field of Search ...................... 540/531; 514/212.07

(56) References Cited

U.S. PATENT DOCUMENTS

| | | | |
|---|---|---|---|
| 4,410,520 A | 10/1983 | Watthey | 424/244 |
| 4,604,389 A | 8/1986 | Ruffen et al. | 514/213 |
| 4,737,495 A | 4/1988 | Bomhard et al. | 514/213 |
| 5,017,571 A | 5/1991 | Hansen et al. | 514/213 |
| 5,403,836 A | 4/1995 | Blackburn et al. | 514/213 |
| 5,565,449 A | 10/1996 | Blackburn et al. | 514/219 |
| 5,663,166 A | 9/1997 | Blackburn et al. | 514/213 |
| 5,674,863 A | 10/1997 | Blackburn et al. | 514/211 |
| 5,674,865 A | 10/1997 | Blackburn et al. | 514/213 |
| 5,693,636 A | 12/1997 | Bondinell | 514/214 |
| 5,939,412 A | 8/1999 | Bondinell et al. | |

FOREIGN PATENT DOCUMENTS

| | | |
|---|---|---|
| WO | WO 92/07568 | 5/1992 |
| WO | WO 93/00095 | 1/1993 |
| WO | WO 93/08174 | 4/1993 |
| WO | WO 94/14776 | 7/1994 |
| WO | WO 95/04057 | 2/1995 |
| WO | WO 09/00730 | 1/1996 |
| WO | WO 96/00574 | 1/1996 |
| WO | WO 96/06087 | 2/1996 |
| WO | WO 96/26190 | 8/1996 |
| WO | WO 97/01540 | 1/1997 |
| WO | WO 97/24119 | 7/1997 |
| WO | WO 97/24122 | 7/1997 |
| WO | WO 97/24124 | 7/1997 |

OTHER PUBLICATIONS

Bondinell, et al., Bio & Med. Chem; 1994, vol. 2, No. 9, pp. 897–908.
Miller, et al., Tetra. Letters; 1995, vol. 36, No. 3, pp. 373–376.
Ku, et al., J. of Med. Chem; 1995, vol. 38, No. 1, pp. 10–11.
Ku, et al., J. of Am. Chem. Society; 1993, vol. 115, No. 19, pp. 8861–8862.

Primary Examiner—Richard L. Raymond
Assistant Examiner—Hong Liu
(74) Attorney, Agent, or Firm—Grace C. Hsu; Mary E. McCarthy; Charles M. Kinzig

(57) ABSTRACT

Compounds having a benzodiazepinyl core structure are disclosed which are vitronectin receptor antagonists useful in the treatment of osteoporosis, angiogenesis, tumor growth and metastasis, atherosclerosis, restenosis and inflammation.

3 Claims, No Drawings

VITRONECTIN RECEPTOR ANTAGONISTS

This is a continuation of application Ser. No. 10/320,084 filed Dec. 16, 2002 now abandoned, which is a continuation of application Ser. No. 09/973,973 filed Oct. 9, 2001, now abandoned, which is a continuation of application Ser. No. 09/668,962 filed Sep. 25, 2000, now abandoned, which is a continuation of application Ser. No. 09/269,824, filed Apr. 1, 1999, now abandoned, which is a 371 of International Application No. PCT/US97/18001, filed Oct. 1, 1997, which claims priority to U.S. Provisional Application Nos: 60/043,776, filed Apr. 11, 1997, and 60/027,320, filed Oct. 2, 1996.

FIELD OF THE INVENTION

This invention relates to pharmaceutically active compounds which inhibit the vitronectin receptor and are useful for the treatment of inflammation, cancer and cardiovascular disorders, such as atherosclerosis and restenosis, and diseases wherein bone resorption is a factor, such as osteoporosis.

BACKGROUND OF THE INVENTION

Integrins are a superfamily of cell adhesion receptors, which are transmembrane glycoproteins expressed on a variety of cells. These cell surface adhesion receptors include gpIIb/IIIa (the fibrinogen receptor) and $\alpha_v\beta_3$ (the vitronectin receptor). The fibrinogen receptor gpIIb/IIIa is expressed on the platelet surface, and mediates platelet aggregation and the formation of a hemostatic clot at the site of a bleeding wound. Philips, et al., *Blood.*, 1988, 71, 831. The vitronectin receptor $\alpha_v\beta_3$ is expressed on a number of cells, including endothelial, smooth muscle, osteoclast, and tumor cells, and, thus, it has a variety of functions. The $\alpha_v\beta_3$ receptor expressed on the membrane of osteoclast cells mediates the adhesion of osteoclasts to the bone matrix, a key step in the bone resorption process. Ross, et al., *J. Biol. Chem.*, 1987, 262, 7703. A disease characterized by excessive bone resorption is osteoporosis. The $\alpha_v\beta_3$ receptor expressed on human aortic smooth muscle cells mediates their migration into neointima, a process which can lead to restenosis after percutaneous coronary angioplasty. Brown, et al., *Cardiovascular Res.*, 1994, 28, 1815. Additionally, Brooks, et al., *Cell*, 1994, 79, 1157 has shown that an $\alpha_v\beta_3$ antagonist is able to promote tumor regression by inducing apoptosis of angiogenic blood vessels. Thus, agents that block the vitronectin receptor would be useful in treating diseases, such as osteoporosis, restenosis and cancer.

The vitronectin receptor is now known to refer to three different integrins, designated $\alpha_v\beta_1$, $\alpha_v\beta_3$ and $\alpha_v\beta_5$. Horton, et al., *Int. J. Exp. Pathol.*, 1990, 71, 741. $\alpha_v\beta_1$ binds fibronectin and vitronectin. $\alpha_v\beta_3$ binds a large variety of ligands, including fibrin, fibrinogen, laminin, thrombospondin, vitronectin, von Willebrand's factor, osteopontin and bone sialoprotein I. $\alpha_v\beta_5$ binds vitronectin. The vitronectin receptor $\alpha_v\beta_5$ has been shown to be involved in cell adhesion of a variety of cell types, including microvascular endothelial cells, (Davis, et al., *J. Cell. Biol.*, 1993, 51, 206), and its role in angiogenesis has been confirmed. Brooks, et al., *Science*, 1994, 264, 569. This integrin is expressed on blood vessels in human wound granulation tissue, but not in normal skin.

The vitronectin receptor is known to bind to bone matrix proteins which contain the tri-peptide Arg-Gly-Asp (or RGD) motif. Thus, Horton, et al., *Exp. Cell Res.* 1991, 195, 368, disclose that RGD-containing peptides and an anti-vitronectin receptor antibody (23C6) inhibit dentine resorption and cell spreading by osteoclasts. In addition, Sato, et al., *J. Cell Biol.* 1990, 111, 1713 discloses that echistatin, a snake venom peptide which contains the RGD sequence, is a potent inhibitor of bone resorption in tissue culture, and inhibits attachment of osteoclasts to bone.

It has now been discovered that certain compounds are potent inhibitors of the $\alpha_v\beta_3$ and $\alpha_v\beta_5$ receptors. In particular, it has been discovered that such compounds are more potent inhibitors of the vitronectin receptor than the fibrinogen receptor.

SUMMARY OF THE INVENTION

This invention comprises compounds of the formula (I) as described hereinafter, which have pharmacological activity for the inhibition of the vitronection receptor and are useful in the treatment of inflammation, cancer and cardiovascular disorders, such as atherosclerosis and restenosis, and diseases wherein bone resorption is a factor, such as osteoporosis.

This invention is also a pharmaceutical composition comprising a compound according to formula (I) and a pharmaceutically carrier.

This invention is also a method of treating diseases which are mediated by the vitronectin receptor. In a particular aspect, the compounds of this invention are useful for treating atherosclerosis, restenosis, inflammation, cancer and diseases wherein bone resorption is a factor, such as osteoporosis.

DETAILED DESCRIPTION

This invention comprises novel compounds which are more potent inhibitors of the vitronectin receptor than the fibrinogen receptor. The novel compounds comprise a benzazepine core in which a nitrogen-containing substituent is present on the aromatic six-membered ring of the benzazepine and an aliphatic substituent containing an acidic moiety is present on the seven-membered ring of the benzazepine. The benzazepine ring system is believed to interact favorably with the vitronectin receptor and to orient the substituent sidechains on the six and seven membered rings so that they may also interact favorably with the receptor. It is preferred that about twelve to fourteen intervening covalent bonds via the shortest intramolecular path will exist between the acidic group on the aliphatic substituent of the seven-membered ring of the benzazepine and the nitrogen of the nitrogen-containing substituent on the aromatic six-membered ring of the benzazepine.

This invention comprises compounds of formula (I):

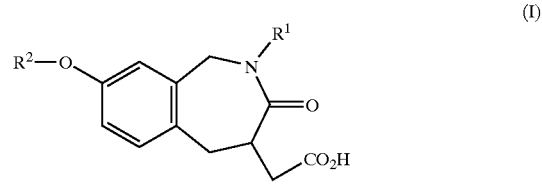

(I)

wherein:

$R^1$ is $R^7$, or A-$C_{0-4}$alkyl, A-$C_{2-4}$alkenyl, A-$C_{2-4}$alkynyl, A-$C_{3-4}$oxoalkenyl, A-$C_{3-4}$oxoalkynyl, A-$C_{1-4}$aminoalkyl, A-$C_{3-4}$aminoalkenyl, A-$C_{3-4}$aminoalkynyl, optionally substituted by any accessible combination of one or more of $R^{10}$ or $R^7$;

A is H, $C_{3-6}$cycloalkyl, Het or Ar;

$R^7$ is —$COR^8$, —$COCR'_2R^9$, —$C(S)R^8$, —$S(O)_mOR'$, —$S(O)_mNR'R''$, —$PO(OR')$, —$PO(OR')_2$, —$NO_2$, or tetrazolyl;

each $R^8$ independently is —OR', —NR'R", —NR'SO$_2$R', —NR'OR', or —OCR'$_2$CO(O)R';

$R^9$ is —OR', —CN, —S(O)$_r$R', —S(O)$_m$NR'$_2$, —C(O)R', C(O)NR'$_2$, or —CO$_2$R';

$R^{10}$ is H, halo, —OR$^{11}$, —CN, —NR'R$^{11}$, —NO$_2$, —CF$_3$, CF$_3$S(O)$_r$—, —CO$_2$R', —CONR'$_2$, A-C$_{0-6}$alkyl-, A-C$_{1-6}$oxoalkyl-, A-C$_{2-6}$alkenyl-, A-C$_{2-6}$alkynyl-, A-C$_{0-6}$alkyloxy-, A-C$_{0-6}$alkylamino- or A-C$_{0-6}$alkyl-S(O)$_r$—;

$R^{11}$ is R', —C(O)R', —C(O)NR'$_2$, —C(O)OR', —S(O)$_m$R', or —S(O)$_m$NR'$_2$;

$R^2$ is

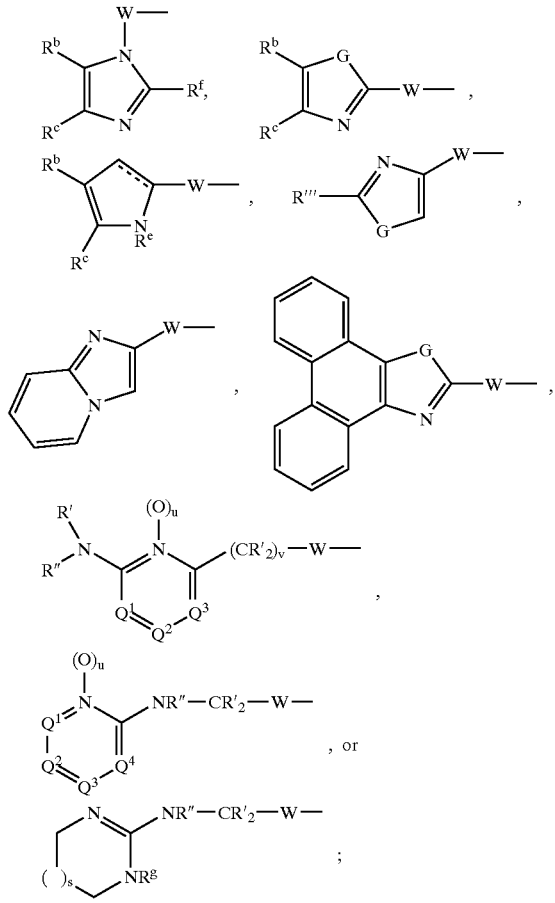

W is —(CHR$^g$)$_a$—U—(CHR$^g$)$_b$—;

U is absent or CO, CR$^g$$_2$, C(=CR$^g$$_2$), S(O)$_k$, O, NR$^g$, CR$^g$OR$^g$, CR$^g$(OR$^k$)CR$^g$$_2$, CR$^g$$_2$CR$^g$(OR$^k$), C(O)CR$^g$$_2$, CR$^g$$_2$C(O), CONR$^i$, NR$^i$CO, OC(O), C(O)O, C(S)O, OC(S), C(S)NR$^g$, NR$^g$C(S), S(O)$_2$NR$^g$, NR$^g$S(O)$_2$, N=N, NR$^g$NR$^g$, NR$^g$CR$^g$$_2$, CR$^g$$_2$NR$^g$, CR$^g$$_2$O, OCR$^g$$_2$, C≡C or CR$^g$=CR$^g$;

G is NR$^e$, S or O;

$R^g$ is H, C$_{1-6}$alkyl, Het-C$_{0-6}$alkyl, C$_{1-7}$cycloalkyl-C$_{0-6}$alkyl or Ar—C$_{0-6}$alkyl;

$R^k$ is R$^g$, —C(O)R$^g$, or —C(O)OR$^f$;

$R^i$ is is H, C$_{1-6}$alkyl, Het-C$_{0-6}$alkyl, C$_{3-7}$cycloalkyl-C$_{0-6}$alkyl, Ar—C$_{0-6}$alkyl, or C$_{1-6}$alkyl substituted by one to three groups chosen from halogen, CN, NR$^g$$_2$, OR$^g$, SR$^g$, CO$_2$R$^g$, and CON(R$^g$)$_2$;

$R^f$ is H, C$_{1-6}$alkyl or Ar—C$_{0-6}$alkyl;

$R^e$ is H, C$_{1-6}$alkyl, Ar—C$_{0-6}$alkyl, Het-C$_{0-6}$alkyl, C$_{3-7}$cycloalkyl-C$_{0-6}$alkyl, or (CH$_2$)$_k$CO$_2$R$^g$;

$R^b$ and $R^c$ are independently selected from H, C$_{1-6}$alkyl, Ar—C$_{0-6}$alkyl, Het-C$_{0-6}$alkyl, or C$_{3-6}$cycloalkyl-C$_{0-6}$alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$, or $R^b$ and $R^c$ are joined together to form a five or six membered aromatic or non-aromatic carbocyclic or heterocyclic ring, optionally substituted by up to three substituents chosen from halogen, CF$_3$, C$_{1-4}$alkyl, OR$^f$, S(O)$_k$R$^f$, COR$^f$, CO$_2$R$^f$, OH, NO$_2$, N(R$^f$)$_2$, CO(NR$^f$)$_2$, and CH$_2$N(R$^f$)$_2$; or methylenedioxy;

$Q^1$, $Q^2$, $Q^3$ and $Q^4$ are independently N or C—R$^y$, provided that no more than one of $Q^1$, $Q^2$, $Q^3$ and $Q^4$ is N;

R' is H, C$_{1-6}$alkyl, Ar—C$_{0-6}$alkyl or C$_{3-6}$cycloalkyl-C$_{0-6}$alkyl;

R" is R', —C(O)R' or —C(O)OR';

R'" is H, C$_{1-6}$alkyl, Ar—C$_{0-6}$alkyl, Het-C$_{0-6}$alkyl, or C$_{3-6}$cycloalkyl-C$_{0-6}$alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$;

$R^y$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$ or —CONR$^g$$_2$, or C$_{1-6}$alkyl optionally substituted by halo, —OR$^g$, —SR$^g$, —CN, —NR$^g$R", —NO$_2$, —CF$_3$, R'S(O)$_r$—, —CO$_2$R$^g$, —COR$^g$ or —CONR$^g$$_2$;

a is 0, 1 or 2;
b is 0, 1 or 2;
k is 0, 1 or 2;
m is 1 or 2;
r is 0, 1 or 2;
s is 0, 1 or 2;
u is 0 or 1; and
v is 0 or 1;

or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In cases wherein compounds may exist in tautomeric forms, such as keto-enol tautomers, such as

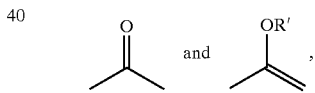

and each tautomeric form is contemplated as being included within this invention whether existing in equilibrium or locked in one form by appropriate substitution with R'.

The compounds of formula (I) inhibit the binding of vitronectin and other RGD-containing peptides to the vitronectin receptor. Inhibition of the vitronectin receptor on osteoclasts inhibits osteoclastic bone resorption and is useful in the treatment of diseases wherein bone resorption is associated with pathology, such as osteoporosis and osteoarthritis.

In another aspect, this invention is a method for stimulating bone formation which comprises administering a compound which causes an increase in osteocalcin release. Increased bone production is a clear benefit in disease states wherein there is a deficiency of mineralized bone mass or remodeling of bone is desired, such as fracture healing and the prevention of bone fractures. Diseases and metabolic disorders which result in loss of bone structure would also benefit from such treatment. For instance, hyperparathyroidism, Paget's disease, hypercalcemia of malignancy, osteolytic lesions produced by bone metastasis, bone loss due to immobilization or sex hormone deficiency, Behcet's disease, osteomalacia, hyperostosis and osteopetrosis, could benefit from administering a compound of this invention.

Additionally, since the compounds of the instant invention inhibit vitronectin receptors on a number of different types of cells, said compounds would be useful in the treatment of inflammatory disorders, such as rheumatoid arthritis and psoriasis, and cardiovascular diseases, such as atherosclerosis and restenosis. The compounds of Formula (I) of the present invention may be useful for the treatment or prevention of other diseases including, but not limited to, thromboembolic disorders, asthma, allergies, adult respiratory distress syndrome, graft versus host disease, organ transplant rejection, septic shock, eczema, contact dermatitis, inflammatory bowel disease, and other autoimmune diseases. The compounds of the present invention may also be useful for wound healing.

The compounds of the present invention are also useful for the treatment, including prevention, of angiogenic disorders. The term angiogenic disorders as used herein includes conditions involving abnormal neovascularization. Where the growth of new blood vessels is the cause of, or contributes to, the pathology associated with a disease, inhibition of angiogenisis will reduce the deleterious effects of the disease. An example of such a disease target is diabetic retinopathy. Where the growth of new blood vessels is required to support growth of a deleterious tissue, inhibition of angiogenisis will reduce the blood supply to the tissue and thereby contribute to reduction in tissue mass based on blood supply requirements. Examples include growth of tumors where neovascularization is a continual requirement in order that the tumor grow and the establishment of solid tumor metastases. Thus, the compounds of the present invention inhibit tumor tissue angiogenesis, thereby preventing tumor metastasis and tumor growth.

Thus, according to the methods of the present invention, the inhibition of angiogenesis using the compounds of the present invention can ameliorate the symptoms of the disease, and, in some cases, can cure the disease.

Another therapeutic target for the compounds of the instant invention are eye diseases chacterized by neovascularization. Such eye diseases include corneal neovascular disorders, such as corneal transplantation, herpetic keratitis, luetic keratitis, pterygium and neovascular pannus associated with contact lens use. Additional eye diseases also include age-related macular degeneration, presumed ocular histoplasmosis, retinopathy of prematurity and neovascular glaucoma.

This invention further provides a method of inhibiting tumor growth which comprises administering stepwise or in physical combination a compound of formula (I) and an antineoplastic agent, such as topotecan and cisplatin.

With respect to formula (I):

Suitably $R^2$ is

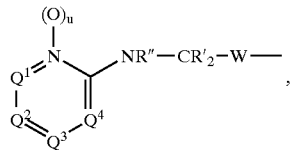

wherein $Q^1$, $Q^2$, and $Q^3$ are each $CR^y$, $Q^4$ is $CR^y$ or N and u is 0, and preferably, each R' is H, R" is H, $C_{1-6}$alkyl, —C(O)$C_{1-6}$alkyl, C(O)O$C_{1-6}$alkyl, —C(O)$C_{0-6}$alkyl-Ar, or C(O)O$C_{0-6}$alkyl-Ar, W is —CH$_2$—CH$_2$—, and $R^y$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$—CONR$^g_2$, or $C_{1-6}$alkyl.

Alternately $R^2$ is

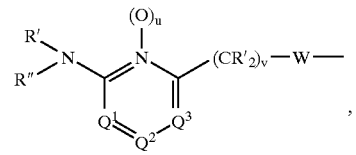

wherein $Q^1$, $Q^2$, and $Q^3$ are each CH and u is 0, and preferably, each R' is H, R" is H or $C_{1-4}$alkyl, W is —CH$_2$—CH$_2$— and v is 0.

Alternately $R^2$ is

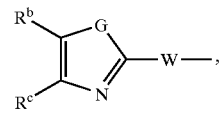

wherein G is NH and $R^b$ and $R^c$ are each H, and preferably, W is —NR$^g$—(CHR$^g$)$_b$—;

Alternately $R^2$ is

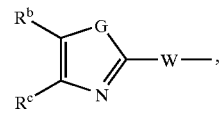

wherein G is NH and $R^b$ and $R^c$ are joined together to form a five or six membered aromatic or non-aromatic carbocyclic or heterocyclic ring, optionally substituted by up to three substituents chosen from halogen, CF$_3$, $C_{1-4}$alkyl, OR$^f$, S(O)$_k$R$^f$, COR$^f$, CO$_2$R$^f$, OH, NO$_2$, N(R$^f$)$_2$, CO(NR$^f$)$_2$, and CH$_2$N(R$^f$)$_2$; or methylenedioxy. Preferably, $R^b$ and $R^c$ are joined together to form a six membered aromatic carbocyclic or heterocyclic ring and W is —CH$_2$—CH$_2$—.

Alternately $R^2$ is

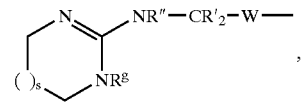

wherein each R' is H, R" is H or $C_{1-4}$alkyl, R$^g$ is H or $C_{1-4}$alkyl and s is 0, 1 or 2 and, preferably, W is —CH$_2$—CH$_2$—.

With respect to formula (I), suitably $R^1$ is H, $C_{1-6}$alkyl, Ar—$C_{0-6}$alkyl, Het-$C_{0-6}$alkyl, $C_{3-6}$cycloalkyl-$C_{0-6}$alkyl, —CH$_2$CF$_3$, —(CH$_2$)$_{1-2}$C(O)OR', or —(CH$_2$)$_2$OR'. Preferably, $R^1$ is H, $C_{1-4}$alkyl, Ph-$C_{0-4}$alkyl, —CH$_2$CF$_3$, —(CH$_2$)$_{1-2}$C(O)OR—, or —(CH$_2$)$_2$OR', in which R' is H or $C_{1-4}$alkyl. Most preferably, $R^1$ is —CH$_2$CF$_3$.

Representative of the novel compounds of this invention are the following:

(±)-8-[3-(2-pyridylamino)-1-propyloxy]-3-oxo-2,3,4,5-tetrahydro-1H-2-benzazepine-4-acetic acid;

(±)-8-[3-(4-amino-2-pyridylamino)-1-propyloxy]-3-oxo-2,3,4,5-tetrahydro-1H-2-benzazepine-4-acetic acid;

(±)-8-[3-(4-methoxy-2-pyridylamino)-1-propyloxy]-3-oxo-2,3,4,5-tetrahydro-1H-2-benzazepine-4-acetic acid;

(±)-8-[3-(2-pyridylamino)-1-propyloxy]-2-methyl-3-oxo-2,3,4,5-tetrahydro-1H-2-benzazepine-4-acetic acid;

(±)-8-[3-(2-imidazolylamino)-1-propyloxy]-3-oxo-2,3,4,5-tetrahydro-1H-2-benzazepine-4-acetic acid;

(±)-8-[3-[2-(1,4,5,6-tetrahydropyrimidinyl)amino]-1-propyloxy]-3-oxo-2,3,4,5-tetrahydro-1H-2-benzazepine-4-acetic acid;

(±)-8-[2-[6-(methylamino)pyridyl]ethoxy]-3-oxo-2,3,4,5-tetrahydro-1H-2-benzazepine-4-acetic acid;

(±)-8-[2-(2-benzimidazolyl)ethoxy]-3-oxo-2,3,4,5-tetrahydro-1H-2-benzazepine-4-acetic acid;

(±)-8-[2-(4-aza-2-benzimidazolyl)ethoxy]-3-oxo-2,3,4,5-tetrahydro-1H-2-benzazepine-4-acetic acid;

(±)-8-[2-[6-(methylamino)pyridin-2-yl]-1-ethoxy]-3-oxo-2,3,4,5-tetrahydro-1H-2-benzazepine-4-acetic acid;

(±)-8-[2-(benzimidazol-2-yl)-1-ethoxy]-3-oxo-2,3,4,5-tetrahydro-1H-2-benzazepine-4-acetic acid;

(±)-8-[3-(4-aminopyridin-2-ylamino)-1-propyloxy]-2-methyl-3-oxo-2,3,4,5-tetrahydro-1H-2-benzazepine-4-acetic acid;

(±)-3-oxo-8-[3-(pyrimidin-2-ylamino)-1-propyloxy]-2,3,4,5-tetrahydro-1H-2-benzazepine-4-acetic acid;

(R)-8-[3-(4-aminopyridin-2-ylamino)-1-propyloxy]-3-oxo-2,3,4,5-tetrahydro-1H-2-benzazepine-4-acetic acid;

(±)-3-oxo-[3-[(1,4,5,6-tetrahydropyrimidin-2-yl)amino]-1-propyloxy]-2,3,4,5-tetrahydro-1H-2-benzazepine-4-acetic acid;

(S)-8-[3-(4-aminopyridin-2-ylamino)-1-propyloxy]-3-oxo-2,3,4,5-tetrahydro-1H-2-benzazepine-4-acetic acid;

(±)-3-oxo-8-[3-[N-(pyridin-2-yl)-N-(tert-butoxycarbonyl)amino]-1-propyloxy]-2,3,4,5-tetrahydro-1H-2-benzazepine-4-acetic acid;

(±)-8-[3-[N-(1-oxopyridin-2-yl-N-(tert-butoxycarbonyl)amino]-1-propyloxy]-3-oxo-2,3,4,5-tetrahydro-1H-2-benzazepine-4-acetic acid;

(±)-3-oxo-8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetic acid;

(±)-3-oxo-8-[3-(pyridin-2-ylamino)-1-propyloxy]-2-(4-trifluoromethylbenzyl)-2,3,4,5-tetrahydro-1H-2-benzazepine-4-acetic acid;

(±)-2-methyl-3-oxo-8-[3-[N-(pyridin-2-yl)-N-(methyl)amino)]-1-propyloxy]-2,3,4,5-tetrahydro-1H-2-benzazepine-4-acetic acid;

(±)-2-benzyl-3-oxo-8-[3-(pyridin-2-ylamino)-1-propyloxy]-2,3,4,5-tetrahydro-1H-2-benzazepine-4-acetic acid;

(±)-2-(carboxymethyl)-3-oxo-8-[3-(pyridin-2-ylamino)-1-propyloxy]-2,3,4,5-tetrahydro-1H-2-benzazepine-4-acetic acid;

(±)-2-(4-aminobenzyl)-3-oxo-8-[3-(pyridin-2-ylamino)-1-propyloxy]-2,3,4,5-tetrahydro-1H-2-benzazepine-4-acetic acid;

(±)-3-oxo-8-[3-[N-(pyridin-2-yl)-N-(benzoyl)amino]-1-propyloxy]-2-(4-trifluoromethylbenzyl)-2,3,4,5-tetrahydro-1H-2-benzazepine-4-acetic acid;

(±)-8-[3-(2-imidazolin-2-ylamino)-1-propyloxy]-2-methyl-3-oxo-2,3,4,5-tetrahydro-1H-2-benzazepine-4-acetic acid;

(±)-3-oxo-8-[3-(pyridin-2-ylamino)-1-propyloxy]-2-(2,2,2-trifluoroethyl)-2,3,4,5-tetrahydro-1H-2-benzazepine-4-acetic acid;

(±)-8-[2-(2-aminothiazol-4-yl)-1-ethoxy]-2-methyl-3-oxo-2,3,4,5-tetrahydro-1H-2-benzazepine-4-acetic acid;

(±)-8-[3-(4,6-dimethylpyridin-2-ylamino)-1-propyloxy]-2-methyl-3-oxo-2,3,4,5-tetrahydro-1H-2-benzazepine-4-acetic acid;

(±)-8-[3-(4,5,6,7-tetrahydro-1H-1,3-diazepin-2-ylamino)-1-propyloxy]-2-methyl-3-oxo-2,3,4,5-tetrahydro-1H-2-benzazepine-4-acetic acid;

(±)-3-oxo-8-[3-[N-(pyridin-2-yl)-N-(tert-butylacetyl)amino]-1-propyloxy]-2-(4-trifluoromethylbenzyl)-2,3,4,5-tetrahydro-1H-2-benzazepine-4-acetic acid;

(±)-3-oxo-8-[3-[N-(pyridin-2-yl)-N-(isobutoxycarbonyl)amino]-1-propyloxy]-2-(4-trifluoromethylbenzyl)-2,3,4,5-tetrahydro-1H-2-benzazepine-4-acetic acid;

(S)-3-oxo-8-[3-(pyridin-2-ylamino)-1-propyloxy]-2-(4-trifluoromethylbenzyl)-2,3,4,5-tetrahydro-1H-2-benzazepine-4-acetic acid;

(±)-3-oxo-8-[3-(4-methylpyridin-2-ylamino)-1-propyloxy]-2-(2,2,2-trifluoroethyl)-2,3,4,5-tetrahydro-1H-2-benzazepine-4-acetic acid;

(±)-3-oxo-8-[3-[N-(pyridin-2-yl)-N-(methyl)amino)]-1-propyloxy]-2-[4-(trifluoromethyl)benzyl]-2,3,4,5-tetrahydro-1H-2-benzazepine-4-acetic acid;

(S)-3-oxo-8-[3-(pyridin-2-ylamino)-1-propyloxy]-2-(2,2,2-trifluoroethyl)-2,3,4,5-tetrahydro-1H-2-benzazepine-4-acetic acid;

(R)-3-oxo-8-[3-(pyridin-2-ylamino)-1-propyloxy]-2-(2,2,2-trifluoroethyl)-2,3,4,5-tetrahydro-1H-2-benzazepine-4-acetic acid;

(S)-8-[3-(4-methylpyridin-2-ylamino)-1-propyloxy]-3-oxo-2-(2,2,2-trifluoroethyl)-2,3,4,5-tetrahydro-1H-2-benzazepine-4-acetic acid;

(S)-3-oxo-8-[3-(1,4,5,6-tetrahydropyrimid-2-ylamino)-1-propyloxy]-2-[4-(trifluoromethyl)benzyl]-2,3,4,5-tetrahydro-1H-2-benzazepine-4-acetic acid;

(S)-3-oxo-2-(2-phenylethyl)-8-[3-(pyridin-2-ylamino)-1-propyloxy]-2,3,4,5-tetrahydro-1H-2-benzazepine-4-acetic acid;

(S)-8-[2-[6-(methylamino)pyridin-2-yl]-1-ethoxy]-3-oxo-2-(2-phenylethyl)-2,3,4,5-tetrahydro-1H-2-benzazepine-4-acetic acid;

(S)-8-[2-[6-(methylamino)pyridin-2-yl]-1-ethoxy]-3-oxo-2-(2,2,2-trifluoroethyl)-2,3,4,5-tetrahydro-1H-2-benzazepine-4-acetic acid; and (S)-8-[2-[6-(methylamino)pyridin-2-yl]-1-ethoxy]-3-oxo-2-[4-(trifluoromethyl)benzyl]-2,3,4,5-tetrahydro-1H-2-benzazepine-4-acetic acid;

or a pharmaceutically acceptable salt thereof.

Preferred compounds of this invention include:

(S)-3-oxo-8-[3-(pyridin-2-ylamino)-1-propyloxy]-2-(2,2,2-trifluoroethyl)-2,3,4,5-tetrahydro-1H-2-benzazepine-4-acetic acid;

(S)-3-oxo-8-[3-(pyridin-2-ylamino)-1-propyloxy]-2-(2,2,2-trifluoroethyl)-2,3,4,5-tetrahydro-1H-2-benzazepine-4-acetic acid;

(S)-8-[2-[6-(methylamino)pyridin-2-yl]-1-ethoxy]-3-oxo-2-(2,2,2-trifluoroethyl)-2,3,4,5-tetrahydro-1H-2-benzazepine-4-acetic acid; and (S)-8-[3-(4-methylpyridin-2-ylamino)-1-propyloxy]-3-oxo-2-(2,2,2-trifluoroethyl)-2,3,4,5-tetrahydro-1H-2-benzazepine-4-acetic acid;

or a pharmaceutically acceptable salt thereof.

In cases wherein the compounds of this invention may have one or more chiral centers, unless specified, this invention includes each unique nonracemic compound which may be synthesized and resolved by conventional techniques. According to the present invention, the (S) configuration of the formula (I) compounds is preferred.

In cases in which compounds have unsaturated carbon-carbon double bonds, both the cis (Z) and trans (E) isomers are within the scope of this invention. The meaning of any substituent at any one occurrence is independent of its meaning, or any other substituent's meaning, at any other occurrence.

Also included in this invention are prodrugs of the compounds of this invention. Prodrugs are considered to be any covalently bonded carriers which release the active parent drug according to formula (I) in vivo. Thus, in another aspect of this invention are novel prodrugs, which are also intermediates in the preparation of formula (I) compounds, of formula (II):

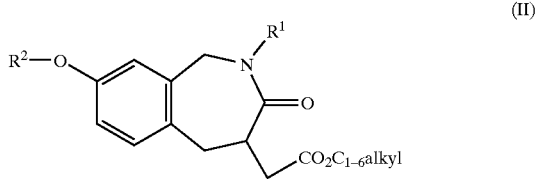

(II)

wherein:

$R^1$ is $R^7$, or A-$C_{0-4}$alkyl, A-$C_{2-4}$alkenyl, A-$C_{2-4}$alkynyl, A-$C_{3-4}$oxoalkenyl, A-$C_{3-4}$oxoalkynyl, A-$C_{1-4}$aminoalkyl, A-$C_{3-4}$aminoalkenyl, A-$C_{3-4}$aminoalkynyl, optionally substituted by any accessible combination of one or more of $R^{10}$ or $R^7$;

A is H, $C_{3-6}$cycloalkyl, Het or Ar;

$R^7$ is —$COR^8$, —$COCR'_2R^9$, —$C(S)R^8$, —$S(O)_mOR'$, —$S(O)_mNR'R''$, —$PO(OR')$, —$PO(OR')_2$, —$NO_2$, or tetrazolyl;

each $R^8$ independently is —OR', —NR'R'', —NR'$SO_2$R', —NR'OR', or —$OCR'_2CO(O)R'$;

$R^9$ is —OR', —CN, —$S(O)_rR'$, —$S(O)_mNR'_2$, —C(O)R', C(O)NR'$_2$, or —$CO_2$R';

$R^{10}$ is H, halo, —$OR^{11}$, —CN, —$NR'R^{11}$, —$NO_2$, —$CF_3$, $CF_3S(O)_r$—, —$CO_2R'$, —$CONR'_2$, A-$C_{0-6}$alkyl-, A-$C_{1-6}$oxoalkyl-, A-$C_{2-6}$alkenyl-, A-$C_{2-6}$alkynyl-, A-$C_{0-6}$alkyloxy-, A-$C_{0-6}$alkylamino- or A-$C_{0-6}$alkyl-$S(O)_r$—;

$R^{11}$ is R', —C(O)R', —C(O)NR'$_2$, —C(O)OR', —$S(O)_mR'$, or —$S(O)_mNR'_2$;

$R^2$ is

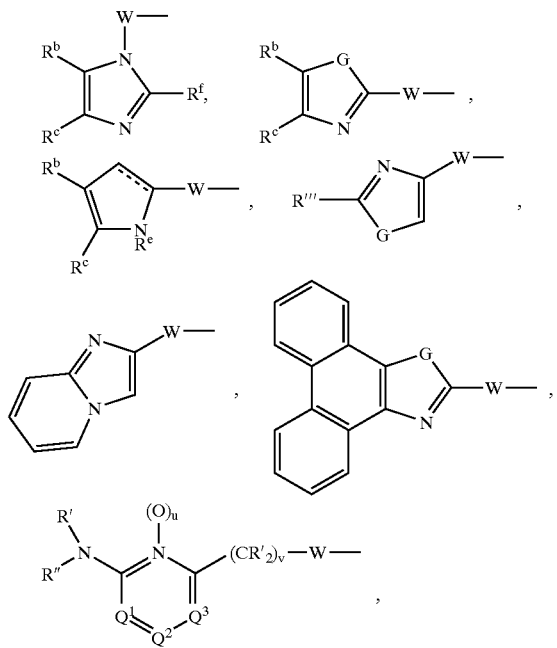

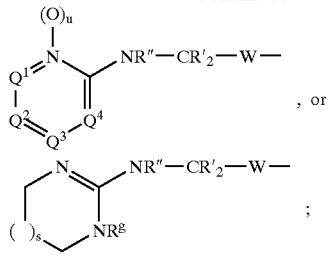

, or

W is —(CHR$^g$)$_a$—U—(CHR$^g$)$_b$—;

U is absent or CO, CR$^g_2$, C(=CR$^g_2$), S(O)$_k$, O, NR$^g$, CR$^g$OR$^g$, CR$^g$(OR$^k$)CR$^g_2$, CR$^g_2$CR$^g$(OR$^k$), C(O)CR$^g_2$, CR$^g_2$C(O), CONR$^i$, NR$^i$CO, OC(O), C(O)O, C(S)O, OC(S), C(S)NR$^g$, NR$^g$C(S), S(O)$_2$NR$^g$, NR$^g$S(O)$_2$ N=N, NR$^g$NR$^g$, NR$^g$CR$^g_2$, CR$^g_2$NR$^g$, CR$^g_2$O, OCR$^g_2$, C≡C or CR$^g$=CR$^g$;

G is NR$^e$, S or O;

$R^g$ is H, $C_{1-6}$alkyl, Het-$C_{0-6}$alkyl, $C_{3-7}$cycloalkyl-$C_{0-6}$alkyl or Ar—$C_{0-6}$alkyl;

$R^k$ is R$^g$, —C(O)R$^g$, or —C(O)OR$^f$;

$R^i$ is is H, $C_{1-6}$alkyl, Het-$C_{0-6}$alkyl, $C_{3-7}$cycloalkyl-$C_{0-6}$alkyl, Ar—$C_{0-6}$alkyl, or $C_{1-6}$alkyl substituted by one to three groups chosen from halogen, CN, NR$^g_2$, OR$^g$, SR$^g$, CO$_2$R$^g$, and CON(R$^g$)$_2$;

$R^f$ is H, $C_{1-6}$alkyl or Ar—$C_{0-6}$alkyl;

$R^e$ is H, $C_{1-6}$alkyl, Ar—$C_{0-6}$alkyl, Het-$C_{0-6}$alkyl, $C_{3-7}$cycloalkyl-$C_{0-6}$alkyl, or (CH$_2$)$_k$CO$_2$R$^g$;

$R^b$ and $R^c$ are independently selected from H, $C_{1-6}$alkyl, Ar—$C_{0-6}$alkyl, Het-$C_{0-6}$alkyl, or $C_{3-6}$cycloalkyl-$C_{0-6}$alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$, or R$^b$ and R$^c$ are joined together to form a five or six membered aromatic or non-aromatic carbocyclic or heterocyclic ring, optionally substituted by up to three substituents chosen from halogen, CF$_3$, $C_{1-4}$alkyl, OR$^f$, S(O)$_k$R$^f$, COR$^f$, CO$_2$R$^f$, OH, NO$_2$, N(R$^f$)$_2$, CO(NR$^f$)$_2$, and CH$_2$N(R$^f$)$_2$; or methylenedioxy;

$Q^1$, $Q^2$, $Q^3$ and $Q^4$ are independently N or C—R$^y$, provided that no more than one of $Q^1$, $Q^2$, $Q^3$ and $Q^4$ is N;

R' is H, $C_{1-6}$alkyl, Ar—$C_{0-6}$alkyl or $C_{3-6}$cycloalkyl-$C_{0-6}$alkyl;

R'' is R', —C(O)R' or —C(O)OR';

R''' is H, $C_{1-6}$alkyl, Ar—$C_{0-6}$alkyl, Het-$C_{0-6}$alkyl, or $C_{3-6}$cycloalkyl-$C_{0-6}$alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$;

$R^y$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$ or —CONR$^g_2$, or $C_{1-6}$alkyl optionally substituted by halo, —OR$^g$, —SR$^g$, —CN, —NR$^g$R'', —NO$_2$, —CF$_3$, R'S(O)$_r$—, —CO$_2$R$^g$, —COR$^g$ or —CONR$^g_2$;

a is 0, 1 or 2;

b is 0, 1 or 2;

k is 0, 1 or 2;

m is 1 or 2;

r is 0, 1 or 2;

s is 0, 1 or 2;

u is 0 or 1; and v is 0 or 1;

or a pharmaceutically acceptable salt thereof.

Representative of the novel prodrugs of this invention are the following:

methyl (±)-3-oxo-8-[3-(pyridin-2-ylamino)-1-propyloxy]-2,3,4,5-tetrahydro-1H-2-benzazepine-4-acetate; and ethyl (±)-8-[3-(4-aminopyridin-2-ylamino)-1-propyloxy]-3-oxo-2,3,4,5-tetrahydro-1H-2-benzazepine-4-acetate;

or a pharmaceutically acceptable salt thereof.

In yet another aspect of this invention are novel intermediates of formula (III):

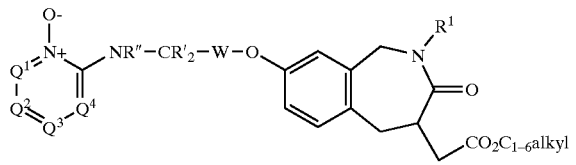

(III)

$R^1$ is $R^7$, or $A-C_{0-4}$alkyl, $A-C_{2-4}$alkenyl, $A-C_{2-4}$alkynyl, $A-C_{3-4}$oxoalkenyl, $A-C_{3-4}$oxoalkynyl, $A-C_{1-4}$aminoalkyl, $A-C_{3-4}$aminoalkenyl, $A-C_{3-4}$aminoalkynyl, optionally substituted by any accessible combination of one or more of $R^{10}$ or $R^7$;

A is H, $C_{3-6}$cycloalkyl, Het or Ar;

$R^7$ is —$COR^8$, —$COCR'_2R^9$, —$C(S)R^8$, —$S(O)_mOR'$, —$S(O)_mNR'R''$, —$PO(OR')$, —$PO(OR')_2$, —$NO_2$, or tetrazolyl;

each $R^8$ independently is —OR', —NR'R'', —$NR'SO_2R'$, —NR'OR', or —$OCR'_2CO(O)R'$;

$R^9$ is —OR', —CN, —$S(O)_rR'$, —$S(O)_mNR'_2$, —C(O)R', $C(O)NR'_2$, or —$CO_2R'$;

$R^{10}$ is H, halo, —$OR^{11}$, —CN, —$NR'R^{11}$, —$NO_2$, —$CF_3$, $CF_3S(O)_r$—, —$CO_2R'$, —$CONR'_2$, $A-C_{0-6}$alkyl-, $A-C_{1-6}$oxoalkyl-, $A-C_{2-6}$alkenyl-, $A-C_{2-6}$alkynyl-, $A-C_{0-6}$alkyloxy-, $A-C_{0-6}$alkylamino- or $A-C_{0-6}$alkyl-$S(O)_r$—;

$R^{11}$ is R', —C(O)R', —$C(O)NR'_2$, —C(O)OR', —$S(O)_mR'$, or —$S(O)_mNR'_2$;

$R^2$ is

W is —$(CHR^g)_a$—U—$(CHR^g)_b$—;

U is absent or CO, $CR^g_2$, C(=$CR^g_2$), $S(O)_k$, O, $NR^g$, $CR^gOR^g$, $CR^g(OR^k)CR^g_2$, $CR^g_2CR^g(OR^k)$, $C(O)CR^g_2$, $CR^g_2C(O)$, $CONR^i$, $NR^iCO$, OC(O), C(O)O, C(S)O, OC(S), $C(S)NR^g$, $NR^gC(S)$, $S(O)_2NR^g$, $NR^gS(O)_2$ N=N, $NR^gNR^g$, $NR^gCR^g_2$, $CR^g_2NR^g$, $CR^g_2O$, $OCR^g_2$, C≡C or $CR^g$=$CR^g$;

$R^g$ is H, $C_{1-6}$alkyl, Het-$C_{0-6}$alkyl, $C_{3-7}$cycloalkyl-$C_{0-6}$alkyl or Ar—$C_{0-6}$alkyl;

$R^k$ is $R^g$, —$C(O)R^g$, or —$C(O)OR^f$;

$R^i$ is is H, $C_{1-6}$alkyl, Het-$C_{0-6}$alkyl, $C_{3-7}$cycloalkyl-$C_{0-6}$alkyl, Ar—$C_{0-6}$alkyl, or $C_{1-6}$alkyl substituted by one to three groups chosen from halogen, CN, $NR^g_2$, $OR^g$, $SR^g$, $CO_2R^g$, and $CON(R^g)_2$;

$R^f$ is H, $C_{1-6}$alkyl or Ar—$C_{0-6}$alkyl;

$Q^1$, $Q^2$, $Q^3$ and $Q^4$ are independently N or C—$R^y$, provided that no more than one of $Q^1$, $Q^2$, $Q^3$ and $Q^4$ is N;

R' is H, $C_{1-6}$alkyl, Ar—$C_{0-6}$alkyl or $C_{3-6}$cycloalkyl-$C_{0-6}$alkyl;

R'' is R', —C(O)R' or —C(O)OR';

$R^y$ is H, halo, —$OR^g$, —$SR^g$, —CN, —$NR^gR^k$, —$NO_2$, —$CF_3$, $CF_3S(O)_r$—, —$CO_2R^g$, —$COR^g$ or —$CONR^g_2$, or $C_{1-6}$alkyl optionally substituted by halo, —$OR^g$, —$SR^g$, —CN, —$NR^gR''$, —$NO_2$, —$CF_3$, R'S$(O)_r$—, —$CO_2R^g$, —$COR^g$ or —$CONR^g_2$;

a is 0, 1 or 2;

b is 0, 1 or 2;

m is 1 or 2; and m is 1 or 2;

r is 0, 1 or 2;

or a pharmaceutically acceptable salt thereof.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

$C_{1-4}$alkyl as applied herein means an optionally substituted alkyl group of 1 to 4 carbon atoms, and includes methyl, ethyl, n-propyl, isopropyl, n-butyl, isobutyl, and t-butyl. $C_{1-6}$alkyl additionally includes pentyl, n-pentyl, isopentyl, neopentyl, and hexyl and the simple aliphatic isomers thereof. $C_{0-4}$alkyl and $C_{0-6}$alkyl additionally indicates that no alkyl group need be present (e.g., that a covalent bond is present).

Any $C_{1-4}$alkyl or $C_{1-6}$ alkyl, $C_{2-6}$ alkenyl, $C_{2-6}$ alkynyl or $C_{1-4}$ oxoalkyl may be optionally substituted with the group $R^x$, which may be on any carbon atom that results in a stable structure and is available by conventional synthetic techniques. Suitable groups for $R^x$ are $C_{1-4}$alkyl, OR', SR', $C_{1-4}$alkylsulfonyl, $C_{1-4}$alkylsulfoxyl, —CN, N(R')$_2$, $CH_2$N (R')$_2$, —$NO_2$, —$CF_3$, —$CO_2R'$—$CON(R')_2$, —COR', —NR'C(O)R', F, Cl, Br, I, or $CF_3S(O)_r$—, wherein r is 0, 1 or 2.

Halogen or halo means F, Cl, Br, and I.

Ar, or aryl, as applied herein, means phenyl or naphthyl, or phenyl or naphtyl substituted by one to three substituents, such as those defined above for alkyl, especially $C_{1-4}$alkyl, $C_{1-4}$alkoxy, $C_{1-4}$alkthio, $CF_3$, $NH_2$, OH, F, Cl, Br or I.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazole, benzopyran, benzothiophene, furan, imidazole, indoline, morpholine, piperidine, piperazine, pyrrole, pyrrolidine, tetrahydropyridine, pyridine, thiazole, thiophene, quinoline, isoquinoline, and tetra- and perhydro-quinoline and isoquinoline. Any accessible combination of up to three substituents on the Het ring, such as those defined above for alkyl that are available by chemical synthesis and are stable are within the scope of this invention.

$C_{3-7}$cycloalkyl refers to an optionally substituted carbocyclic system of three to seven carbon atoms, which may contain up to two unsaturated carbon-carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as those defined above for alkyl, on the cycloalkyl ring that is available by conventional chemical synthesis and is stable, is within the scope of this invention.

When $R^b$ and $R^c$ are joined together to form a five- or six-membered aromatic or non-aromatic carbocyclic or heterocyclic ring fused to the ring to which $R^b$ and $R^c$ are attached, the ring formed will generally be a five- or six-membered heterocycle selected from those listed above for Het, or will be a phenyl, cyclohexyl or cyclopentyl ring.

Preferably $R_b$ and $R_c$ will be -D1=D2-D3=D4 wherein D1–D4 are independently CH, N or C—$R_x$ with the proviso that no more than two of D1–D4 are N. Most preferably, when $R^b$ Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicylohexylcarbodiimide, DMAP refers to dimethylaminopyridine, DIEA refers to diisopropylethyl amine, EDC refers to 1-(3-dimethylaminopropyl)-3-ethylcarbodiimide, hydrochloride. HOBt refers to 1-hydroxybenzotriazole, THF refers to tetrahydrofuran, DIEA refers to refers to 1-(3-dimethylaminopropyl)-3-ethylcarbodiimide, hydrochloride. HOBt refers to 1-hydroxybenzotriazole, THF refers to tetrahydrofuran, DIEA refers to diisopropylethylamine, DEAD refers to diethyl azodicarboxylate, $PPh_3$ refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of formula (IV) with a compound of formula (V):

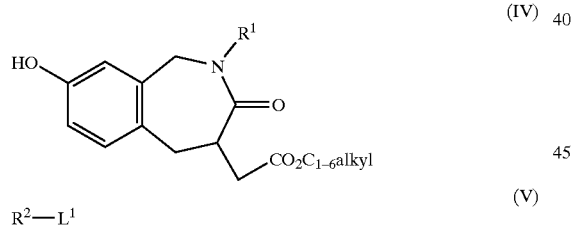

(IV)

(V)

wherein $R^1$ and $R^2$ are as defined in formula (I), with any reactive functional groups protected, and $L^1$ is OH or halo;

and thereafter removing any protecting groups, and optionally forming a pharmaceutically acceptable salt.

Suitably, certain compounds of formula (I) are prepared by reacting a compound of formula (IV) with a compound of formula (VI):

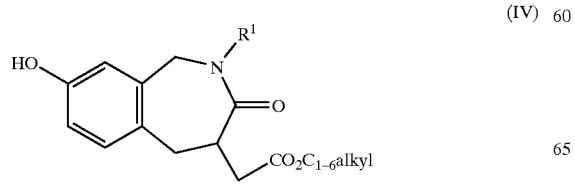

(IV)

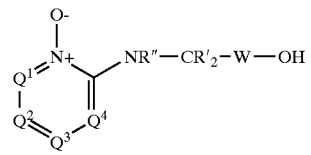

(VI)

wherein $R^1$, R', R", W, $Q^1$, $Q^2$, $Q^3$ and $Q^4$ are as defined in formula (I), with any reactive functional groups protected;

and thereafter removing any protecting groups, and optionally forming a pharmaceutically acceptable salt.

Preferably, for formula (VI) compounds, $Q^1$, $Q^2$, $Q^3$ and $Q^4$ are CH, W is —$CH_2$—$CH_2$—, R' is H and R" is H, $C_{1-4}$alkyl or —C(O)O$C_{1-4}$alkyl. Suitably, the reaction between a compound of formula (IV) with a compound of formula (VI) is carried out in the presence of diethyl azodicarboxylate and triphenylphosphine in an aprotic solvent.

Additionally, certain compounds of formula (I) are prepared by reacting a compound of formula (IV) with a compound of formula (VII):

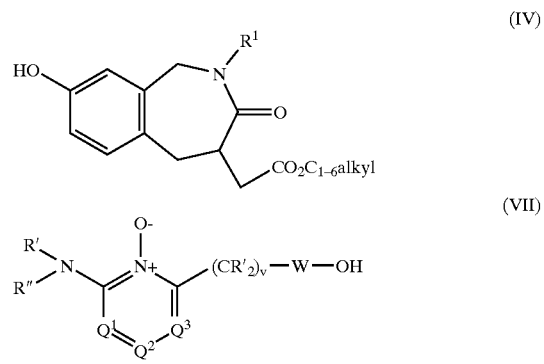

(IV)

(VII)

wherein $R^1$, R', R", W, $Q^1$, $Q^2$, $Q^3$ and $Q^4$ are as defined in formula (I), with any reactive functional groups protected;

and thereafter removing any protecting groups, and optionally forming a pharmaceutically acceptable salt.

Preferably, for formula (VII) compounds, $Q^1$, $Q^2$ and $Q^3$ are CH, W is —$CH_2$—$CH_2$—, v is 0, R' is H and R" is H or $C_{1-4}$alkyl. Suitably, the reaction between a compound of formual (IV) with a compound of formula (VII) is carried out in the presence of diethyl azodicarboxylate and triphenylphosphine in an aprotic solvent.

Compounds of the formula (I) are prepared by the general methods described in Schemes I–VII.

Scheme I

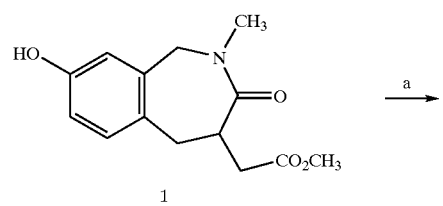

1

-continued

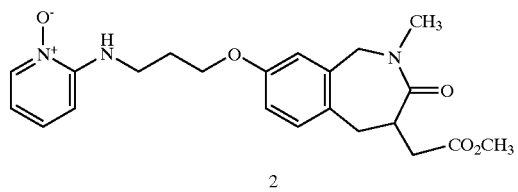

2

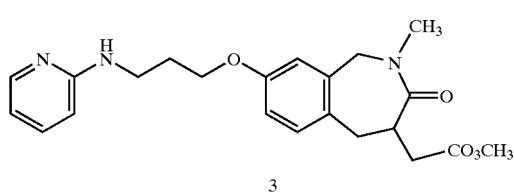

3

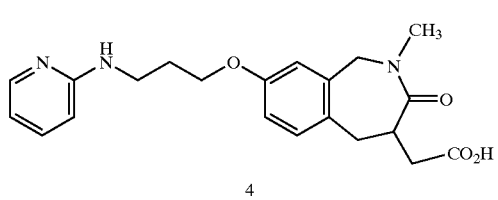

4 a) 2-[(3-hydroxy-1-propyl)amino]pyridine-N-oxide, DEAD, (Ph)₃P, DMF;
b) cyclohexane, 10% Pd/C, 2-propanol;
c) 1.0 N LiOH, THF, H₂O, then acidification.

Compound I-1, the preparation of which follows the general procedures outlined in Bondinell, et al. (WO 93/00095), is reacted with 2-[(3-hydroxy-1-propyl)amino] pyridine-N-oxide in a Mitsunobu-type coupling reaction (*Organic Reactions* 1992, 42, 335–656; *Synthesis* 1981, 1–28) to afford I-2. The reaction is mediated by the complex formed reduced to the corresponding pyridine I-3 under transfer hydrogenation conditions using a solvent, for instance THF, $CH_2Cl_2$, or DMF. The pyridine-N-oxide moiety of I-2 is reduced to the corresponding pyridine I-3 under transfer hydrogenation conditions using a instance methanol, ethanol, or 2-propanol. Cyclohexene, 1,4-cyclohexadiene, formic acid, and salts of formic acid, such as potassium formate or ammonium formate, are commonly used as the hydrogen transfer reagent in this type of reaction. The methyl ester of I-3 is hydrolyzed using aqueous base, for example, LiOH in aqueous THF or NaOH in aqueous for instance TFA or HCl, to afford the carboxylic acid I-4. Alternatively, the intermediate carboxylate salt can be isolated, if desired, or a carboxylate salt of the free carboxylic acid can be prepared by methods well-known to those of skill in the art.

Compounds of formula (I) may also be prepared by alternate methods known to those skilled in the art. For example, the ether linkage of formula (I) compounds may be formed by reacting the alcohol group of a formula 1-Scheme 1 compound with a $R^2$-compound containing a displaceable group, such as a chloro, bromo or iodo group. Other ether-forming reactions can be employed and should be readily apparent to those skilled in the art.

Scheme II

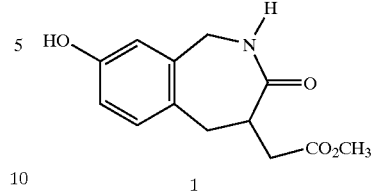

1

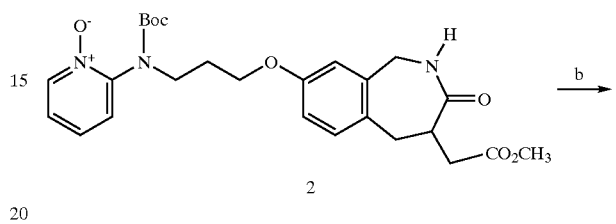

a) 2-[N-(3-hydroxy-1-propyl)-N-(tert-butoxycarbonyl)amino]pyridine-N-oxide, DEAD, (Ph)₃P, DMF;
b) LiHMDS, 4-trifluoromethylbenzyl bromide, DMF;
c) cyclohexane, 10% Pd/C, 2-propanol;
d) 1.0 N NaOH, MeOH;
e) HCl/dioxane;

Compound II-1, prepared as described in Scheme I, is reacted with 2-[N-(3-hydroxy-1-propyl)-N-(tert-butoxycarbonyl)amino pyridine-N-oxide in a Mitsunobu-type coupling reaction as described in detail in Scheme I. The resulting product, II-2, can be alkylated at position 2 (benzazepine numbering) under standard alkylation conditions well-known to those of skill in the art. For example, II-2 can be treated with a base, such as sodium hydride, LDA, or lithium hexamethyldisilazide, in an appropriate solvent, usually THF, DMF, DME, or mixtures thereof, to effect deprotonation of the amide N-H. Treatment of the resulting anionic species with an appropriate electrophile, such as an alkyl or benzyl halide, results in N-alkylation to afford the product, for example II-3. The N-oxide of II-3 can be reduced as described in Scheme I to afford II-4, which can be saponified to II-5 as described in Scheme I. Deprotection of II-5 to afford II-6 is accomplished under standard acidic conditions as described in Greene, "Protective Groups in Organic Synthesis" (published by Wiley-Interscience). Such conditions are well-known to those of skill in the art. Alternatively, conversion of II-3 to II-6 can be accomplished by an alternate sequence, for example initial Boc deprotection of II-3, followed by reduction of the N-oxide, and finally saponification.

2 molar equivalents of a base, such as sodium hydride, LDA, or lithium hexamethyldisilazide, in an appropriate solvent, usually THF, DMF, DME, or mixtures thereof, to effect deprotonation. Treatment of the resulting anionic species with an excess of an appropriate electrophile, such as an alkyl or benzyl halide, results in bis-alkylation to afford the product, for example III-3. Conversion of III-3 to III-5 follows the methods described in Schemes I and II.

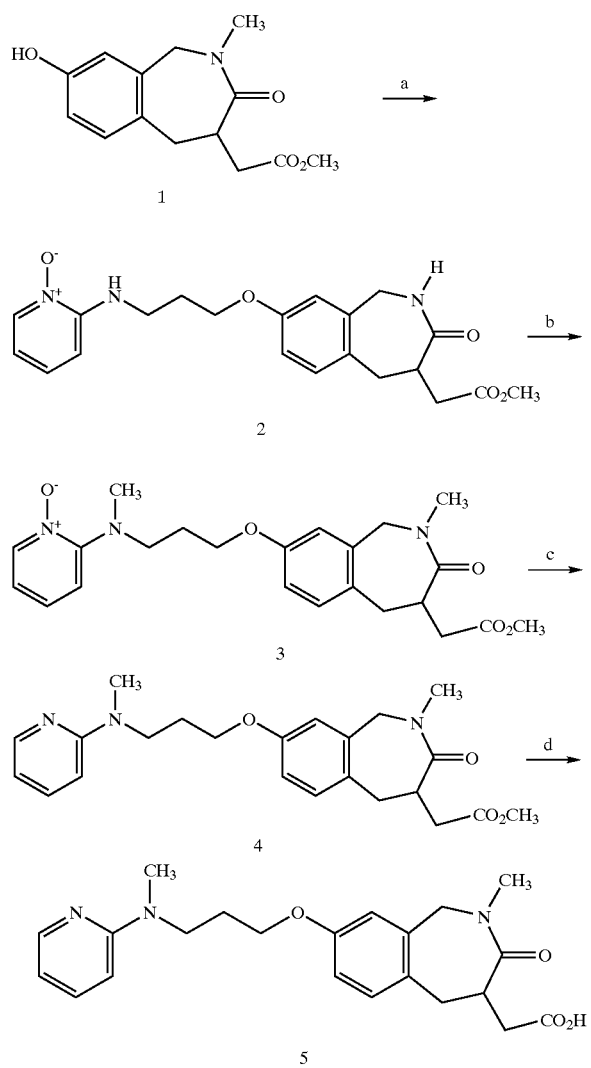

Scheme III a) 2-[(3-hydroxy-1-propyl)amino]pyridine-N-oxide, DEAD, (Ph)$_3$P, DMF;
b) LiHMDS, CH$_3$I, DMF;
c) cyclohexane, 10% Pd/C, 2-propanol;
d) 1.0 N MeOH, then acidification.

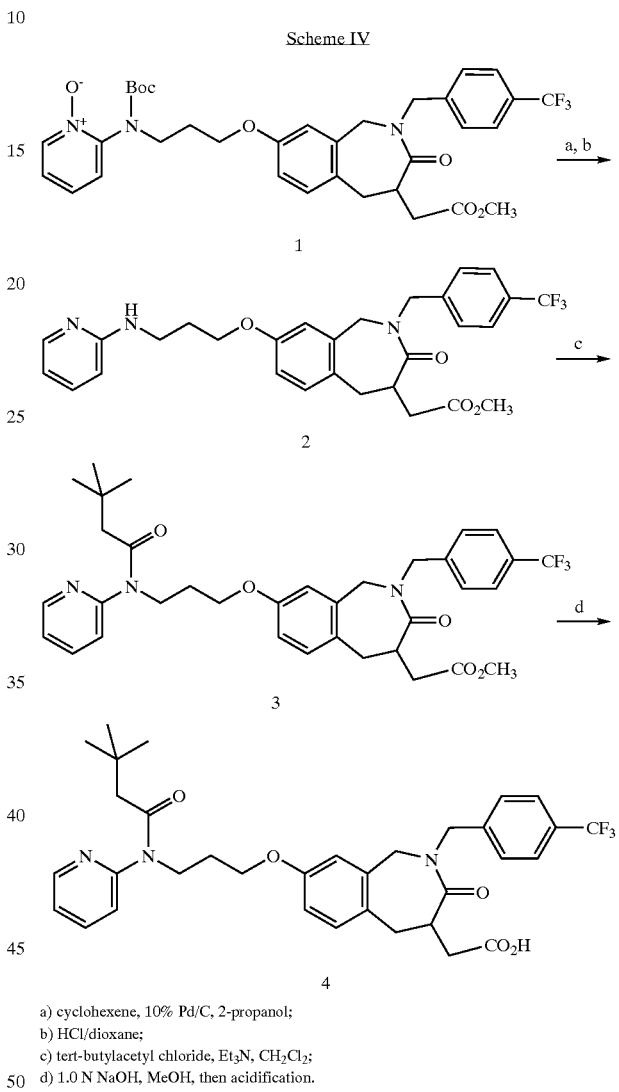

Scheme IV a) cyclohexene, 10% Pd/C, 2-propanol;
b) HCl/dioxane;
c) tert-butylacetyl chloride, Et$_3$N, CH$_2$Cl$_2$;
d) 1.0 N NaOH, MeOH, then acidification.

Compound IV-2, prepared from IV-1 by the procedures outlined in Schemes I-III, can be acylated at the nitrogen atom attached to the pyridine ring under standard acylation conditions well-known to those of skill in the art. For example, reaction of IV-2 with an acylating agent, for instance tert-butylacetyl chloride, in the presence of an appropriate acid scavenger, generally triethylamine, diisopropylethylamine, or pyridine, in a suitable solvent, oftentimes CH$_2$Cl$_2$, provides IV-3. Many additional methods for acylation of an amine are known, and can be found in standard reference books, such as "Compendium of Organic Synthetic Methods", Vol. I-VI (published by Wiley-Interscience). Saponification of IV-3 as described in Schemes I-III affords IV-4.

Compound III-2, prepared as described in Scheme I, can be alkylated simultaneously at both position 2 (benzazepine numbering) and on the nitrogen attached to the pyridine ring under standard alkylation conditions well-known to those of skill in the art. For example, III-2 can be treated with at least Scheme V

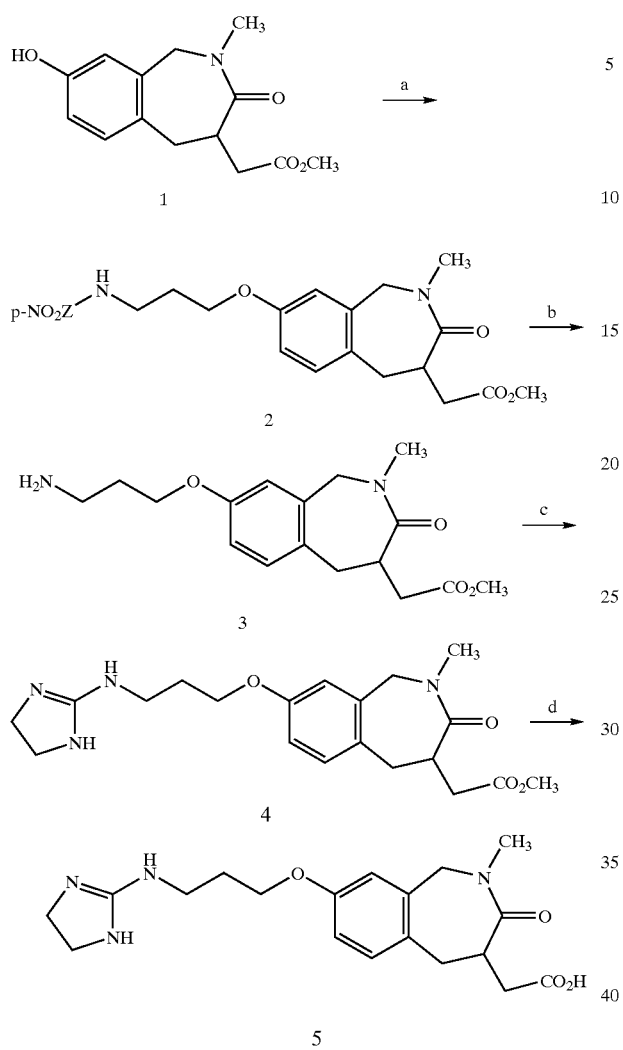

a) 3-(4-nitrobenzyloxycarbonylamino)-1-propanol, DEAD, (Ph)₃P, DMF, CH₂Cl₂;
b) H₂, Pd/C, EtOH;
c) 2-methylthio-2-imidazoline hydriodide, (i-Pr)₂NEt, dimethylacetamide, 100° C;
d) 1.0 N LiOH, THF, H₂O, then acidification.

Compound V-1, prepared as described in Scheme I, is reacted with a protected version of 3-amino-1-propanol, such as 3-(tert-butoxycarbonylamino)-1-propanol, 3-(benzyloxycarbonylamino)-1-propanol, or 3-(4-nitrobenzyloxycarbonylamino)-1-propanol, in a Mitsunobu-type coupling reaction as described in Scheme I. The resulting compound, V-2, is deprotected to afford V-3. As is well-known to those of skill in the art, deprotection conditions are selected based on the functionality and protecting group present in V-2. For example, the p-nitro-Cbz group present in V-2 is removed by hydrogenolysis in the presence of a palladium catalyst, generally palladium on charcoal or Pd(OH)₂ on charcoal, in an appropriate solvent, usually methanol, ethanol, ethyl acetate, or mixtures thereof. If desired, the hydrogenolysis can be conducted in the presence of an acid, for example HCl, to obtain the corresponding ammonium salt of V-2. Reaction of V-3 with 2-methylthio-2-imidazoline hydriodide in the presence of a base, for instance diisopropylethylamine, in a suitable solvent, such as MeOH, EtOH, DMF or dimethylacetamide, provides V-4. Similar conditions for effecting a related transformation are described in WO 95/32710. Saponification to afford V-5 is accomplished as described in Scheme I.

Scheme VI

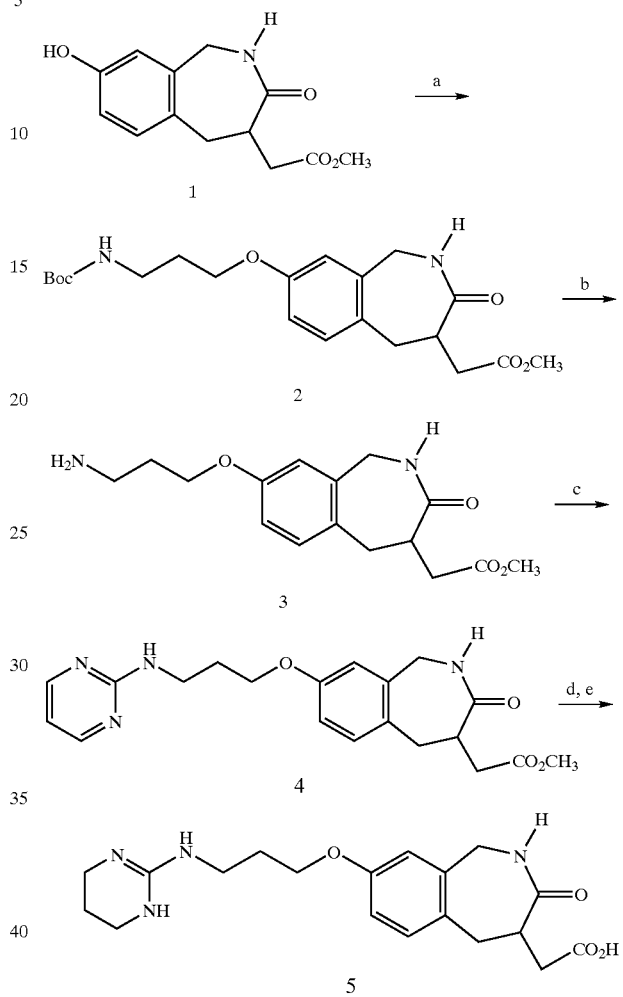

a) 3-(tert-butoxycarbonylamino)-1-propanol, DEAD, (Ph)₃P, DMF, THF;
b) TFA, CH₂Cl₂;
c) 2-bromopyrimidine, NaHCO₃, EtOH, reflux;
d) H₂, Pd/C, HCl, MeOH;
e) K₂CO₃, H₂O.

Compound VI-3, prepared from VI-1 by the procedure outlined in Scheme V, is reacted with a 2-halopyrimidine, generally 2-chloropyrimidine or 2-bromopyrimidine, in the presence of a suitable acid scavenger, usually sodium bicarbonate, triethylamine, diisopropylethylamine, or pyridine, in a suitable solvent, such as ethanol, DMF, or dimethylacetamide, to provide VI-4. The pyrimidine ring of VI-4 is reduced to the corresponding 1,4,5,6-tetrahydropyrimidine ring according to conditions reported for effecting such a transformation (see, for example, WO 95/32710). Thus, VI-4 is subjected to hydrogenation in the presence of a palladium catalyst, preferably palladium on activated carbon, in an appropriate solvent, such as methanol or ethanol. The reaction is usually conducted under acidic conditions; addition of a mineral acid such as HCl is generally preferable. VI-5 is obtained following basification of the filtered reaction mixture with K₂CO₃ and H₂O.

Scheme VII

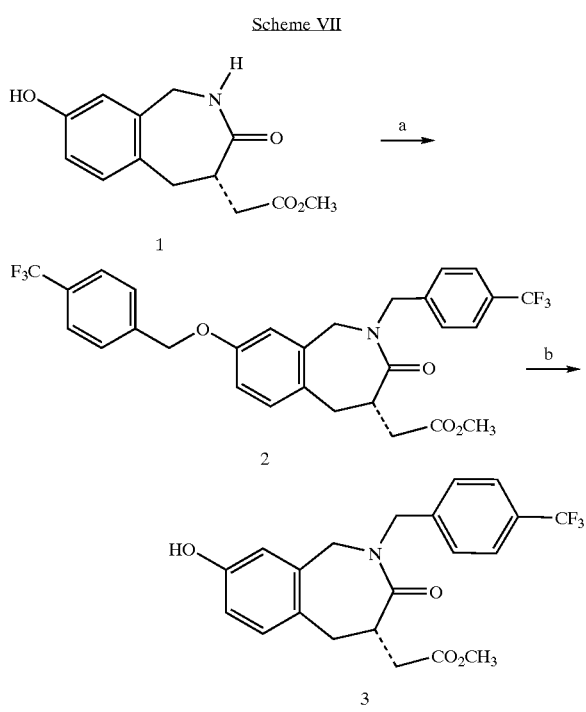

a) NaH, 4-(trifluoromethyl)benzyl bromide, DMF;
b) $H_2$, $Pd(OH)_2$/C, MeOH.

Compound VII-1, prepared by the general procedures described in Bondinell, et al., PCT application WO 93/00095, published Jan. 7, 1993 and Bondinell, et al., PCT application WO 94/14776, is reacted with 4-(trifluoromethyl)benzyl bromide in the presence of a suitable base, generally sodium hydride or lithium bis (trimethylsilyl)amide, in an aprotic solvent, preferably DMF, THF, or mixtures thereof, to afford the bis-alkylated product VII-2. The 4-(trifluoromethyl)benzyl ether of VII-2 can be conveniently removed by hydrogenolysis to provide the phenol VII-3. Methods for hydrogenolysis of benzyl ethers are well-known to those of skill in the art, and are described in appropriate reference volumes, for instance in Greene, "Protective Groups in Organic Synthesis" (published by Wiley-Interscience). The phenol of VII-3 is then used to prepare the formula (I) compounds using the methods described in the previous schemes.

Amide coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Coupling methods to form peptide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.*, 29, 984 (1986) and *J. Med. Chem.*, 30, 2291 (1987) are generally illustrative of the technique and are incorporated herein by reference.

Typically, the amine or aniline is coupled via its free amino group to an appropriate carboxylic acid substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran (THF), in the presence of a base, such as N-methyl morpholine, DMAP or a trialkylamine, with isobutyl chloroformate to form the "activated anhydride", which is subsequently reacted with the free amine of a second protected amino acid or aniline.

Useful intermediates for preparing formula (I) compounds in which $R^2$ is a benzimidazole are disclosed in Nestor et al, *J. Med. Chem.* 1984, 27, 320. Representative methods for preparing benzimidazole compounds useful as intermediates in the present invention are also common to the art and may be found, for instance, in EP-A 0 381 033.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidine, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds described herein are antagonists of the vitronectin receptor, and are useful for treating diseases wherein the underlying pathology is attributable to ligand or cell which interacts with the vitronectin receptor. For instance, these compounds are useful for the treatment of diseases wherein loss of the bone matrix creates pathology. Thus, the instant compounds are useful for the treatment of ostoeporosis, hyperparathyroidism, Paget's disease, hypercalcemia of malignancy, osteolytic lesions produced by bone metastasis, bone loss due to immobilization or sex hormone deficiency. The compounds of this invention are also believed to have utility as antitumor, anti-angiogenic, anti-inflammatory and anti-metastatic agents, and be useful in the treatment of atherosclerosis and restenosis.

The compound is administered either orally or parenterally to the patient, in a manner such that the concentration of drug is sufficient to inhibit bone resorption, or other such indication. The pharmaceutical composition containing the compound is administered at an oral dose of between about 0.1 to about 50 mg/kg in a manner consistent with the condition of the patient. Preferably the oral dose would be about 0.5 to about 20 mg/kg. For acute therapy, parenteral administration is preferred. An intravenous infusion of the peptide in 5% dextrose in water or normal saline, or a similar formulation with suitable excipients, is most effective, although an intramuscular bolus injection is also useful.

Typically, the parenteral dose will be about 0.01 to about 100 mg/kg; preferably between 0.1 and 20 mg/kg. The compounds are administered one to four times daily at a level to achieve a total daily dose of about 0.4 to about 400 mg/kg/day. The precise level and method by which the compounds are administered is readily determined by one routinely skilled in the art by comparing the blood level of the agent to the concentration required to have a therapeutic effect.

This invention further provides a method for treating osteoporosis or inhibiting bone loss which comprises administering stepwise or in physical combination a compound of formula (I) and other inhibitors of bone resorption, such as bisphosphonates (i.e., allendronate), hormone replacement therapy, anti-estrogens, or calcitonin. In addition, this invention provides a method of treatment using a compound of this invention and an anabolic agent, such as the bone morphogenic protein, iproflavone, useful in the prevention of bone loss and/or to increase bone mass.

Additionally, this invention provides a method of inhibiting tumor growth which comprises administering stepwise or in physical combination a compound of formula (I) and an antineoplastic agent. Compounds of the camptothecin analog class, such as topotecan, irinotecan and 9-aminocamptothecin, and platinum coordination complexes, such as cisplatin, ormaplatin and tetraplatin, are well known groups of antineoplastic agents. Compounds of the camptothecin analog class are described in U.S. Pat. Nos. 5,004,758, 4,604,463, 4,473,692, 4,545,880 4,342,776, 4,513,138, 4,399,276, EP Patent Application Publication Nos. 0 418 099 and 0 088 642, Wani, et al., *J. Med. Chem.*, 1986, 29, 2358, Wani, et al., *J. Med. Chem.*, 1980, 23, 554, Wani, et al., *J. Med. Chem.*, 1987, 30, 25 1774, and Nitta, et al., *Proc. 14th International Congr. Chemotherapy.*, 1985, *Anticancer Section* 1, 28, the entire disclosure of each which is hereby incorporated by reference. The platinum coordination complex, cisplatin, is available under the name Platinol® from Bristol Myers-Squibb Corporation. Useful formulations for cisplatin are described in U.S. Pat. Nos. 5,562,925 and 4,310,515, the entire disclosure of each which is hereby incorporated by reference.

In the method of inhibiting tumor growth which comprises administering stepwise or in physical combination a compound of formula (I) and an antineoplastic agent, the platinum coordination compound, for example cisplatin, can be administered using slow intravenous infusion. The preferred carrier is a dextrose/saline solution containing mannitol. The dose schedule of the platinum coordination compound may be on the basis of from about 1 to about 500 mg per square meter ($mg/m^2$) of body surface area per course of treatment. Infusion of the platinum coordination compound may be given one to two times weekly, and the weekly treatments may be repeated several times. Using a compound of the camptothecin analog class in a parenteral administration, the course of therapy generally employed is from about 0.1 to about 300.0 $mg/m^2$ of body surface area per day for about five consecutive days. Most preferably, the course of therapy employed for topotecan is from about 1.0 to about 2.0 $mg/m^2$ of body surface area per day for about five consecutive days. Preferably, the course of therapy is repeated at least once at about a seven day to about a twenty-eight day interval.

The pharmaceutical composition may be formulated with both the compound of formula (I) and the antineoplastic agent in the same container, but formualtion in different containers is preferred. When both agents are provided in solution form, they can be contained in an infusion/injection system for simultaneous administration or in a tandem arrangement.

For convenient administration of the compound of formula (I) and the antineoplastic agent at the same or different times, a kit is prepared, comprising, in a single container, such as a box, carton or other container, individual bottles, bags, vials or other containers each having an effective amount of the compound of formula (I) for parenteral administration, as described above, and an effective amount of the antineoplastic agent for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the antineoplastic agent and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the compound of formula (I) may be in an i.v. injectable form, or infusion bag linked in series, via tubing, to the antineoplastic agent in a second infusion bag. Using such a system, a patient can receive an initial bolus-type injection or infusion of the compound of formula (I) followed by an infusion of the antineoplastic agent.

The compounds may be tested in one of several biological assays to determine the concentration of compound which is required to have a given pharmacological effect.

Inhibition of Vitronectin Binding

Solid-Phase [$^3$H]-SK&F-107260 Binding to $\alpha_v\beta_3$: Human placenta or human platelet $\alpha_v\beta_3$ (0.1–0.3 mg/mL) in buffer T (containing 2 mM CaCl$_2$ and 1% octylglucoside) was diluted with buffer T containing 1 mM CaCl$_2$, 1 mM MnCl$_2$, 1 mM MgCl$_2$ (buffer A) and 0.05% NaN$_3$, and then immediately added to 96-well ELISA plates (Corning, New York, N.Y.) at 0.1 mL per well. 0.1–0.2 μg of $\alpha_v\beta_3$ was added per well. The plates were incubated overnight at 4° C. At the time of the experiment, the wells were washed once with buffer A and were incubated with 0.1 mL of 3.5% bovine serum albumin in the same buffer for 1 hr at room temperature. Following incubation the wells were aspirated completely and washed twice with 0.2 mL buffer A.

Compounds were dissolved in 100% DMSO to give a 2 mM stock solution, which was diluted with binding buffer (15 mM Tris-HCl (pH 7.4), 100 mM NaCl, 1 mM CaCl$_2$, 1 mM MnCl$_2$, 1 mM MgCl$_2$) to a final compound concentration of 100 μM. This solution is then diluted to the required final compound concentration. Various concentrations of unlabeled antagonists (0.001–100 μM) were added to the wells in triplicates, followed by the addition of 5.0 nM of [$^3$H]-SK&F-107260 (65–86 Ci/mmol).

The plates were incubated for 1 hr at room temperature. Following incubation the wells were aspirated completely and washed once with 0.2 mL of ice cold buffer A in a well-to-well fashion. The receptors were solubilized with 0.1 mL of 1% SDS and the bound [$^3$H]-SK&F-107260 was determined by liquid scintillation counting with the addition of 3 mL Ready Safe in a Beckman LS Liquid Scintillation Counter, with 40% efficiency. Nonspecific binding of [$^3$H]-SK&F-107260 was determined in the presence of 2 μM SK&F-107260 and was consistently less than 1% of total radioligand input. The IC$_{50}$ (concentration of the antagonist to inhibit 50% binding of [$^3$H]-SK&F-107260) was determined by a nonlinear, least squares curve-fitting routine, which was modified from the LUNDON-2 program. The K$_i$ (dissociation constant of the antagonist) was calculated according to the equation: $K_i=IC_{50}/(1+L/K_d)$, where L and K$_d$ were the concentration and the dissociation constant of [$^3$H]-SK&F-107260, respectively.

Compounds of the present invention inhibit vitronectin binding to SK&F 107260 in the concentration range of about 4.0 to about 0.0003 micomolar.

Compounds of this invention are also tested for in vitro and in vivo bone resorption in assays standard in the art for evaluating inhibition of bone formation, such as the pit formation assay disclosed in EP 528 587, which may also be performed using human osteoclasts in place of rat osteoclasts, and the ovarectomized rat model, described by Wronski et al., *Cells and Materials* 1991, Sup. 1, 69–74.

Vascular Smooth Muscle Cell Migration Assay

Rat or human aortic smooth muscle cells were used. The cell migration was monitored in a Transwell cell culture chamber by using a polycarbonate membrane with pores of 8 um (Costar). The lower surface of the filter was coated with vitronectin. Cells were suspended in DMEM supplemented with 0.2% bovine serum albumin at a concentration of 2.5–5.0×10$^6$ cells/mL, and were pretreated with test compound at various concentrations for 20 min at 20° C. The solvent alone was used as control. 0.2 mL of the cell suspension was placed in the upper compartment of the chamber. The lower compartment contained 0.6 mL of DMEM supplemented with 0.2% bovine serum albumin. Incubation was carried out at 37° C. in an atmosphere of 95% air/5% CO$_2$ for 24 hr. After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

Thyroparathyroidectomized Rat Model

Each experimental group consists of 5–6 adult male Sprague-Dawley rats (250–400 g body weight). The rats are thyroparathyroidectomized (by the vendor, Taconic Farms) 7 days prior to use. All rats receive a replacement dose of thyroxine every 3 days. On receipt of the rats, circulating ionized calcium levels are measured in whole blood immediately after it has been withdrawn by tail venipuncture into heparinized tubes. Rats are included if the ionized Ca level (measured with a Ciba-Corning model 634 calcium pH analyzer) is <1.2 mM/L. Each rat is fitted with an indwelling venous and arterial catheter for the delivery of test material and for blood sampling respectively. The rats are then put on a diet of calcium-free chow and deionized water. Baseline Ca levels are measured and each rat is administered either control vehicle or human parathyroid hormone 1–34 peptide (hPTH1–34, dose 1.25 ug/kg/h in saline/0.1% bovine serum albumin, Bachem, Ca) or a mixture of hPTH1–34 and test material, by continuous intravenous infusion via the venous catherer using an external syringe pump. The calcemic response of each rat is measured at two-hourly intervals during the infusion period of 6–8 hours.

Human Osteoclast Resorption and Adhesion Assays

Pit resorption and adhesion assays have been developed and standardized using normal human osteoclasts derived from osteoclastoma tissue. Assay 1 was developed for the measurement of osteoclast pit volumes by laser confocal microscopy. Assay 2 was developed as a higher throughput screen in which collagen fragments (released during resorption) are measured by competitive ELISA.

Assay 1 (Using Laser Confocal Microscopy)

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells.

A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

3 ml aliquots of the cell suspension (per compound treatment) are decanted into 15 ml centrifuge tubes. The cells are pelleted by centrifugation.

To each tube, 3 ml of the appropriate compound treatment are added (diluted to 50 uM in the EMEM medium). Also included are appropriate vehicle controls, a positive control (anti-vitronectin receptor murine monoclonal antibody [87MEM1] diluted to 100 ug/ml) and an isotype control ($IgG_{2a}$, diluted to 100 ug/ml). The samples are incubated at 37° C. for 30 mins.

0.5 ml aliquots of the cells are seeded onto sterile dentine slices in a 48-well plate and incubated at 37° C. for 2 hours. Each treatment is screened in quadruplicate.

The slices are washed in six changes of warm PBS (10 ml /well in a 6-well plate) and then placed into fresh medium containing the compound treatment or control samples. The samples are incubated at 37° C. for 48 hours.

Tartrate Resistant Acid Phosphatase (TRAP) Procedure (Selective Stain for Cells of the Osteoclast Lineage)

The bone slices containing the attached osteoclasts are washed in phosphate buffered saline and fixed in 2% gluteraldehyde (in 0.2M sodium cacodylate) for 5 mins.

They are then washed in water and are incubated for 4 minutes in TRAP buffer at 37° C. (0.5 mg/ml naphthol AS-BI phosphate dissolved in N,N-dimethylformamide and mixed with 0.25 M citrate buffer (pH 4.5), containing 10 mM sodium tartrate.

Following a wash in cold water the slices are immersed in cold acetate buffer (0.1 M, pH 6.2) containing 1 mg/ml fast red garnet and incubated at 4° C. for 4 minutes.

Excess buffer is aspirated, and the slices are air dried following a wash in water.

The TRAP positive osteoclasts (brick red/purple precipitate) are enumerated by bright-field microscopy and are then removed from the surface of the dentine by sonication.

Pit volumes are determined using the Nikon/Lasertec ILM21W confocal microscope.

Assay 2 (Using an ELISA Readout)

The human osteoclasts are enriched and prepared for compound screening as described in the initial 9 steps of Assay 1. For clarity, these steps are repeated hereinbelow.

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

In contrast to the method desribed above in Assay 1, the compounds are screened at 4 doses to obtain an $IC_{50}$, as outlined below:

The osteoclast preparations are preincubated for 30 minutes at 37° C. with test compound (4 doses) or controls.

They are then seeded onto bovine cortical bone slices in wells of a 48-well tissue culture plate and are incubated for a further 2 hours at 37° C.

The bone slices are washed in six changes of warm phosphate buffered saline (PBS), to remove non-adherent cells, and are then returned to wells of a 48 well plate containing fresh compound or controls.

The tissue culture plate is then incubated for 48 hours at 37° C.

The supernatants from each well are aspirated into individual tubes and are screened in a competitive ELISA that detects the c-telopeptide of type I collagen which is released during the resorption process. This is a commercially available ELISA (Osteometer, Denmark) that contains a rabbit antibody that specifically reacts with an 8-amino acid sequence (Glu-Lys-Ala-His-Asp-Gly-Gly-Arg) that is present in the carboxy-terminal telopeptide of the al-chain of type I collagen. The results are expressed as % inhibition of resorption compared to a vehicle control.

Human Osteoclast Adhesion Assay

The human osteoclasts are enriched and prepared for compound screening as described above in the initial 9 steps of Assay 1. For clarity, these steps are repeated hereinbelow.

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

Osteoclastoma-derived osteoclasts are preincubated with compound (4 doses) or controls at 37° C. for 30 minutes.

The cells are then seeded onto osteopontin-coated slides (human or rat osteopontin, 2.5 ug/ml) and incubated for 2 hours at 37° C.

Non adherent cells are removed by washing the slides vigorously in phosphate buffered saline and the cells remaining on the slides are fixed in acetone.

The osteoclasts are stained for tartrate-resistant acid phosphatase (TRAP), a selective marker for cells of this phenotype (see steps 15–17), and are enumerated by light microscopy. The results are expressed as % inhibition of adhesion compared to a vehicle control.

Cell Adhesion Assay

Cells and Cell Culture

Human embryonic kidney cells (HEK293 cells) were obtained from ATCC (Catalog No. CRL 1573). Cells were grown in Earl's minimal essential medium (EMEM) medium containing Earl's salts, 10% fetal bovine serum, 1% glutamine and 1% Penicillin-Steptomycin.

Constructs and Transfections

A 3.2 kb EcoRI-KpnI fragment of the av subunit and a 2.4 kb XbaI-XhoI fragment of the $\beta_3$ subunit were inserted into the EcoRI-EcoRV cloning sites of the pCDN vector (Aiyar et al., 1994) which contains a CMV promoter and a G418 selectable marker by blunt end ligation. For stable expression, 80×10$^6$ HEK 293 cells were electrotransformed with $\alpha_v$+$\beta_3$ constructs (20 $\mu$g DNA of each subunit) using a Gene Pulser (Hensley et al., 1994) and plated in 100 mm plates (5×10$^5$ cells/plate). After 48 hr, the growth medium was supplemented with 450 $\mu$g/mL Geneticin (G418 Sulfate, GIBCO-BRL, Bethesda, Md.). The cells were maintained in selection medium until the colonies were large enough to be assayed.

Immunocytochemical Analysis of Transfected Cells

To determine whether the HEK 293 transfectants expressed the vitronectin receptor, the cells were immobilized on glass microscope slides by centrifugation, fixed in acetone for 2 min at room temperature and air dried. Specific reactivity with 23C6, a monoclonal antibody specific for the $\alpha_v\beta_3$ complex was demonstrated using a standard indirect immunofluorescence method.

Cell Adhesion Studies

Corning 96-well ELISA plates were precoated overnight at 4° C. with 0.1 mL of human vitronectin (0.2 $\mu$g/mL in RPMI medium). At the time of the experiment, the plates were washed once with RPMI medium and blocked with 3.5% BSA in RPMI medium for 1 hr at room temperature. Transfected 293 cells were resuspended in RPMI medium, supplemented with 20 mM Hepes, pH 7.4 and 0.1% BSA at a density of 0.5×10$^6$ cells/mL. 0.1 mL of cell suspension was added to each well and incubated for 1 hr at 37° C., in the presence or absence of various $\alpha_v\beta_3$ antagonists. Following incubation, 0.025 mL of a 10% formaldehyde solution, pH 7.4, was added and the cells were fixed at room temperature for 10 min. The plates were washed 3 times with 0.2 mL of RPMI medium and the adherent cells were stained with 0.1 mL of 0.5% toluidine blue for 20 min at room temperature. Excess stain was removed by extensive washing with deionized water. The toluidine blue incorporated into cells was eluted by the addition of 0.1 mL of 50% ethanol containing 50 mM HCl. Cell adhesion was quantitated at an optical density of 600 nm on a microtiter plate reader (Titertek Multiskan MC, Sterling, Va.).

Solid-Phase $\alpha_v\beta_5$ Binding Assay:

The vitronectin receptor $\alpha_v\beta_5$ was purified from human placenta. Receptor preparation was diluted with 50 mM Tris-HCl, pH 7.5, 100 mM NaCl, 1 mM CaCl$_2$, 1 mM MnCl$_2$, 1 mM MgCl$_2$ (buffer A) and was immediately added to 96-well ELISA plates at 0.1 ml per well. 0.1–0.2 $\mu$g of $\alpha_v\beta_3$ was added per well. The plates were incubated overnight at 4° C. At the time of the experiment, the wells were washed once with buffer A and were incubated with 0.1 ml of 3.5% bovine serum albumin in the same buffer for 1 hr at room temperature. Following incubation the wells were aspirated completely and washed twice with 0.2 ml buffer A.

In a [$^3$H]-SK&F-107260 competition assay, various concentrations of unlabeled antagonists (0.001–100 $\mu$M) were added to the wells, followed by the addition of 5.0 nM of [$^3$H]-SK&F-107260. The plates were incubated for 1 hr at room temperature. Following incubation the wells were aspirated completely and washed once with 0.2 ml of ice cold buffer A in a well-to-well fashion. The receptors were solubilized with 0.1 ml of 1% SDS and the bound [$^3$H]-SK&F-107260 was determined by liquid scintillation counting with the addition of 3 ml Ready Safe in a Beckman LS 6800 Liquid Scintillation Counter, with 40% efficiency. Nonspecific binding of [$^3$H]-SK&F-107260 was determined in the presence of 2 $\mu$M SK&F-107260 and was consistently less than 1% of total radioligand input. The IC$_{50}$ (concentration of the antagonist to inhibit 50% binding of [$^3$H]-SK&F-107260) was determined by a nonlinear, least squares curve-fitting routine, which was modified from the LUNDON-2 program. The K$_i$ (dissociation constant of the antagonist) was calculated according to Cheng and Prusoff equation: $K_i = IC_{50}/(1+L/K_d)$, where L and K$_d$ were the concentration and the dissociation constant of [$^3$H]-SK&F-107260, respectively.

Inhibition of RGD-Mediated GPIIb-IIIa Binding

Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM CaCl$_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM CaCl$_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.
Incorporation of GPIIb-IIIa in Liposomes.

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70° C. until needed.
Competitive Binding to GPIIb-IIIa The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 $\mu$g/mL polylysine (Sigma Chemical Co., St. Louis, Mo.) at room temperature for 1 h to block nonspecific binding. Various concentrations of unlabeled benzazepines were added to the wells in quadruplicate. [$^3$H]-SK&F-107260 was applied to each well at a final concentration of 4.5 nM, followed by the addition of 1 $\mu$g of the purified platelet GPIIb-IIIa-containing liposomes. The mixtures were incubated for 1 h at room temperature. The GPIIb-IIIa-bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 $\mu$M unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: Ki=IC50/(1+L/Kd), where L is the concentration of [3H]SK&F-107260 used in the competitive binding assay (4.5 nM), and Kd is the dissociation constant of [3H]-SK&F-107260 which is 4.5 nM as determined by Scatchard analysis.

Preferred compounds of this invention have an affinity for the vitronectin receptor relative to the fibrinogen receptor of greater than 10:1. Most preferred compounds have a ratio of activity of greater than 100:1.

The efficacy of the compounds of formula (I) alone or in combination with an antineoplastic agent may be determined using several transplantable mouse tumor models. See U.S. Pat. Nos. 5,004,758 and 5,633,016 for details of these models The examples which follow are intended in no way to limit the scope of this invention, but are provided to illustrate how to make and use the compounds of this invention. Many other embodiments will be readily apparent to those skilled in the art.

EXAMPLES

General $^1$H nuclear magnetic resonance (NMR) spectra were recorded at either 250 or 400 MHz. Chemical shifts are reported in parts per million (d) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Infrared (IR) spectra were recorded in transmission mode, and band positions are reported in inverse wavenumbers (cm$^{-1}$). Mass spectra were obtained using electrospray (ES) or FAB ionization techniques. Elemental analyses were performed either in-house or by Quantitative Technologies Inc., Whitehouse, N.J. Melting points were taken on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs. ODS refers to an octadecylsilyl derivatized silica gel chromatographic support. 5$\mu$ Apex-ODS indicates an octadecylsilyl derivatized silica gel chromatographic support having a nominal particle size of 5$\mu$, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

Preparation of methyl (±)-8-hydroxy-3-oxo-2,3,4,5-tetrahydro-1H-2-benzazepine-4-acetate a) 4-Bromo-3-bromomethylanisole A mixture of 2-bromo-5-methoxytoluene (20 g, 0.10 mol), N-bromosuccinimide (19.6 g, 0.11 mol), benzoyl peroxide (1 g, 4 mmol), and methylene chloride (200 mL) was irradiated for 18 hr with a flood lamp to effect gentle reflux. The mixture was then cooled to −10° C. for several hours and the solution was decanted away from the precipitated succinimide. The solution was concentrated and the residue was crystallized from chloroform/hexane to give the title compound (19.7 g, 70%) as pale yellow prisms: $^1$H NMR (CDCl$_3$) δ 7.45 (d, J=8.9 Hz, 1 H, 6.99 (d, J=3 Hz, 1 H, 6.74 (dd, J=8.9, 3 Hz, 1 H), 4.55 (s, 2 H) 3.80 (s, 3 H).

b) 3-Bis(tert-butoxycarbonyl)aminomethyl-4-bromoanisole

A mixture of 4-bromo-3-bromomethylanisole (24 g, 86 mmol) and potassium di-tert-butyl iminodicarboxylate (24 g, 94 mmol) in dimethylformamide (200 mL) was stirred under argon at room temperature for 18 hr. The reaction was then concentrated under vacuum and the residue was partitioned between ethyl acetate and water. The organic phase was washed with water and brine, dried(MgSO$_4$), and concentrated. The residue was recrystallized from hexane to give the title compound (15 g, 42%) as a white solid: $^1$H NMR (CDCl$_3$) δ 7.40 (d, J=8.6 Hz, 1 H), 6.68 (m, 2 H), 4.81(s, 2 H), 3.74 (s, 3 H) 1.44 (s, 18 H).

c) Methyl (±)-3-carbomethoxy-4-[2-bis(tert-butoxycarbonyl)aminomethyl-4-methoxyphenyl]-3-butenoate A 500 mL flask was charged with 3-bis(tert-butoxycarbonyl)aminomethyl-4-bromoanisole(15 g, 36 mmol), dimethyl itaconate (7.5 g, 47 mmol), tri-o-tolylphosphine (1 g, 3 mol), palladium acetate (0.4 g, 2 mmol), diisopropylethylamine (12.8 mL, 72 mmol), and propionitrile (150 mL). The mixture was purged with argon (several evacuation/argon flush cycles), then was heated to reflux under argon for 1 hr. The reaction was allowed to cool to RT, then was poured into ice-cold ethyl ether (500 mL). The resulting precipitate was removed by filtration and the filtrate was concentrated. The residue was purified by chromatography on silica gel (10%–20% ethyl acetate in hexane) to give the title compound (11.8 g, 66%) as a pale yellow oil: $^1$H NMR (CDCl$_3$) δ 7.94 (s, 1 H, 7.15 (d, J=8.1 Hz, 1 H), 6.77 (d, J=8.1 Hz, 1 H, 6.76 (s, 1 H, 4.73 (s, 2 H), 3.81 (s, 3 H), 3.79 (s, 3 H), 3.71 (s, 3 H), 3.38 (s, 2 H), 1.45 (s, 18 H).

d) Methyl (±)-3-carbomethoxy-4-[2-bis(tert-butoxycarbonyl)aminomethyl-4-methoxyphenyl]butanoate A pressure vessel charged with methyl (±)-3-carbomethoxy-4-[2-bis(tert-butoxycarbonyl)aminomethyl-4-methoxyphenyl]-3-butenote (11.8 g), ethyl acetate (120 mL), and 10% palladium on charcoal (1 g) was shaken under 45 psi of hydrogen for 18 hr. The mixture was then filtered and the filtrate was concentrated to give the title compound (12 g, 100%) as a colorless oil: $^1$H NMR (CDCl$_3$) δ 7.00 (d, J=8.2 Hz, 1 H, 6.71 (m, 2 H), 4.81 (s, 2 H), 3.75 (s, 3 H), 3.66 (s,3 H), 3.63 (s, 3 H), 3.05 (m, 2 H), 2.73 (m, 2 H), 2.42 (dd, J=16.0, 4.8 Hz, 1 H, 1.44 (s, 18 H).

e) Methyl (±)-3-carbomethoxy-4-[2-(aminomethyl)-4-methoxyphenyl]butanoate

A solution of methyl (±)-3-carbomethoxy-4-[2-bis(tert-butoxycarbonyl)aminomethyl-4-methoxyphenyl]butanoate (12 g) in chloroform (100 mL) and trifluoroacetic acid (50 mL) was stirred under argon at room temperature for 4 hr. The solution was then concentrated under vacuum to give the title compound (10 g, 100%) as a viscous oil: MS (ES) m/e 296.2 (M+H)$^+$.

f) Methyl (±)-8-methoxy-3-oxo-2,3,4,5-tetrahydro-1H-2-benzazepine-4-acetate

A solution of methyl (±)-3-carbomethoxy-4-[2-(aminomethyl)-4-methoxyphenyl]butanoate (10 g, 24 mmol) and triethylamine (17 mL, 120 mmol) in toluene (100 mL) was heated at reflux for 18 hr. The reaction was then concentrated and the residue was partitioned between ethyl acetate and water. The aqueous layer was extracted twice with ethyl acetate and the combined organic extracts were washed with brine, dried (MgSO$_4$), and concentrated to afford the title compound (4.8 g, 76%) as tan solid: MS (ES) m/e 264.2 (M+H)$^+$.

g) Methyl (±)-8-hydroxy-3-oxo-2,3,4,5-tetrahydro-1H-2-benzazepine-4-acetate

Anhydrous aluminum chloride (7.6 g, 57 mmol) was added portionwise to a stirred solution of methyl (±)-8-methoxy-3-oxo-2,3,4,5-tetrahydro-1H-2-benzazepine-4-acetate (3.0 g, 11 mmol) and ethanethiol (4.2 mL, 57 mmol) in methylene chloride (100 mL) at 0° C. under argon. The resulting mixture was allowed to warm to room temperature and stir overnight, then was concentrated. The residue was triturated with ice-water, and the resulting solid was collected by filtration and dried to give the title compound (2.64 g, 91%) as an off-white solid: MS (ES) m/e 250.2 (M+H)$^+$.

Preparation 2

Preparation of methyl (±)-8-hydroxy-2-methyl-3-oxo-2,3,4,5-tetrahydro-1H-2-benzazepine-4-acetate a) 3-[N-(tert-Butoxycarbonyl)-N-methylamino]methyl-4-bromoanisole 40% aqueous methylamine (49 mL, 563 mmole) was added rapidly to a solution of 4-bromo-3-bromomethylanisole (15.76 g, 56.29 mmole) in THF (280 mL) at RT. After 2.5 hr, the reaction was concentrated, and the residue was partitioned between Et$_2$O (560 mL) and 1.0 N NaOH (100 mL). The layers were separated, and the organic layer was dried (MgSO$_4$) and concentrated to a yellow oil: TLC (5% MeOH/CHCl$_3$) R$_f$ 0.32.

The oil was dissolved in CHCl$_3$ (280 mL), and di-tert-butyl dicarbonate (1.29 g, 56.29 mmole) was added. The reaction was stirred at RT for 45 min, then was concentrated. Silica gel chromatography (5% EtOAc/toluene) gave the title compound (16.81 g, 90%) as a light yellow oil: TLC (5% EtOAc/toluene) R$_f$ 0.43; $^1$H NMR (400, CDCl$_3$) mixture of rotamers; δ 7.42 (d, J=8.7 Hz, 1 H, 6.65–6.80 (m, 2 H), 4.40–4.55 (m, 2 H), 3.77 (s, 3 H), 2.81–2.97 (m, 3 H), 1.37–1.60 (m, 9 H); MS (ES) m/e 352/354 (M+Na)$^+$.

b) Methyl (±)-3-carbomethoxy-4-[2-[N-(tert-butoxycarbonyl)-N-methylamino]methyl-4-methoxypheny]butanoate A solution of 3-[N-(tert-butoxycarbonyl)-N-methylamino]methyl-4-bromoanisole (4.95 g, 15 mmol), dimethyl itaconate (3.08 g, 19.5 mmol), palladium acetate (168 mg, 0.75 mmol), tri-o-tolylphosphine (457 mg, 1.5 mol), and diisopropylethylamine (5.2 mL, 30 mmol) in propionitrile (75 mL) was heated to reflux for 45 min, then was concentrated on the rotavap. The residue was diluted with Et$_2$O (150 mL), and the mixture was filtered through celite® to remove insoluble materials. The filtrate was concentrated, and the residue was reconcentrated from xylenes. Chromatography on silica gel (gradient: 20% EtOAc/hexanes, then 1:1 EtOAc/hexanes) removed the phosphine and baseline materials; all other materials with R$_f$ 0.40–0.70 were collected together and concentrated to leave a cloudy, yellow oil: TLC (30% EtOAc/hexanes) R$_f$ 0.41 (major product).

The oil was dissolved in MeOH (75 mL), and 10% Pd/C was added carefully. The mixture was shaken under hydrogen (50 psi) for 2.5 hr, then was filtered through celite® to remove the catalyst. The filtrate was concentrated, and the residue was resubmitted to the reaction conditions. After another 2.5 hr, the mixture was filtered through celite® to remove the catalyst, and the filtrate was concentrated to leave a light yellow oil. This was reconcentrated from CHCl$_3$/hexanes, then was chromatographed on silica gel (gradient: 20% EtOAc/hexanes, then 1:1 EtOAc/hexanes) to afford the title compound (4.53 g, 74%) as a light yellow oil: TLC (30% EtOAc/toluene) R$_f$ 0.46; $^1$H NMR (400, CDCl$_3$) mixture of rotamers; δ 7.03 (d, J=8.2 Hz, 1 H, 6.65–6.80 (m, 2 H), 4.46 (br s, 2 H), 3.77 (s, 3 H), 3.64 (s, 3 H), 3.63 (s, 3 H), 2.62–3.12 (m, 7 H), 2.35–2.50 (m, 1 H, 1.47 (br s, 9 H); MS (ES) m/e 432 (M+Na)$^+$.

c) Methyl (±)-3-carbomethoxy-4-[2-(methylamino)methyl-4-methoxyphenyl]butanoate

TFA (55 mL) was added all at once to a solution of methyl (±)-3-carbomethoxy-4-[2-[N-(tert-butoxycarbonyl)-N-(methylamino]methyl-4-methoxyphenyl]butanoate (4.53 g, 11.06 mmole) in anhydrous CH$_2$Cl$_2$ (55 mL) at 0° C., and the reaction was warmed to RT. After 1 hr, the reaction was concentrated, and the residue was reconcentrated from toluene (2×100 mL) to leave the title compound (11.06 mmole, quantitative) as a light yellow oil: MS (ES) m/e 310 (M+H)$^+$.

d) Methyl (±)-8-methoxy-2-methyl-3-oxo-2,3,4,5-tetrahydro-1H-2-benzazepine-4-acetate A solution of methyl (±)-3-carbomethoxy-4-[2-(methylamino)methyl-4-methoxyphenyl]butanoate (11.06 mmole) and diisopropylethylamine (5.8 mL, 33.18 mmole) in toluene (110 mL) was heated at reflux for 25 hr, stirred at RT for 4 days, then heated at reflux for another 24 hr. Concentration and silica gel chromatography (5% MeOH in 1:1 EtOAc/CHCl$_3$) gave the title compound (2.88 g, 94%) as a light yellow solid: TLC (5% MeOH in 1:1 EtOAc/CHCl$_3$) R$_f$ 0.63; $^1$H NMR (250, CDCl$_3$) δ 7.02 (d, J=8.4 Hz, 1 H, 6.78 (dd, J=8.4, 2.7 Hz, 1 H), 6.63 (d, J=2.7 Hz, 1 H), 5.29 (d, J=16.3 Hz, 1 H), 3.50–3.90 (m, 2 H), 3.79 (s, 3 H), 3.71 (s, 3 H), 2.73–3.16 (m, 3 H), 3.04 (s, 3 H), 2.41 (dd, J=16.7, 5.4 Hz, 1 H; MS (ES) m/e 300 (M+Na)$^+$, 278 (M+H)$^+$.

e) Methyl (±)-8-hydroxy-2-methyl-3-oxo-2,3,4,5-tetrahydro-1H-2-benzazepine-4-acetate Anhydrous aluminum chloride (1.35 g, 10.15 mmole) was added all at once to a solution of methyl (±)-8-methoxy-2-methyl-3-oxo-2,3,4,5-tetrahydro-1H-2-benzazepine-4-acetate (562 mg, 2.03 mmole) and ethanethiol (0.75 mL, 10.15 mmole) in anhydrous CH$_2$Cl$_2$ (20 mL) at 0° C. under argon. The mixture was warmed to RT and stirred for 4.5 hr, then was recooled to 0° C. Ice cold H$_2$O (20 mL) was added, and the mixture was stirred briskly for 5 min, then was extracted with CHCl$_3$ (3×20 mL). The combined CHCl$_3$ layers were dried (MgSO$_4$) and concentrated to leave a residue. The aqueous layer was suction filtered to collect a solid precipitate. This precipitate and the residue from the CHCl$_3$ layer were combined in 1:1 MeOH/CHCl$_3$, and the solution was concentrated to leave an off-white solid. This was triturated with hot MeOH, and the mixture was allowed to cool to RT. The solid was collected by suction filtration and washed sequentially with cold MeOH and Et$_2$O. Drying in high vacuum at 40° C. gave the title compound (467.9 mg, 88%) as a colorless solid: TLC (5% MeOH/CHCl$_3$) R$_f$ 0.17; $^1$H NMR (250, DMSO-d$_6$) δ 9.29(s, 1 H), 6.89 (d, J=8.1 Hz, 1 H), 6.50–6.70 (m, 2 H), 5.16 (d, J=16.4 Hz, 1 H), 3.84 (d, J=16.4 Hz, 1 H), 3.60–3.85 (m, 1 H), 3.56 (s, 3 H), 2.30–3.00 (m, 4 H), 2.86 (s, 3 H); MS (ES) m/e 286 (M+Na)$^+$, 264 (M+H)$^+$.

Preparation 3
Preparation of 2-[(3-hydroxy-1-propyl)amino]pyridine-N-oxide a) 2-[(3-Hydroxy-1-propyl)amino]pyridine-N-oxide A mixture of 2-chloropyridine-N-oxide (16.6 g, 0.1 mole), 3-amino-1-propanol (15.3 mL, 0.2 mole), NaHCO$_3$ (42 g, 0.5 mole), and tert-amyl alcohol (100 mL) was heated to reflux. After 21 hr, the reaction was cooled, diluted with CH$_2$Cl$_2$ (300 mL), and suction filtered to remove insoluble materials. The filtrate was concentrated and reconcentrated from toluene to leave a yellow oil. Silica gel chromatography (20% MeOH/CHCl$_3$) gave the title compound (15.62 g, 93%) as a yellow solid: TLC (20% MeOH/CHCl$_3$) R$_f$ 0.48; $^1$H NMR (250, CDCl$_3$) δ 8.07 (dd, J=6.6, 1.2 Hz, 1 H), 7.34 (br t, 1 H, 7.10–7.30 (m, 1 H), 6.64 (dd, J=8.5, 1.4 Hz, 1 H), 6.40–6.60 (m, 1 H), 4.49 (br s, 1 H), 3.65–3.90 (m, 2 H), 3.35–3.60 (m, 2 H), 1.75–2.00 (m, 2 H); MS (ES) m/e 169 (M+H)$^+$.

Preparation 4
Preparation of 2-[(3-hydroxy-1-propyl)amino]-4-nitropyridine-N-oxide a) 2-[(3-Hydroxy-1-propyl)amino]-4-nitropyridine-N-oxide According to the procedure of Preparation 3, except substituting 2-chloro-4-nitropyridine-N-oxide (see Jain, P. C.; Chatterjee, S. K.; Anand, N. *Indian Journal of Chemistry* 1966, 403) for the 2-chloropyridine-N-oxide hydrochloride, the title compound was prepared as an orange solid: MS (ES) m/e 214.2 (M+H)$^+$.

Preparation 5
Preparation of 2-[(3-hydroxy-1-propyl)amino]-4-methoxypyridine-N-oxide a) 2-[(3-Hydroxy-1-propyl)amino]-4-methoxypyridine-N-oxide A solution of 2-[(3-hydroxy-1-propyl)amino]-4-nitropyridine-N-oxide (0.275 g, 1 mmol) and 0.5 M NaOMe in MeOH (16 mL, 8 mmol) was heated at reflux under argon for 3 hr. The reaction was then allowed to cool, and glacial AcOH (0.5 mL, 8 mmol) was added. The solution was concentrated to dryness and the residue was triturated with CH$_2$Cl$_2$. The insoluble materials were removed by filtration and the filtrate was concentrated. Silica gel chromatography (5–15% MeOH/CH$_2$Cl$_2$) gave the title compound (0.23 g, 90%) as a colorless oil: MS (ES) m/e 199.0 (M+H)$^+$.

Preparation 6
Preparation of (±)-8-hydroxy-3-oxo-2-(2,2,2-trifluoroethyl)-2,3,4,5-tetrahydro-1H-2-benzazepine-4-acetate a) 3-[N-(tert-Butoxycarbonyl)-N-(2,2,2-trifluoroethyl)amino]methyl-4-bromoanisole 2,2,2-Trifluoroethylamine (4.9 mL, 62.5 mmole) was added rapidly to a solution of 4-bromo-3-bromomethylanisole (7.00 g, 25 mmole) in an hydrous DMSO (25 mL) at RT. The reaction warmed to approximately 30–35 ° C. After 2 hr, the reaction was diluted with ice-cold 0.5 N NaOH (100 mL) and extracted with Et$_2$O (3×100 mL). The combined Et$_2$O layers were washed sequentially with H$_2$O (2×25 mL) and brine (25 mL), dried (MgSO$_4$), and concentrated to a light yellow oil: TLC (toluene) R$_f$ 0.43.

The oil was dissolved in anhydrous CH$_2$Cl$_2$ (48 mL) in a roundbottom flask, and di-tert-butyl dicarbonate (10.48 g, 48.04 mmole) was added. The flask containing the reaction solution was placed on the rotavap and rotated in vacuum at 50° C. for 16 hr. The resulting residue was diluted with hexanes (100 mL) and the solution was seeded with a small amount of the pure, solid product (obtained from a previous experiment by silica gel chromatography using 10% EtOAc/hexanes as eluent). The mixture was allowed to stand at RT for several hr, then was placed in the refrigerator overnight. The product was collected by suction filtration and washed with hexanes. Drying in vacuum gave the title compound (7.19 g, 75%) as a colorless solid. The mother liquors were concentrated and chromatographed on silica gel (10% EtOAc/hexanes) to afford additional title compound (1.42 g; total=8.61 g, 90%): TLC (10% EtOAc/toluene) R$_f$ 0.48; mp 86–89° C.; $^1$H NMR (250, CDCl$_3$) δ 7.44 (d, J=9.0 Hz, 1 H), 6.64–6.82 (m, 2 H), 4.52–4.70 (m, 2 H), 3.61–4.00 (m, 2 H), 3.77 (s, 3 H), 1.22–1.68 (m, 9 H).

b) Methyl (±)-3-carbomethoxy-4-[2-[N-(tert-butoxycarbonyl)-N-(2,2,2-trifluoroethyl)amino]methyl-4-methoxyphenyl]butanoate A solution of 3-[N-(tert-butoxycarbonyl)-N-(2,2,2-trifluoroethyl)amino]methyl-4-bromoanisole (9.17 g, 23.03 mmol), dimethyl itaconate (4.73 g, 29.94 mmol), palladium acetate (259 mg, 1.15 mmol), tri-o-tolylphosphine (701 mg, 2.30 mol), and diisopropylethylamine (8.0 mL, 46.06 mmol) in propionitrile (115 mL) was deoxygenated (3× evacuation/argon purge cycles), then was heated to reflux under argon. After 2 hr the reaction was concentrated and reconcentrated from toluene. Silica gel chromatography (30% EtOAc/hexanes, load sample with $CH_2Cl_2$) removed the phosphine and baseline materials; all other materials with $R_f$ 0.55–0.70 were collected together and concentrated to leave a yellow oil. This was taken up in 20% EtOAc/hexanes (200 mL) and allowed to stand at RT for 1 hr then in the refrigerator overnight. The mixture was filtered to remove a yellow precipitate, and the filtrate was concentrated to leave 9.93 g (91%) of a yellow oil: TLC (30% EtOAc/hexanes) $R_f$ 0.55 (major product).

The oil was dissolved in EtOAc (100 mL), and 10% Pd/C (4.44 g, 4.18 mmole) was added. The mixture was shaken under hydrogen (50 psi) for 3.5 hr, then was filtered through celite® to remove the catalyst. The filtrate was concentrated, and the residue was chromatographed on silica gel (gradient: 20% EtOAc/hexanes) to afford the title compound (7.98 g, 73% for two steps) as a colorless oil: TLC (20% EtOAc/toluene) $R_f$ 0.35; $^1$H NMR (250, $CDCl_3$) δ 7.05 (d, J=8.4 Hz, 1 H), 6.76 (dd, J=8.4, 2 7 Hz, 1 H), 6.60–6.72 (m, 1 H), 4.50–4.80 (m, 2 H), 3.45–3.95 (m, 2 H), 3.77 (s, 3 H), 3.63 (s, 6 H), 2.85–3.09 (m, 2 H), 2.58–2.80 (m, 2 H), 2.33–2.50 (m, 1 H), 1.20–1.70 (m 9 H); MS (ES) m/e 5.00 (M+Na)$^+$.

c) Methyl (±)-3-carbomethoxy-4-[2-(2,2,2-trifluoroethylamino)methyl-4-methoxyphenyl]butanoate TFA (55 mL) was added all at once to a solution of methyl (±)-3-carbomethoxy-4-[2-[N-(tert-butoxycarbonyl)-N-(2,2,2-trifluoroethyl)amino]methyl-4-methoxyphenyl]butanoate (7.98 g, 16.71 mmole) in anhydrous $CH_2Cl_2$ (42 mL) at 0° C. under argon, and the reaction was warmed to RT. After 1.5 hr, the reaction was concentrated, and the residue was reconcentrated from xylenes. Drying in high vacuum at 40° C. left the title compound (8.70 g, quantitative) as a yellow solid: MS (ES) m/e 378 (M+H)$^+$.

d) Methyl (±)-8-methoxy-3-oxo-2-(2,2,2-trifluoroethyl)-2,3,4,5-tetrahydro-1H-2-benzazepine-4-acetate A mixture of methyl (±)-3-carbomethoxy-4-[2-(2,2,2-trifluoroethylamino)methyl-4-methoxyphenyl]butanoate (16.71 mmole), tripropylamine (9.5 mL, 50.13 mmole), and xylenes (170 mL) was heated at reflux. After 63 hr the reaction was concentrated, and the residue was chromatographed on silica (2:1 EtOAc/hexanes, load with $CH_2Cl_2$). The title compound (5.33 g, 92% for two steps) was obtained as a light yellow solid: TLC (40% EtOAc/hexanes) $R_f$ 0.49; $^1$H NMR (250, $CDCl_3$) δ 7.04 (d, J=8.5 Hz, 1 H), 6.80 (dd, J=8.5, 2.6 Hz, 1 H), 6.61 (d, J=2.6 Hz, 1 H), 5.35 (d, J=16.8 Hz, 1 H), 3.60–4.30 (m, 4 H), 3.79 (s, 3 H), 3.71 (s, 3 H), 2.81–3.15 (m, 3 H), 2.46 (dd, J=16.9, 5.5 Hz, 1 H); MS (ES) m/e 368 (M+Na)$^+$, 346 (M+H)$^+$.

e) Methyl (±)-8-hydroxy-2-methyl-3-oxo-2,3,4,5-tetrahydro-1H-2-benzazepine-4-acetate A solution of $BBr_3$ in $CH_2Cl_2$ (1.0 M, 60 mL, 60 mmole) was added dropwise over 30 min to a solution of methyl (±)-8-methoxy-3-oxo-2-(2,2,2-trifluoroethyl)-2,3,4,5-tetrahydro-1H-2-benzazepine-4-acetate (5.16 g, 14.94 mmole) in anhydrous $CH_2Cl_2$ (60 mL) at −5 to −10° C. under argon. After an additional 1 hr at −5 to −10° C., the reaction was recooled thoroughly to −10° C. and quenched by careful dropwise addition of MeOH (60 mL). The reaction was stirred at −10 to 0° C. for 1 hr, then was concentrated on the rotavap. The residue was reconcentrated from MeOH (2×) then from EtOAc, then was filtered through a pad of silica gel (EtOAc eluent). Concentration of the filtrate left a yellow solid which was triturated with hot hexanes. The title compound (4.74 g, 96%) was obtained as an off-white solid: TLC (1:1 EtOAc/hexanes) $R_f$ 0.40; $^1$H NMR (400, DMSO-$d_6$) δ 9.28 (s, 1 H), 6.90 (d, J=8.3 Hz, 1 H), 6.62 (dd, J=8.3, 2.5 Hz, 1 H), 6.57 (d, J=2.5 Hz, 1 H), 5.27 (d, J=16.7 Hz, 1 H), 4.22–4.38 (m, 1 H), 4.07–4.22 (m, 1 H), 4.07 (d, J=16.7 Hz, 1 H), 3.72–3.83 (m, 1 H), 3.58 (s, 3 H), 2.94 (dd, J=17.0, 3.8 Hz, 1 H), 2.72 (dd, J=16.7, 9.1 Hz, 1 H), 2.65 (dd, J=17.0, 14 Hz, 1 H), 2.49 (dd, J=16.7, 5.0 Hz, 1 H, partially obscured by residual solvent signal); MS (ES) m/e 354 (M+Na)$^+$.

Preparation 7

HPLC Separation of the Enantiomers of methyl (±)-8-hydroxy-3-oxo-2,3,4,5-tetrahydro-1H-2-benzazepine-4-acetate a) Methyl (R)-(+)-8-hydroxy-3-oxo-2,3,4,5-tetrahydro-1H-2-benzazepine-4-acetate and methyl (S)-(−)-8-hydroxy-3-oxo-2,3,4,5-tetrahydro-1H-2-benzazepine-4-acetate Methyl (±)-8-hydroxy-3-oxo-2,3,4,5-tetrahydro-1H-2-benzazepine-4-acetate was resolved into its enantiomers by chiral HPLC using the following conditions: Diacel Chiralpak AS® column (21.2×250 mm), EtOH mobile phase, 7 mL/min flowrate, uv detection at 254 nm, 70 mg injection; $t_R$ for methyl (R)-(+)-8-hydroxy-3-oxo-2,3,4,5-tetrahydro-1H-2-benzazepine-4-acetate=21.5 min; $t_R$ for methyl (S)-(−)-8-hydroxy-3-oxo-2,3,4,5-tetrahydro-1H-2-benzazepine-4-acetate=39.1 min.

Preparation 8

HPLC Separation of the Enantiomers of methyl (±)-8-methoxy-3-oxo-2,3,4,5-tetrahydro-1H-2-benzazepine-4-acetate a) Methyl (R)-(+)-8-methoxy-3-oxo-2,3,4,5-tetrahydro-1H-2-benzazepine-4-acetate and methyl (S)-(−)-8-methoxy-3-oxo-2,3,4,5-tetrahydro-1H-2-benzazepine-4-acetate Methyl (±)-8-methoxy-3-oxo-2,3,4,5-tetrahydro-1H-2-benzazepine-4-acetate was resolved into its enantiomers by chiral HPLC using the following conditions: Diacel Chiralpak AS® column (21.2×250 mm), $CH_3CN$ mobile phase, 15 mL/min flowrate, uv detection at 254 nm, 500 mg injection; $t_R$ for methyl (R)-(+)-8-methoxy-3-oxo-2,3,4,5-tetrahydro-1H-2-benzazepine-4-acetate=10.2 min; $t_R$ for methyl (S)-(−)-8-methoxy-3-oxo-2,3,4,5-tetrahydro-1H-2-benzazepine-4-acetate=19.0 min.

Preparation 9

Demethylation of methyl (S)-(−)-8-methoxy-3-oxo-2,3,4,5-tetrahydro-1H-2-benzazepine-4-acetate a) Methyl (S)-(−)-8-hydroxy-3-oxo-2,3,4,5-tetrahydro-1H-2-benzazepine-4-acetate A solution of methyl (S)-(−)-8-methoxy-3-oxo-2,3,4,5-tetrahydro-1H-2-benzazepine-4-acetate (15.0 g, 0.057 mole) in $CHCl_3$ (160 mL) was added dropwise over 30 min to a solution of boron tribromide (20.53 mL, 0.217 mole) in $CHCl_3$ (160 mL) at −8° C. under argon, maintaining the temperature between −5° C. and 0° C. The reaction mixture was stirred at ca. −8° C. for 30 min and then MeOH (200 mL) was added, dropwise initially, maintaining the temperature at ca. 0° C. The reaction mixture was concentrated to give a viscous oil which was reconcentrated from MeOH (100 mL). The oil was dissolved in $H_2O$/MeOH and a small amount of dark solid was removed by filtration. The filtrate was neutralized (to pH 7) with 50% sodium hydroxide, depositing a white solid. The suspension pH was adjusted to 4.5 by the addition of a small amount of acetic acid and the solid was collected and dried in vacuum to give afford the title compound (9.7 g, 68%). The product was assayed for chiral purity by HPLC: Chiralpak AS® column (4.6×50 mm), 100% EtOH mobile phase, 0.5 mL/min flow rate, uv detection at 215 nm; $t_R$=7.5 min (S-enantiomer, 99%); tR=4.4 min (R-enantiomer, 1%).

Preparation 10
Preparation of 2-[(3-hydroxy-1-propyl)amino]-4,6-dimethylpyridine-N-oxide
a) 2-[(3-hydroxy-1-propyl)amino]-4,6-dimethylpyridine-N-oxide According to the procedure of Preparation 4, except substituting 2-chloro-4,6-dimethylpyridine-N-oxide (see Brown, E. V. *J. Amer. Chem. Soc.* 1957, 79, 3565) for the 2-chloropyridine-N-oxide hydrochloride, the title compound was prepared as a clear oil: MS (ES) m/e 197.2 (M+H)$^+$.

Preparation 11
Preparation of 6-(methylamino)-2-pyridylethanol
a) 2-(tert-Butoxycarbonylamino)-6-picoline To a stirred solution of 2-amino-6-picoline (4.33 g, 40 mmol), Et$_3$N (6.2 mL, 40 mmol) and CH$_2$Cl$_2$ (50 mL) at 0° C. was added di-tert-butyl dicarbonate (9.6 g, 44 mmol). After stirring at RT overnight, the reaction mixture was concentrated in vacuum, diluted with H$_2$O and extracted with CH$_2$Cl$_2$ (2×50 mL). Drying (MgSO$_4$) and concentration gave the title compound as a colorless oil: MS (ES) m/e 209 (M+H)$^+$.
b) 2-[(tert-Butoxycarbonyl)methylamino]-6-picoline To the suspension of NaH (60% dispersion in mineral oil, 0.44 g, 11 mmol) in DMF (20 mL) at 0° C. was added a solution of 2-(tert-butoxycarbonylamino)-6-picoline (2.1 g, 10 mmol) in DMF (30 mL). The reaction was stirred at 0° C. for 15 min; then methyl iodide (1.6 g, 11 mmol) was added. The reaction mixture was concentrated in vacuum, diluted with H$_2$O, and extracted with CH$_2$Cl$_2$ (3×50 mL). Drying (MgSO$_4$) and concentration gave the title compound as a colorless oil: MS (ES) m/e 223 (M+H)$^+$.
c) Ethyl-6-[(tert-butoxycarbonyl)methylamino]-2-pyridylacetate LDA (18 mmol) was prepared in THF (30 mL), cooled to −78° C., and 2-[(tert-butoxycarbonyl)methylamino]-6-picoline (2 g, 9 mmol) was added, forming a deep red solution. After 15 min, diethylcarbonate (18 mL, 15 mmol) was added. The burgundy-colored solution was stirred at −78° C. for an additional 15 min, then the reaction was quenched with saturated NH$_4$Cl solution. The mixture was warmed to RT and extracted with EtOAc (3×30 mL). The combined organic layers were washed with brine, dried (MgSO$_4$), filtered and concentrated. Silica gel chromatography gave the title compound as a colorless oil: MS (ES) m/e 294 (M+H)$^+$.
d) Ethyl-6-(methylamino)-2-pyridylacetate A solution of ethyl-6-[(tert-butoxycarbonyl)methylamino]-2-pyridylacetate (0.6 g, 2 mmol) and 4 M HCl/dioxane (5 mL, 20 mmol) was stirred at RT overnight, then was concentrated. Reconcentration from toluene gave the title compound as white solid: MS (ES) m/e 195 (M+H)$^+$.
e) 6-(Methylamino)-2-pyridylethanol To a mechanically stirred solution of LiAlH$_4$ in THF (1.0 M, 20 mL, 20.4 mmol) was added dropwise a solution of ethyl-2-(methylamino)-6-pyridylacetate (0.38 g, 2 mmol) in THF (10 mL). After the addition was completed, the reaction mixture was warmed to 0° C. and quenched with 10% NaOH solution. The solids were removed by filtration, and the filtrate was concentrated in vacuum. The residue was dissolved in CH$_2$Cl$_2$ and the solution was dried (MgSO$_4$) and concentrated. Reconcentration from toluene (3×) gave the title compound as a colorless oil: MS (ES) m/e 153 (M+H)$^+$.

Preparation 12
Preparation of 3-[(tert-butoxycarbonyl)amino]-1-propanol
a) 3-[(tert-Butoxycarbonyl)amino]-1-propanol A solution of di-tert-butyl dicarbonate (10.91 g, 50 mmole) in CH$_2$Cl$_2$ (50 mL) was added dropwise to a solution of 3-amino-1-propanol (11.5 mL, 150 mL) in CH$_2$Cl$_2$ (250 mL) at 0° C. The cloudy solution was warmed to RT and stirred for 1 hr, then was concentrated on the rotavap. The residue was taken up in H$_2$O (100 mL) and extracted with Et$_2$O (3×100 mL). Drying (MgSO$_4$) and concentration left the title compound as a colorless oil: $^1$H NMR (250 MHz, CDCl$_3$) δ 4.80 (br s, 1 H), 3.50–3.80 (m, 2 H), 3.13–3.42 (m, 2 H), 3.03 (br t, 1 H), 1.55–1.80 (m, 2 H), 1.45 (s, 9 H); MS (ES) m/e 198 (M+Na)$^+$.

Preparation 13
Preparation of 3-(4-nitrobenzyloxycarbonylamino)-1-propanol
a) 3-(4-Nitrobenzyloxycarbonylamino)-1-propanol To a solution stirred under argon at room temperature of 3-amino-1-propanol (0.77 g, 1.1 mmol) and triethylamine (2.85 mL, 7 mmol) in THF (5 mL) was added a suspension of 4-nitrobenzyl chloroformate (2 g, 1 mmol) in THF (20 mL). The resulting mixture was allowed to stir at room temperature over the weekend, then was concentrated. The residue was purified by chromatography on silica gel (0%–2% MeOH/CH$_2$Cl$_2$) to give the title compound (0.80 g, 34%) as a pale yellow oil: MS (ES) m/e 254.3 (M+H)$^+$.

Preparation 14
Preparation of 2-[N-(3-hydroxy-1-propyl)-N-(tert-butoxycarbonyl)amino]pyridine-N-oxide
a) 2-[N-(3-hydroxy-1-propyl)-N-(tert-butoxycarbonyl)amino]pyridine-N-oxide A solution of 2-[(3-hydroxy-1-propyl)amino]pyridine-N-oxide (8.0 g, 47.6 mmol) in tert-BuOH (80 mL) was treated with di-tert-butyl dicarbonate (11.4 g, 55.3 mmol). After 18 h, the solution was concentrated and the residue was triturated with hexane. The resulting solid was dried in vacuo to give the title compound (12.5 g, 98%) as an off-white solid: MS (ES) m/e 269.3 (M+H)$^+$.

Preparation 15
Preparation of methyl (±)-8-[3-[N-(1-oxopyridin-2-yl)-N-(tert-butoxycarbonyl)amino]-1-propyloxy]-3-oxo-2,3,4,5-tetrahydro-1H-2-benzazepine-4-acetate
a) Methyl (±)-8-[3-[N-(1-oxopyridin-2-yl)-N-(tert-butoxycarbonyl)amino]-1-propyloxy]-3-oxo-2,3,4,5-tetrahydro-1H-2-benzazepine-4-acetic acid According to the procedure of Example 1(a), except substituting 2-[N-(3-hydroxy-1-propyl)-N-(tert-butoxycarbonyl)amino]pyridine-N-oxide for the 2-[(3-hydroxy-1-propyl)amino]pyridine-N-oxide, the title compound was prepared as a light orange foam: MS (ES) m/e 500.4 (M+H)$^+$.

Preparation 16
Preparation of 2-[(3-hydroxy-1-propyl)amino]-4-methylpyridine-N-oxide A mixture of 2-chloro-4-methylpyridine-N-oxide (12.1 g, 0.068 mole) (Brown, E. V. *J. Amer. Chem. Soc.* 1957, 79, 3565), 3-amino-1-propanol (10.33 mL, 0.14 mole), NaHCO$_3$ (28 g, 0.34 mole), and tert-amyl alcohol (70 mL) was heated to reflux. After 16 hr, the reaction was cooled, diluted with CH$_2$Cl$_2$ (300 mL), and suction filtered to remove insoluble materials. The filtrate was concentrated and reconcentrated from toluene to leave a yellow oil. Recrystallization from CH$_2$Cl$_2$/Et$_2$O gave the title compound (10.87 g, 88%) as a yellow solid: TLC (15% MeOH/CH$_2$Cl$_2$) R$_f$ 0.44; $^1$H NMR (400, CDCl$_3$) δ 7.92 (d, J=6.7, 1 H), 7.28 (br t, 1 H), 6.43 (s, 1 H), 6.33 (dd, J=6.6, 2.1 Hz, 1 H), 3.73 (t, J=5.7 Hz, 2 H), 3.47 (q, H=6.3 Hz, 2 H), 2.29 (s, 3 H), 1.82–1.88 (m, 2 H); MS (ES) m/e 183 (M+H)$^+$.

Preparation 17
Preparation of methyl (S)-8-hydroxy-3-oxo-2-[-4-(trifluoromethyl)benzyl]-2,3,4,5-tetrahydro-1H-2-benzazepine-4-acetate via alkylation of methyl (S)-8-hydroxy-3-oxo-2,3,4,5-tetrahydro-1H-2-benzazepine-4-acetate a) Methyl (S)-3-oxo-8-[4-(trifluoromethyl)benzyloxy]-2-[4-(trifluoromethyl)benzyl]-2,3,4,5-tetrahydro-1H-2-benzazepine-4-acetate To a solution of methyl (S)-8-hydroxy-3-oxo-2,3,4,5-tetrahydro-2-1H-benzazepine-4-acetate (0.31 g, 1.24 mmol) and 4-(trifluoromethyl)benzyl bromide (0.89 g, 3.72 mmol) in DMF (10 mL) was added NaH (60% suspension in oil, 0.11 g, 2.75 mmol). After stirring at RT for 4 h, the bulk of the DMF was removed under vacuum. The residue was partitioned between sat. NaHCO$_3$ and EtOAc. The aqueous phase was extracted with EtOAc and the combined organic extracts were washed with sat. NaCl, dried over Na$_2$SO$_4$ and concentrated to give a clear oil (0.90 g). Radial chromatography (5% acetone/CH$_2$Cl$_2$, silica gel, 6 m plate) gave the title compound (0.53 g) as a white foam. MS (ES) m/e 566.1 (M+H)$^+$.

b) Methyl (S)-8-hydroxy-3-oxo-2-[4-(trifluoromethyl)benzyl]-2,3,4,5-tetrahydro-1H-2-benzazepine-4-acetate A Parr hydrogenation flask was charged with methyl (S)-3-oxo-8-[4-(trifluoromethyl)benzyloxy]-2-[4-(trifluoromethyl)benzyl]-2,3,4,5-tetrahydro-1H-2-benzazepine-4-acetate (0.78 g, 1.38 mmol) and Pearlman's catalyst (20 mg) in MeOH (20 mL). After hydrogenating at 50 psi for 24 h, the reaction vessel was vented and the catalyst was removed by filtration. Removal of solvent gave a white foam (0.60 g). Radial chromatography (5% acetone/CH$_2$Cl$_2$, silica gel, 6 m plate) gave the title compound (0.42 g) as a white foam. $^1$H NMR (250 MHz, CDCl$_3$) δ 7.50 (d, J=8.5 Hz, 2H), 7.23 (d, J=8.5 Hz, 2H), 6.90 (d, J=7.5 Hz, 1H), 6.67 (dd, J=7.5, 3.4 Hz, 1H), 6.39 (d, J=3.4 Hz, 1H), 5.05 (m, 2 H), 4.35 (d, J=15.4 Hz, 1H), 3.85 (m, 1H), 3.70 (s, 3H), 3.60 (m, 1H), 2.95 (m, 4H), 2.45 (dd, J=17.1, 5.1 Hz, 1H).

Preparation 18
Preparation of methyl (S)-8-hydroxy-3-oxo-2-[4-(trifluoromethyl)benzyl]-2,3,4,5-tetrahydro-1H-2-benzazepine-4-acetate via Enantioselective Synthesis a) 4-Bromo-3-bromomethylanisole To a stirred solution of 4-bromo-3-methylanisole (100 g, 497 mmol) in dry dichloromethane (500 mL) was added N-bromosuccinimide (97 g, 545 mmol) followed by benzoyl peroxide (6 g, 25 mmol). The reaction was gently refluxed with a 150 watt flood lamp with reflector placed approximately 12 inches from the reaction flask. After 24 h the reaction was concentrated by rotary evaporation to half its volume and allowed to sit for 4 h. The white precipitate which formed was filtered off and rinsed with a small volume of dichloromethane. The filtrate was concentrated to dryness and the remaining solid was triturated with hexanes and filtered. Drying under vacuum gave the title compound (100.25 g, 72%) as white needles: GC t$_R$=6.56 min (HP 530 μm×20 m methylsilicone column, He carrier flow 20 mL/min, 100° C. initial temp., 1 min initial time, 10° C./min rate, 200° C. final temp., 1 min final time); $^1$H NMR (400 MHz, CDCl$_3$) δ 7.44 (d, J=10 Hz, 1 H), 6.99 (d, J=3 Hz, 1 H), 6.73 (dd, 1H), 4.55 (s, 2H), 3.80 (s, 3H).

b) 3-[N-(4-Trifluoromethylbenzyl)aminomethyl]-4-bromoanisole

To a stirred solution of 4-bromo-3-bromomethylanisole (35 g, 125 mmol) in anhydrous DMSO (50 mL) and dry THF (50 mL) was added 4-trifluoromethylbenzylamine (30 g, 171 mmol) followed by triethylamine (18 mL, 129 mmol). After stirring for 18 h at RT the reaction was concentrated, diluted with aqueous 1 N NaOH (250 mL) and extracted with Et$_2$O (2×250 mL). The combined organic layers were washed with brine, dried (Na$_2$SO$_4$), and concentrated to dryness. The residue which remained was purified by flash chromatography on silica gel (10 to 20% EtOAc/CHCl$_3$) to give the title compound (34.17 g, 73%): TLC (20% EtOAc/CHCl$_3$) R$_f$ 0.63; $^1$H NMR (400 MHz, CDCl$_3$) δ 7.59 (d, J=8.2 Hz, 2H), 7.49 (d, J=8.2 Hz, 2H), 7.43 (d, J=8.6 Hz, 1H), 6.96 (d, J=3.1 Hz, 1H), 6.70 (dd, 1H), 3.86 (s, 2H), 3.84 (s, 2H), 3.79 (s, 3H), 1.75 (br s, 1H).

c) 3-[N-(tert-Butoxycarbonyl)-N-(4-trifluoromethylbenzyl)aminomethyl]-4-bromoanisole To a stirred solution of 3-[N-(4-trifluoromethylbenzyl)aminomethyl]-4-bromoanisole (34.17 g, 91 mmol) in dry THF (100 mL) was added di-tert-butyl dicarbonate (22 g, 101 mmol). The reaction was stirred under argon for 18 h (vigorous gas evolution was observed). Concentration and silica gel chromatography (5 to 10% EtOAc/hexane) gave the title compound (41.09 g, 95%) as a clear oil: TLC (silica, 20% EtOAc/hexane) R$_f$ 0.44; $^1$H NMR (400 MHz, CDCl$_3$) δ 7.57 (d, J=8.3 Hz, 2H), 7.40 (d, J=8.3 Hz, 2H), 7.39–7.33 (m, 2H), 6.83 and 6.72 (2 s, 1H), 6.71 (dd, 1H), 4.54 and 4.50 (2 s, 2H), 4.43 (s, 2H), 3.75 (s, 3H), 1.47 (s, 9H).

d) Methyl 2-[N-(tert-butoxycarbonyl)-N-(4-trifluoromethylbenzyl)aminomethyl]-4-methoxycinnamate A solution of 3-[N-(tert-butoxycarbonyl)-N-(4-trifluoromethylbenzyl)aminomethyl]-4-bromoanisole (37.08 g, 78 mmol), methyl acrylate (35 mL, 390 mmol), palladium acetate (0.88 g, 3.9 mmol), tri-o-tolylphosphine (2.38 g, 7.8 mol), and diisopropylethylamine (31 mL, 178 mmol) in acetonitrile (200 mL) was deoxygenated (3 evacuation/argon purge cycles), then was heated to reflux under argon (oil bath set at 80° C.). After 6 hr additional palladium acetate (0.88 g, 3.9 mmol) and tri-o-tolylphosphine ((2.38 g, 7.8 mmol) were added and the reaction was stirred under reflux for an additional 18 h. The reaction was concentrated to dryness, and the residue was taken up in 1:1 Et$_2$O/petroleum ether (300 mL) and allowed to stand for 4 h. A gray-colored precipitate was filtered off and washed with a small volume of 1:1 Et$_2$O/petroleum ether (100 mL). The orangish-red filtrate was concentrated and purified by flash chromatography on silica gel (15% ethyl acetate/hexanes). The resulting residue was taken up in hexane, and the mixture was allowed to stand for several hr, then was filtered to remove a yellow precipitate. Concentration of the filtrate left the title compound (34.52 g, 92%) as a thick yellow oil: TLC (silica, 20% EtOAc/hexanes) R$_f$ 0.45; $^1$H NMR (400 MHz, CDCl$_3$) δ 7.80 (br s, 1H), 7.57 (d, J=8.1 Hz, 2H), 7.53 (d, J=8.6 Hz, 1H), 7.29 (br s, 2H), 6.83 (dd, 1H), 6.72 (br s, 1H), 6.23 (d, J=15.7 Hz, 1H), 4.58 and 4.53 (2 br s, 2H), 4.46 and 4.37 (2 br s, 2H), 3.80 (s, 3H), 3.77 (s, 3H), 1.49 (s, 9H).

e) Methyl 2-[N-(tert-butoxycarbonyl)-N-(4-trifluoromethylbenzyl)aminomethyl]-4-methoxydihydrocinnamate To 10% Pd/C (5 g, 4.7 mmol, prewetted with DMF) was added a solution of methyl 2-[N-(tert-butoxycarbonyl)-N-(4-trifluoromethylbenzyl)aminomethyl]-4-methoxycinnamate (34.52 g, 72 mmol) in methanol (100 mL). The mixture was shaken under hydrogen (50 psi) in a Parr apparatus for 7 hr, then was filtered through a pad of celite® to remove the catalyst. The filtrate was concentrated to afford the title compound (34.15 g, 98%) as a colorless oil: $^1$H NMR (400 MHz, CDCl$_3$) δ 7.58 (d, J=8.1 Hz, 2H), 7.31 (br s, 2H), 7.09 (d, J=8.4 Hz, 1H), 6.76 (dd, 1H), 6.66 (s, 1H), 4.47 (br s, 2H), 4.40 (br s, 2H), 3.76 (s, 3H), 3.63 (s, 3H), 2.79 (br s, 2H), 2.47 (t, 2H), 1.48 (s, 9H.

f) 2-[N-(tert-Butoxycarbonyl)-N-(4-trifluoromethylbenzyl) aminomethyl]-4-methoxydihydrocinnamic acid To a stirred solution of 2-[N-(tert-butoxycarbonyl)-N-(4-trifluorobenzyl)aminomethyl]-4-methoxydihydrocinnamic acid (34.15 g, 71 mmol) in dioxane (150 mL) was added aqueous 1 N NaOH (85 mL, 85 mmol). The cloudy reaction was stirred at RT for 4 h. The resulting homogeneous solution was neutralized with aqueous 1 N HCl (85 mL, 85 mmol) and extracted with ethyl acetate (2×250 mL). The combined organic layers were washed with brine (250 mL), dried (MgSO$_4$) and concentrated to give the title compound (34.60 g, 100%) as a thick clear oil: TLC (95:4:1 CHCl$_3$/MeOH/HOAc) R$_f$ 0.49; $^1$H NMR (400 MHz, CDCl$_3$) δ 7.58 (d, J=8.1 Hz, 2H), 7.30 (br s, 2H), 7.09 (d, J=8.4 Hz, 11H), 6.78 (dd, 1H), 6.65 (d, J=2.6 Hz, 1H), 4.47 (br s, 2H), 4.42 (br s, 2H), 3.76 (s, 3H), 2.81 (br s, 2H), 2.53 (t, 2H), 1.47 (s, 9H).

g) (R)-4-Benzyl-2-oxazolidinonyl 2-[N-(tert-butoxycarbonyl)-N-(4-trifluoromethylbenzyl) aminomethyl]-4-methoxydihydrocinnamide To a stirred solution of 2-[N-(tert-butoxycarbonyl)-N-(4-trifluoromethylbenzyl)aminomethyl]-4-methoxydihydrocinnamic acid (34.60 g, 71 mmol) and pyridine (6.9 mL, 85 mmol) in dry dichloromethane (200 mL) under Argon was added cyanuric fluoride (4.4 mL, 48 mmol) via syringe. The reaction was stirred for 4 h at RT. The resulting thick suspension was filtered through a pad of celite® and rinsed with a small volume of dry dichloromethane (50 mL). The clear filtrate was poured into a separatory funnel and washed with ice-cold water (500 mL). Drying (MgSO$_4$) and concentration left the crude acid fluoride (34.70 g, 100%) which was used without further purification.

To a stirred solution of (R)-4-benzyl-2-oxazolidinone (13.8 g, 78 mmol) in dry THF (300 mL) under argon at −78° C. was added via syringe a solution of n-BuLi in hexanes (2.5 M, 30 mL, 75 mmol). The reaction was stirred at −78° C. for 15 min, then a solution of the above acid fluoride (34.70 g, 71 mmol) in dry THF (100 mL) was added via syringe. The reaction was stirred for 1 h at −78° C. then was quenched with saturated NH$_4$Cl and extracted with ethyl acetate (2×200 mL). The combined organic layers were washed with brine (400 mL), dried (MgSO$_4$), and concentrated to dryness. Purification by flash chromatography on silica gel (20% ethyl acetate/hexanes) gave the title compound (40.34 g, 90%) as a thick clear oil: TLC (20 % EtOAc/hexane) R$_f$ 0.21; $^1$H NMR (400 MHz, CDCl$_3$) δ 7.58 (d, J=8.1 Hz, 2H), 7.33–7.26 (m, 5H), 7.16 (m, 3H), 6.77 (dd, 1H), 6.67 (d, J=2.5 Hz, 1H), 4.62 (m, 1H), 4.60–4.40 (m, 4H), 4.16 (m, 2H), 3.76 (s, 3H), 3.27 (dd, 1H), 3.21–3.10 (m, 2H), 2.88 (br s, 2H), 2.72 (dd, 1H), 1.48 (s, 9H).

h) (R)-Benzyl-2-oxazolidinonyl 3-[2-[N-(tert-butoxycarbonyl)-N-(4-trifluoromethylbenzyl) aminomethyl]-4-methoxyphenyl]-2-(S)-methoxycarbonylmethyl-propionamide To a stirred solution of (R)-4-benzyl-2-oxazolidinonyl 2-[N-(tert-butoxycarbonyl)-N-(4-trifluormethylbenzyl) aminomethyl]-4-methoxydihydrocinnamide (40.30 g, 64 mmol) in dry THF (300 mL) at −78° C. was added a solution of lithium bis(trimethylsilyl)amide (70 mL, 1 M in THF, 70 mmol) via syringe. After 30 min, methyl bromoacetate (30 mL, 317 mmol) was added via syringe. After another 30 min at −78° C. the reaction was allowed to warm to −20° C. and stirred for an additional 6 h. The reaction was quenched with saturated NH$_4$Cl (400 mL) and extracted with ethyl acetate (2×200 mL). The combined organic layers were washed with brine (300 mL), dried (MgSO$_4$), and concentrated to dryness. Purification by flash chromatography on silica gel (20% ethyl acetate/hexanes) gave the title compound (38.62 g, 86%) as a white solid: HPLC (Altex Ultrasphere™-Si 5u, 20% EtOAc/hexane) showed approximately 20% unalkylated starting material was still present. HPLC of the crude reaction mixture gave a de of 90% for the reaction; $^1$H NMR (400 MHz, CDCl$_3$) δ 7.57 (d, J=8.1 Hz, 2H), 7.40–7.11 (m, 8H), 6.71 (dd, 1H), 6.63 (d, J=2.7 Hz, 1H), 4.57–4.34 (m, 6H), 4.03 (d, J=8.6 Hz, 1H), 3.85 (t, 1H), 3.72 (s, 3H), 3.61 (s, 3H), 3.28 (dd, 1H), 2.90 (dd, 1H), 2.86–2.71 (m, 2H), 2.70 (dd, 1H), 2.44 (m, 1H), 1.48 and 1.46 (2s, 9H).

i) Methyl (S)-8-methoxy-3-oxo-2-(4-trifluoromethylbenzyl)-2,3,4,5-tetrahydro-1H-2-benzazepine-4-acetate To a stirred solution of (R)-4-benzyl-2-oxazolidinonyl 3-[2-[N-(tert-butoxycarbonyl)-N-(4-trifluoromethylbenzyl) aminomethyl]-4-methyoxyphenyl]-2(S)-methoxycarbonylmethyl-propionamide (38.0 g, 54 mmol) in THF (300 mL) and water (100 mL) was added dropwise at 0° C. over 30 min a solution of 30% H$_2$O$_2$ (18.9 mL) and LiOH.H$_2$O (2.3 g, 55 mmol) in water (62 mL). The cloudy solution was stirred for an additional 1 h at 0° C. The resulting homogeneous solution was treated slowly with a solution of sodium sulfite (34.3 g, 272 mmol) in water (175 mL) at 0° C., then was acidified with an ice-cold solution of concentrated HCl (35 mL) in water (150 mL). The reaction was extracted with ethyl acetate (2×200 mL), and the combined organic layers were washed with brine (400 mL), dried (MgSO$_4$) and concentrated to dryness. The resulting residue was treated with 4.0 M HCl in dioxane (400 mL) with stirring at RT (slow gas evolution was observed). After 1 h, the reaction was concentrated and reconcentrated from 1:1 CHCl$_3$/toluene (2×), then the residue (37.65 g) was taken up in dry DMF (400 mL). To this solution with stirring under argon at 0° C. in a Dewar flask were added triethylamine (15.3 mL, 109 mmol) and NaHCO$_3$ (22.9 g, 273 mmol), followed by diphenylphosphoryl azide (13 mL, 60 mmol). After stirring for 24 h at 0° C. the reaction was concentrated to dryness. The residue was taken up in ethyl acetate (400 mL), and washed sequentially with water (300 mL) and brine (300 mL). Drying (MgSO$_4$), concentration, and flash chromatography on silica gel (35% ethyl acetate/hexanes) gave the title compound (16.87 g, 74%) as a clear thick oil: TLC (40% EtOAc/hexane) R$_f$ 0.50; MS (ES) m/e 422.3 (M+H)$^+$; $^1$H NMR (400 MHz, CDCl$_3$) δ 7.52 (d, J=8.1, 2H), 7.29 (d, J=8.1 Hz, 2H), 7.02 (d, J=8.5 Hz, 1H), 7.75 (dd, 1H), 6.36 (d, J=2.7 Hz, 1H), 5.18 (d, J=16.5 Hz, 1H), 4.96 (d, J=15.4 Hz, 1H), 4.48 (d, J=15.4 Hz, 1H), 3.87 (m, 1H), 3.74 (d, J=16.5 Hz, 1H), 3.73 (s, 3H), 3.71 (s, 3H), 3.08 (dd, 1H), 3.02 (dd, 1H), 2.95 (dd, 1H), 2.48 (dd, 1H).

j) Methyl (S)-8-hydroxy-3-oxo-2-(4-trifluoromethylbenzyl)-2,3,4,5-tetrahydro-1H-2-benzazepine-4-acetate A solution of boron tribromide in CH$_2$Cl$_2$ (1.0 M, 160 mL, 160 mmol) was added dropwise over 30 min to a solution of methyl (S)-8-methoxy-3-oxo-2-(4-trifluoromethylbenzyl)-2,3,4,5-tetrahydro-1H-2-benzazepine-4-acetate (16.67 g, 39.6 mmol) in anhydrous CH$_2$Cl$_2$ (150 mL) at −20° C. under argon. After an additional 1.5 hr at −15 to −20° C., the reaction was recooled to −20° C. and quenched by careful dropwise addition of MeOH (160 mL). The reaction was stirred at −10 to 0° C. for 1 hr, then was concentrated on the rotavap. The residue was reconcentrated from MeOH (2×). Purification by flash chromatography on silica gel (50 to 100% ethyl acetate/hexanes) gave the title compound (14.87 g, 92%) as a white solid: $[\alpha]_D$ −81.8° (c, 1.0, MeOH); TLC (silica, 50% EtOAc/hexane) $R_f$ 0.54; MS (ES) m/e 408.2 (M+H)$^+$; $^1$H NMR (400, CDCl$_3$+2% DMSO-d$_6$) δ 7.53 (d, J=8.1 Hz, 2H), 7.31 (d, J=8.1 Hz, 2H), 6.93 (d, J=8.4 Hz, 1H), 6.70 (dd, 1H), 6.41 (d, J=2.3 Hz, 1H), 5.16 (d, J=16.4 Hz, 1H), 5.01 (d, J=15.6 Hz, 1H), 4.39 (d, J=15.6 Hz, 1H), 3.84 (m, 1H), 3.73 (d, J=16.4 Hz, 1H), 3.71 (s, 3H), 3.01 (dd, 1H), 2.98 (m, 1H), 2.90 (dd, 1H), 2.47 (dd, 1H).

Preparation 19
HPLC Separation of the Enantiomers of Methyl (±)-8-methoxy-3-oxo-2-(2,2,2-trifluoroethyl)-2,3,4,5-tetrahydro-2-benzazepine-4-acetate a) Methyl (R)-(+)-8-methoxy-3-oxo-2-(2,2,2-trifluoroethyl)-2,3,4,5-tetrahydro-2-benzazepine-4-acetate and methyl (S)-(−)-8-methoxy-3-oxo-2-(2,2,2-trifluoroethyl)-2,3,4,5-tetrahydro-2-benzazepine-4-acetate Methyl (±)-8-methoxy-3-oxo-2-(2,2,2-trifluoroethyl)-2,3,4,5-tetrahydro-2-benzazepine-4-acetate was resolved into its enantiomers by chiral HPLC using the following conditions: Diacel Chiralcel OJ® column (21.2×250 mm), methanol mobile phase, 15 mL/min flowrate, uv detection at 295 nm, 400 mg injection; $t_R$ for methyl (R)-(+)-8-methoxy-3-oxo-2-(2,2,2-trifluoroethyl)-2,3,4,5-tetrahydro-2-benzazepine-4-acetate=4.9 min; $t_R$ for methyl (S)-(−)-8-methoxy-3-oxo-2-(2,2,2-trifluoroethyl)-2,3,4,5-tetrahydro-2-benzazepine-4-acetate=6.6 min.

Preparation 20
HPLC Separation of the Enantiomers of Methyl (±)-8-hydroxy-3-oxo-2-(2,2,2-trifluoroethyl)-2,3,4,5-tetrahydro-2-benzazepine-4-acetate a) Methyl (R)-(+)-8-hydroxy-3-oxo-2-(2,2,2-trifluoroethyl)-2,3,4,5-tetrahydro-2-benzazepine-4-acetate and methyl (S)-(−)-8-hydroxy-3-oxo-2-(2,2,2-trifluoroethyl)-2,3,4,5-tetrahydro-2-benzazepine-4-acetate Methyl (±)-8-hydroxy-3-oxo-2-(2,2,2-trifluoroethyl)-2,3,4,5-tetrahydro-2-benzazepine-4-acetate was resolved into its enantiomers by chiral HPLC using the following conditions: Diacel Chiralcel OD® column (21.2×250 mm), 20% ethanol in hexane mobile phase, 10 mL/min, uv detection at 254 nm, 100 mg injection; $t_R$ for methyl (R)-(+)-8-hydroxy-3-oxo-2-(2,2,2-trifluoroethyl)-2,3,4,5-tetrahydro-2-benzazepine-4-acetate=14.4 min; $t_R$ for methyl (S)-(−)-8-hydroxy-3-oxo-2-(2,2,2-trifluoroethyl)-2,3,4,5-tetrahydro-2-benzazepine-4-acetate=18.5 min.

Preparation 21
Preparation of Methyl (S)-8-hydroxy-3-oxo-2-(2,2,2-trifluoroethyl)-2,3,4,5-tetrahydro-1H-2-benzazepine-4-acetate Via Enantioselective Synthesis a) 4-Bromo-3-bromomethylanisole To a stirred solution of 4-bromo-3-methylanisole (100 g, 497 mmol) in dry dichloromethane (500 mL) was added N-bromosuccinimide (97 g, 545 mmol) followed by benzoyl peroxide (6 g, 25 mmol). The reaction was gently refluxed with a 150 watt flood lamp with reflector placed approximately 12 inches from the reaction flask. After 24 h the reaction was concentrated by rotary evaporation to half its volume and allowed to sit for 4 h. The white precipitate which formed was filtered off and rinsed with a small volume of dichloromethane. The filtrate was concentrated to dryness and the remaining solid was triturated with hexanes and filtered. Drying under vacuum gave the title compound (100.25 g, 72%) as white needles: GC $t_R$=6.56 min (HP 530 μm×20 m methylsilicone column, He carrier flow 20 mL/min, 100° C. initial temp., 1 min initial time, 10° C./min rate, 200° C. final temp., 1 min final time); $^1$H NMR (400 MHz, CDCl$_3$) δ 7.44 (d, J=10 Hz, 1 H), 6.99 (d, J=3 Hz, 1 H), 6.73 (dd, 1H), 4.55 (s, 2H), 3.80 (s, 3H).

b) 3-[N-(2,2,2-Trifluoroethyl)aminomethyl]-4-bromoanisole 2,2,2-Trifluoroethylamine (24 g, 242 mmol) was added rapidly to a stirred solution of 4-bromo-3-bromomethylanisole (33.6 g, 120 mmol) in anhydrous DMSO (125 mL) at RT. The reaction warmed to approximately 30–35° C. After stirring for 18 hr, the reaction was diluted with ice-cold 1 N NaOH (200 mL) and extracted with Et$_2$O (2×300 mL). The combined organic layers were washed with brine (300 mL), dried (MgSO$_4$), and concentrated to give the title compound (41.35 g, 96%) as a pale yellow oil: TLC (toluene) $R_f$ 0.32; $^1$H NMR (400 MHz, CDCl$_3$) δ 7.43 (d, J=9 Hz, 1H), 6.97 (d, J=3 Hz, 1H), 6.71 (dd, 1H), 3.93 (br s, 2H), 3.80 (s, 3H), 3.18 (m, 2H), 1.86 (br s, 1H).

c) 3-[N-(tert-Butoxycarbonyl)-N-(2,2,2-trifluoroethyl)aminomethyl]-4-bromoanisole To 3-[N-(2,2,2-trifluoroethyl)aminomethyl]-4-bromoanisole (41.35 g, 137 mmol) was added di-tert-butyl dicarbonate (36 g, 165 mmol, liquefied by warming in a hot water bath). The reaction was rinsed down with a small amount of dichloromethane (~20 mL) and stirred under argon in a 50° C. oil bath for 18 h (slow gas evolution was observed). After concentration by rotary evaporation under vacuum the resulting residue was diluted with hexanes (100 mL) and the solution was seeded with a small amount of the pure solid product (obtained from a previous reaction by silica gel chromatography using 10% EtOAc/hexanes as eluent). The mixture was allowed to stand at RT for several hours then was placed in the refrigerator overnight. The product was collected by suction filtration and washed with hexanes. Drying in vacuum gave the title compound (48.54 g, 88%) as a colorless solid: TLC (10% EtOAc/toluene) $R_f$ 0.52; $^1$H NMR (400 MHz, CDCl$_3$) δ 7.44 (d, J=9 Hz, 1H), 6.75 (dd, 1H), 6.71 (s, 1H), 4.65 and 4.58 (2s, 2H), 3.90 and 3.78 (2m, 2H), 3.77 (s, 3H), 1.51 and 1.42 (2s, 9H).

d) Methyl 2-[N-(tert-butoxycarbonyl)-N-(2,2,2-trifluoroethyl)aminomethyl]-4-methoxycinnamate A solution of 3-[N-(tert-butoxycarbonyl)-N-(2,2,2-trifluoroethyl)aminomethyl]-4-bromoanisole (48.19 g, 121 mmol), methyl acrylate (55 mL, 605 mmol), palladium acetate (1.36 g, 6.1 mmol), tri-o-tolylphosphine (3.69 g, 12 mol), and diisopropylethylamine (49 mL, 278 mmol) in acetonitrile (200 mL) was deoxygenated (3×evacuation/argon purge cycles), then was heated to reflux under argon in oil bath set at 80° C. After 6 hr additional palladium acetate (1.36 g, 6.1 mmol) and tri-o-tolylphosphine (3.69 g, 12 mmol) were added and the reaction was stirred under reflux for an additional 18 h. The reaction was concentrated to dryness, and the residue was taken up in 1:1 Et$_2$O/petroleum ether (300 mL) and allowed to stand for 4 h. A gray-colored precipitate was filtered off and washed with a small volume of 1:1 Et$_2$O/petroleum ether(~100 mL). The orangish-red filtrate was concentrated and purified by flash chromatography on silica gel (15% ethyl acetate/hexanes). The resulting residue was taken up in hexane, and the mixture was allowed to stand for 2 hr, then was filtered to remove a yellow precipitate. Concentration of the filtrate left the title compound (45.85 g, 94%) as a yellow oil: TLC (20% EtOAc/hexane) $R_f$ 0.50; $^1$H NMR (400 MHz, CDCl$_3$) δ 7.84 (d, J=16 Hz, 1H), 7.57 (d, J=9 Hz, 1H), 6.86 (dd, 1H), 6.74 and 6.72 (2s, 1H), 6.26 (d, J=16 Hz, 1H), 4.74 and 4.70 (2s, 2H), 3.83 (s, 3H), 3.79 (s, 3H), 3.80 and 3.66 (2m, 2H), 1.51 and 1.45 (2s, 9H).

e) Methyl 2-[N-(tert-butoxycarbonyl)-N-(2,2,2-trifluoroethyl)aminomethyl]-4-methoxydihydrocinnamate To 10% Pd/C (5 g, 4.7 mmol, prewetted with DMF) was added a solution of methyl 2-[N-(tert-butoxycarbonyl)-N-(2,2,2-trifluoroethyl)amino]methyl-4-methoxycinnamate (45.85 g, 113 mmol) in methanol (100 mL). The mixture was shaken under hydrogen (50 psi) in a Parr apparatus for 6 hr, then was filtered through a pad of celite® to remove the catalyst. The filtrate was concentrated to afford the title compound (43.71 g, 95%) as a colorless oil: $^1$H NMR (400 MHz, CDCl$_3$) δ 7.11 (d, J=8 Hz, 1H), 6.78 (dd, 1H), 6.65 (s, 1H), 4.63 and 4.60 (2s, 2H), 3.84 and 3.70 (2m, 2H), 3.77 (s, 3H), 3.66 (s, 3H), 2.86 (t, 2H), 2.53 (t, 2H), 1.50 and 1.44 (2s, 9H).

f) 2-[N-(tert-Butoxycarbonyl)-N-(2,2,2-trifluoroethyl) aminomethyl]-4-methoxydihydrocinnamic acid To a stirred solution of methyl 2-[N-(tert-butoxycarbonyl)-N-(2,2,2-trifluoroethyl)aminomethyl]-4-methoxydihydrocinnamate (43.71 g, 108 mmol) in dioxane (200 mL) was added aqueous 1 N NaOH (130 mL, 130 mmol). The cloudy reaction was stirred at RT for 4 h. The resulting a homogeneous solution was neutralized with 1 N HCl (130 mL, 130 mmol) and extracted with ethyl acetate (2×250 mL). The combined organic layers were washed with brine (250 mL), dried (MgSO$_4$), and concentrated to give the title compound (45.01 g, 100%) as a thick clear oil: TLC (95:4:1 CHCl$_3$, MeOH, HOAc) $R_f$ 0.49.

g) (R)-4-Benzyl-2-oxazolidinonyl 2-[N-(tert-butoxycarbonyl)-N-(2,2,2-trifluoroethyl)aminomethyl]-4-methoxydihydrocinnamide To a stirred solution of 2-[N-(tert-butoxycarbonyl)-N-(2,2,2-trifluoroethyl)aminomethyl]-4-methoxydihydrocinnamic acid (45.0 g, 108 mmol) and pyridine (10 mL, 124 mmol) in dry dichloromethane (400 mL) under argon was added cyanuric fluoride (6.8 mL, 74 mmol) via syringe. The reaction was stirred for 4 h at RT. The resulting thick suspension was filtered through a pad of celite®, and the filter pad was rinsed with a small volume of dry dichloromethane (50 mL). The clear filtrate was poured into a separatory funnel and washed with ice-cold water (750 mL). Drying (MgSO$_4$) and concentration left the crude acid fluoride (43.32 g, 100%) which was used without further purification.

To a stirred solution of (R)-4-benzyl-2-oxazolidinone (21 g, 119 mmol) in dry THF (400 mL) under argon at −78° C. was added via syringe a solution of n-BuLi in hexanes (2.5 M, 113 mmol). The reaction was stirred at −78° C. for 15 min, then a solution of the above acid fluoride (43.32 g, 108 mmol) in dry THF (100 mL) was added via syringe. The reaction was stirred for 1 h at −78° C. then was quenched with saturated NH$_4$Cl and extracted with ethyl acetate (2×250 mL). The combined organic layers were washed with brine (500 mL), dried (MgSO$_4$), and concentrated to dryness. Purification by flash chromatography on silica gel (20% ethyl acetate/hexanes) gave the title compound (55.27 g, 91%) as a thick clear oil: TLC (silica, 20% EtOAc/hexane) $R_f$ 0.24; $^1$H NMR (400 MHz, CDCl$_3$) δ 7.34–7.26 (m, 3H), 7.19–7.16 (m, 3H), 6.78 (dd, 1H), 6.67 (s, 1H), 4.68–4.63 (m, 3H), 4.21–4.11 (m, 2H), 3.87 and 3.74 (2m, 2H), 3.77 (s, 3H), 3.28 (dd, 1H), 3.17 (m, 2H), 2.93 (m, 2H), 2.75 (dd, 1H), 1.50 and 1.45 (2s, 9H).

h) (R)-4-Benzyl-2-oxazolidinonyl 3-[2-[N-(tert-butoxycarbonyl)-N-(2,2,2-trifluoroethyl)aminomethyl]-4-methoxyphenyl]-2(S)-methoxycarbonylmethyl-propionamide To a stirred solution of (R)-4-benzyl-2-oxazolidinonyl 2-[N-(tert-butoxycarbonyl)-N-(2,2,2-trifluoroethyl) aminomethyl]-4-methoxydihydrocinnamide (55.2 g, 100 mmol) in dry THF (300 mL) at −78° C. was added a solution of lithium bis(trimethylsilyl)amide (115 mL, 1 M in THF, 115 mmol) via syringe. After 30 min methyl bromoacetate (47 mL, 497 mmol) was added via syringe. After another 30 min at −78° C. the reaction was allowed to warm to −20° C. and stirred for an additional 6 h. The reaction was quenched with saturated NH$_4$Cl (400 mL) and extracted with ethyl acetate (2×250 mL). The combined organic layers were washed with brine (400 mL), dried (MgSO$_4$), and concentrated to dryness. Purification by flash chromatography on silica gel (20% ethyl acetate/hexanes) gave the title compound (52.44 g, 75%) as a white solid: HPLC (Altex Ultrasphere™-Si 5u, 20% EtOAc/hexane) showed approximately 6–7% unalkylated starting material was still present. HPLC of the crude reaction mixture gave a de of 86% for the reaction; $^1$H NMR (400 MHz, CDCl$_3$) δ 7.35–7.13 (m, 6H), 6.73 (dd, 1H), 6.64 (s, 1H), 4.69–4.53 (m, 4H), 4.04 (d, 1H), 3.87 (t, 1H), 3.85–3.72 (m, 2H), 3.75 (s, 3H), 3.64 (s, 3H), 3.31 (dd, 1H), 2.95 (dd, 1H), 2.92–2.71 (m, 2H), 2.71 (dd, 1H), 2.50 (m, 1H), 1.50 and 1.47 (2 br s, 9H).

i) Methyl (S)-8-methoxy-3-oxo-2-(2,2,2-trifluoroethyl)-2,3,4,5-tetrahydro-1H-2-benzazepine-4-acetate To a stirred solution of (R)-4-benzyl-2-oxazolidinonyl 3-[2-(N-(tert-butoxycarbonyl)-N-(2,2,2-trifluoroethyl) aminomethyl]-4-methyoxyphenyl]-2(S)-methoxycarbonylmethyl-propionamide (52.40 g, 75 mmol) in THF (300 mL) and water (100 mL) was added dropwise at 0° C. over 30 min a solution of 30% H$_2$O$_2$ (26 mL) and LiOH.H$_2$O (3.2 g, 75 mmol) in water (85 mL). The cloudy solution was stirred for an additional 1 h at 0° C. The resulting homogeneous solution was treated slowly with a solution of sodium sulfite (46 g, 365 mmol) in water (240 mL) at 0° C., then was acidified with an ice-cold solution of concentrated HCl (45 mL) in water (200 mL). The reaction was extracted with ethyl acetate (2×300 mL), and the combined organic layers were washed with brine (600 mL), dried (MgSO$_4$) and concentrated to dryness. The resulting residue was treated with 4.0 M HCl in dioxane (500 mL) with stirring at RT (slow gas evolution was observed). After 1 h, the reaction was concentrated and reconcentrated from 1:1 CHCl$_3$/toluene (2×), then the residue (48.89 g) was taken up in dry DMF (500 mL). To this solution with stirring under argon at 0° C. in a Dewar flask were added triethylamine (21 mL, 150 mmol) and NaHCO$_3$ (31.5 g, 375 mmol), followed by diphenylphosphoryl azide (18 mL, 83.5 mmol). After stirring for 24 h at 0° C., the reaction was concentrated to dryness. The residue was taken up in ethyl acetate (500 mL) and washed sequentially with water (400 mL) and brine (400 mL). Drying (MgSO$_4$), concentration, and flash chromatography on silica gel (30% ethyl acetate/hexanes) gave the title compound (21.81 g, 84%) as a white solid: $[\alpha]_D$ −132.6° (c, 1.0, MeOH); TLC (40% EtOAc/hexane) $R_f$ 0.56; chiral HPLC (Chiracel OD, 20% EtOH/hexane) k'=2.05; the opposite enantiomer from a racemic standard had k'=1.86 (none detected); MS (ES) m/e 346.2 (M+H)$^+$; $^1$H NMR (400 MHz, CDCl$_3$) δ 7.03 (d, J=8.5 Hz, 1H), 6.79 (dd, 1H), 6.61 (d, J=2.6 Hz, 1H), 5.35 (d, J=16.7 Hz, 1H), 4.17 (m, 1H), 4.0 (m, 1H), 3.99 (d, J=16.7 Hz, 1H), 3.84 (m, 1H), 3.79 (s, 3H), 3.71 (s, 3H), 3.01 (m, 2H), 2.91 (dd, 1H), 2.47 (dd, 1H). Anal. Calcd for C$_{16}$H$_{18}$F$_3$NO$_4$: C, 55.65; H, 5.25; N, 4.06. Found: C, 55.62; H, 5.27; N, 4.04.

j) Methyl (S)-8-hydroxy-2-methyl-3-oxo-2,3,4,5-tetrahydro-1H-2-benzazepine-4-acetate A solution of boron tribromide in CH$_2$Cl$_2$ (1.0 M, 250 mL, 250 mmol) was added dropwise over 30 min to a solution of methyl (S)-8-methoxy-3-oxo-2-(2,2,2-trifluoroethyl)-2,3,4,5-tetrahydro-1H-2-benzazepine-4-acetate (21.5 g, 62.3 mmol) in anhydrous CH$_2$Cl$_2$ (230 mL) at −20° C. under argon. After an additional 1.5 hr at −15 to −20° C., the reaction was recooled to −20° C. and quenched by careful dropwise addition of MeOH (250 mL). The reaction was stirred at −10 to 0° C. for 1 hr, then was concentrated on the rotavap. The residue was reconcentrated from MeOH (2×). Purification by flash chromatography on silica gel (50% ethyl acetate/hexanes) gave the title compound (19.38 g, 94%) as a white solid: [α]$_D$ −130.50 (c 1.0, MeOH); TLC (silica, 40% EtOAc/hexane) R$_f$ 0.40; MS (ES) m/e 332.1 (M+H)$^+$; $^1$H NMR (400, CDCl$_3$+2% DMSO-d$_6$) δ 6.92 (d, J=8.3 Hz, 1 H), 6.71 (dd, 1H), 6.58 (d, J=2.5 Hz, 1H), 5.29 (d, J=16.7 Hz, 1 H), 4.21–3.98 (m, 2H), 3.96 (d, J=16.7 Hz, 1H), 3.82 (m, 1H), 3.68 (s, 3H), 2.98 (dd, 1H), 2.94 (dd, 1H), 2.83 (dd, 1H), 2.46 (dd, 1H). Anal. Calcd for C$_{15}$H$_{16}$F$_3$NO$_4$: C, 54.38; H, 4.87; N, 4.23. Found: C, 54.40; H, 4.96; N, 4.22.

Preparation 22
Preparation of methyl (S)-8-hydroxy-3-oxo-2-(2-phenylethyl)-2,3,4,5-tetrahydro-1H-2-benzazepine-4-acetate Via Enantioselective Synthesis
a) 3-[N-(tert-Butoxycarbonyl)-N-(2-phenylethyl)amino]methyl-4-bromoanisole 2-Phenethylamine (19.0 mL, 150 mmole) was added all at once to a solution of 4-bromo-3-bromomethylanisole (14.0 g, 50.0 mmole) in anhydrous THF (200 mL) at RT. After 18 hr the mixture was concentrated. The residue was dissolved in 2 M NaOH (300 mL) and extracted with CH$_2$Cl$_2$ (3×200 mL). The combined CH$_2$Cl$_2$ layers were dried over MgSO$_4$ and concentrated. The crude material was filtered through a plug of silica gel using 50% EtOAc/hexanes as eluent. The filtrate was concentrated under reduced pressure to give a yellow oil: MS (ES) m/e 320 (M+H)$^+$.

The above yellow oil was dissolved in anhydrous THF (200 mL) and di-tert-butyl dicarbonate (13.0 g, 60.0 mmole) was added all at once at RT. After 1 hr the solution was concentrated. Flash silica gel chromatography (10% EtOAc/hexanes) gave the title compound as an off-white solid (20.8 g, 100% from 4-bromo-3-bromomethylanisole): $^1$H NMR (250 MHz, CDCl$_3$) δ 7.51–7.10 (m, 6H), 6.85–6.60 (m, 2H), 4.52–4.33 (m, 2H), 3.71 (s, 3H), 3.52–3.31 (m, 2H), 2.92–2.73 (m, 2H), 1.61–1.33 (m, 9H).
b) 4-[2-[N-(tert-Butoxycarbonyl)-N-(2-phenylethyl)amino]methyl-4-methoxyphenyl]propionic acid A solution of 3-[N-(tert-butoxycarbonyl)-N-(2-phenylethyl)amino]methyl-4-bromoanisole (20.0 g, 48.0 mmole), benzyl acrylate (23.0 g, 144 mmole), palladium acetate (540 mg, 2.40 mmole), tri-o-tolylphosphine (1.46 g, 4.80 mmole), and diisopropylethylamine (17.0 mL, 96.0 mmole) in propionitrile (250 mL) was deoxygenated (3× evacuation/argon purge cycles), then was heated to reflux under argon. After 48 hr the reaction was cooled to RT, filtered through a pad of celite®, and concentrated. Flash silica gel chromatography (10% EtOAc/hexane) gave a yellow oil, which was dissolved in 10% EtOAc/hexanes (100 mL) and left at 4° C. for 72 hr. The yellow precipitate was removed by filtration then the solution was concentrated to give a faint yellow oil (14.98 g, 62%): $^1$H-NMR (250 MHz, CDCl$_3$) δ 8.00–7.85 (m, 1H), 7.61–7.01 (m, 11H), 6.85–6.76 (m, 2H), 6.75–6.67 (m, 1H), 6.32 (m, 1H), 5.22 (s, 2H), 4.60–4.41 (m, 2H), 3.75 (s, 3H), 3.52–3.20 (m, 2H), 2.93–2.71 (m, 2H), 1.55–1.33 (m, 9H).

The above oil was dissolved in MeOH (150 mL) and 10% Pd/C (6.40 g, 6.00 mmole) was added at 0° C. The mixture was warmed to RT, shaken under hydrogen (50 psi) for 7 hr, then was filtered through a pad of celite® to remove the catalyst. The filtrate was concentrated under reduced pressure to give the title compound as a thick yellow oil (10.35 g, 83%): $^1$H-NMR (250 MHz, CDCl$_3$) δ 7.35–7.02 (m, 6H), 6.85–6.76 (m, 2H), 6.75–6.73 (m, 1H), 6.69–6.68 (m, 1H), 4.42–4.25 (m, 2H), 3.73 (s, 3H), 3.44–3.25 (m, 2H), 2.92–2.73 (m, 4H), 2.59–2.50 (m, 2H), 1.60–1.33 (m, 9H).
c) (R)-1,1-Dimethylethyl[[5-methoxy-2-[3-oxo-3-[2-oxo-4-(phenylmethyl)-3-oxazolidinyl]propyl]methyl](2-phenyl)carbamate To a solution of 4-[2-[N-(tert-butoxycarbonyl)-N-(2-phenylethyl)amino]methyl-4-methoxyphenyl]propionic acid (10.35 g, 25.0 mmole) in CH$_2$Cl$_2$ (125 mL) was added pyridine (2.4 mL, 30.0 mmole) then cyanuric fluoride (1.4 mL, 15.0 mmole) at RT. After 2 hr the mixture was filtered through a pad of celite®, washed with cold H$_2$O (100 mL) then with brine (100 mL), dried over MgSO$_4$, and concentrated.

To a solution of (R)-4-benzyl-2-oxazolidinone (5.30 g, 30.0 mmole) in anhydrous THF (125 mL) was added n-BuLi (11.0 mL, 2.5 M solution in hexanes, 27.5 mmole) at −78° C. After 15 minutes the above acid fluoride in anhydrous THF (25 mL) was added dropwise over 5 minutes. After 1 hr the mixture was poured into 300 mL H$_2$O and extracted with EtOAc (3×200 mL). The combined EtOAc layers were dried over MgSO$_4$ and concentrated. Flash silica gel chromatography (30% EtOAc/hexanes) gave the title compound as a thick oil (12.12 g, 85%): $^1$H-NMR (250 MHz, CDCl$_3$) δ 7.41–7.12 (m, 11H), 6.65 (m, 1H), 6.60 (m, 1H), 4.70–4.62 (m, 1H), 4.50–4.35 (m, 2H), 4.21–4.10 (m, 2H), 3.71(s, 3H), 3.50–2.61 (m, 10H), 1.55–1.41 (m, 9H).
d) [R-(R*, S*)]-Methyl β-[[4-methoxy-2-[[[(1,1-dimethylethoxy)carbonyl](2-phenylethyl)amino]methyl]phenyl]methyl]-γ-oxo-4-(phenylmethyl)-3-oxazolidinebutanoate To a solution of (R)-1,1-dimethylethyl[[5-methoxy-2-[3-oxo-3-[2-oxo-4-(phenylmethyl)-3-oxazolidinyl]propyl]phenyl]methyl](2-phenylethyl)carbamate (12.12 g, 21.0 mmole) in anhydrous THF (100 mL) was added lithium bis(trimethylsilyl)amide (22.0 mL, 1M in THF, 22.0 mmole) at −78° C. After 15 minutes methyl bromoacetate (9.9 mL, 105 mmole) was added then the mixture was warmed to −20° C. After 3 hr the mixture was poured into 200 mL H$_2$O and extracted with EtOAc (3×500 mL). The combined EtOAc layers were dried over MgSO$_4$ and concentrated. Flash silica gel chromatography (25% EtOAc/hexanes) gave 9.91 g of a 3:2 mixture (HPLC, 20% EtOAc/hexanes) of the title compound and (R)-1,1-Dimethylethyl[[5-methoxy-2-[3-oxo-3-[2-oxo-4-(phenylmethyl)-3-oxazolidinyl]propyl]phenyl]methyl](2-phenylethyl)carbamate respectively. This mixture was used without further purification: MS (ES) m/e 667 (M+Na)$^+$.
e) Methyl (S)-8-methoxy-3-oxo-2-(2-phenylethyl)-2,3,4,5-tetrahydro-1H-2-benzazepine-4-acetate To a solution of [R-(R*, S*)]-methyl β-[[4-methoxy-2-[[[(1,1-dimethylethoxy)carbonyl](2-phenylethyl)amino]methyl]phenyl]methyl]-γ-oxo-4-(phenylmethyl)-3-oxazolidinebutanoate (9.91 g, 15.4 mmole) in THF (75 mL) was added a solution of lithium hydroxide monohydrate (646 mg, 15.4 mmole) and H$_2$O$_2$ (5.2 mL, 30% in H$_2$O, 46.2 mmole) in H$_2$O (25 mL) at 0° C. over 10 minutes. After 1.5 hr a solution of Na$_2$SO$_3$ (9.7 g, 77 mmole) in H$_2$O (100 mL) was added. The mixture was acidified to pH 4 using 2 M HCl and extracted with EtOAc (3×200 mL). The combined EtOAc layers were dried over MgSO$_4$ and concentrated. The resulting residue was dissolved in 4.0 M HCl in dioxane (75 mL). After 45 minutes the mixture was concentrated then reconcentrated from toluene (200 mL).

The above residue was dissolved in anhydrous DMF (75 mL). To this solution was added NaHCO$_3$ (6.50 g, 77.0 mmole) and triethylamine (4.3 mL, 30.8 mmole) at RT. The mixture was cooled to 0° C. and diphenylphosphoryl azide (5 mL, 23.1 mmole) was added. After 16 hr the mixture was concentrated. The resulting paste was dissolved in EtOAc (500 mL), washed with H$_2$O (2×300 mL), dried over MgSO$_4$, and concentrated. Flash silica gel chromatography (40% EtOAc/hexanes) gave the title compound (2.61 g, 33% from [R-(R*, S*)]-methyl β-[[4-methoxy-2-[[[(1,1-dimethylethoxy)carbonyl](2-phenylethyl)amino]methyl]phenyl]methyl]-γ-oxo-4-phenylethyl)-3-oxazolidinebutanoate) as a clear oil: MS (ES) m/e 390 (M+Na)$^+$.

f) Methyl (S)-8-hydroxy-3-oxo-2-(2-phenylethyl)-2,3,4,5-tetrahydro-1H-2-benzazepine-4-acetate To a solution of methyl (S)-8-methoxy-3-oxo-2-(2-phenylethyl)-2,3,4,5-tetrahydro-1H-2-benzazepine-4-acetate (2.61 g, 7.1 mmole) in CH$_2$Cl$_2$ (40 mL) was added BBr$_3$ (21.3 mL, 1M in CH$_2$Cl$_2$, 21.3 mmole) at −20° C. After 45 minutes the mixture was quenched with MeOH (200 mL) and concentrated. The residue was filtered through a silica gel plug using 50% EtOAc/hexanes as eluent. The resulting orange solid was recrystallized from MeOH/H$_2$O to give the title compound as an off-white solid (2.16 g, 81%): MS (ES) m/e 376 (M+Na)$^+$.

Example 1

Preparation of (±)-8-[3-(2-pyridylamino)-1-propyloxy]-3-oxo-2,3,4,5-tetrahydro-1H-2-benzazepine-4-acetic acid a) Methyl (±)-8-[3-[2-(N-oxopyridyl)amino]-1-propyloxy]-3-oxo-2,3,4,5-tetrahydro-1H-2-benzazepine-4-acetic acid A solution of 2-[(3-hydroxy-1-propyl)amino]pyridine-N-oxide (1.4 g, 8 mmol) in anhydrous DMF (8 mL) was added dropwise to a solution of methyl (±)-8-hydroxy-3-oxo-2,3,4,5-tetrahydro-1H-2-benzazepine-4-acetate (1.7 g, 7 mmole), triphenylphosphine (2.76 g, 11 mmol), and diethyl azodicarboxylate (2.33 mL, 14 mmole) in anhydrous DMF (4 mL) and dry THF (10 mL) at RT under argon. The resulting solution was stirred for 18 hr, then was concentrated under vacuum. Silica gel chromatography (2%–10% CH$_3$OH/CH$_2$Cl$_2$) to give the title compound (1.2 g): MS (ES) m/e 400.2 (M+H)$^+$. Unreacted methyl (±)-8-hydroxy-3-oxo-2,3,4,5-tetrahydro-1H-2-benzazepine-4-acetate (0.4 g) was also recovered.

b) Ethyl (±)-8-[3-(2-pyridylamino)-1-propyloxy]-3-oxo-2,3,4,5-tetrahydro-1H-2-benzazepine-4-acetate A mixture of methyl (±)-8-[3-[2-(N-oxopyridyl)amino]-1-propyloxy]-3-oxo-2,3,4,5-tetrahydro-1H-2-benzazepine-4-acetate (1.2 g, 3 mmol), 1.2 g 10% palladium on charcoal (1.2 g), cyclohexene (3 mL, 15 mmol), and ethanol (20 mL) was heated at reflux for 18 hr. The mixture was filtered and the filtrate was concentrated. The residue was purified by chromatography on silica gel (2%–5% CH$_3$OH/CH$_2$Cl$_2$)to give the title compound (0.72 g, 64%) as a white foam: MS (ES) m/e 398.2 (M+H)$^+$.

c) (±)-8-[3-(2-Pyridylamino)-1-propyloxy]-3-oxo-2,3,4,5-tetrahydro-1H-2-benzazepine-4-acetic acid A mixture of ethyl (±)-8-[3-(2-pyridylamino)-1-propyloxy]-3-oxo-2,3,4,5-tetrahydro-1H-2-benzazepine-4-acetate (0.7 g, 2 mmol), lithium hydroxide monohydrate (0.12 g, 3 mmol), 5 mL THF (5 mL), H$_2$O (5 mL), and MeOH (2 mL) was stirred at room temperature for 18 hr, then was then concentrated. The residue was partitioned between ethyl acetate and water, and the layers were separated. The aqueous phase was cautiously brought to pH 4 with 3 N HCl and allowed to stand. The resulting crystals were collected by filtration and dried to give the title compound (0.4 g, 65%) as a tan solid: MS m/e 370.4 (M+H)$^+$. Anal. Calcd for C$_{20}$H$_{23}$N$_3$O$_4$.0.25 H$_2$O: C, 64.25; H, 6.34; N, 11.24. Found: C, 64.02; H, 6.37; N, 11.20.

Example 2

Preparation of (±)-8-[3-[(4-amino-2-pyridyl)amino]-1-propyloxy]-3-oxo-2,3,4,5-tetrahydro-1H-2-benzazepine-4-acetic acid a) Methyl (±)-8-[3-[2-(4-nitro-N-oxopyridyl)amino]-1-propyloxy]-3-oxo-2,3,4,5-tetrahydro-1H-2-benzazepine-4-acetate According to the procedure of Example 1(a), except substituting 2-[(3-hydroxy-1-propyl)amino]-4-nitropyridine-N-oxide for the 2-[(3-hydroxy-1H-propyl)amino]pyridine-N-oxide, the title compound was prepared as an orange foam: MS (ES) m/e 445.2 (M+H)$^+$.

b) Methyl (±)-8-[3-[(4-amino-2-pyridyl)amino]-1-propyloxy]-3-oxo-2,3,4,5-tetrahydro-1H-2-benzazepine-4-acetate According to the procedure of Example 1(b), except substituting methyl (±)-8-[3-[2-(4-nitro-N-oxopyridyl)amino]-1-propyloxy]-3-oxo-2,3,4,5-tetrahydro-1H-2-benzazepine-4-acetate for the methyl (±)-8-[3-[2-(N-oxopyridyl)amino]-1-propyloxy]-3-oxo-2,3,4,5-tetrahydro-1H-2-benzazepine-4-acetate, the title compound was prepared as a white foam: MS (ES) m/e 399.3 (M+H)$^+$.

c) (±)-8-[3-[(4-Amino-2-pyridyl)amino]-1-propyloxy]-3-oxo-2,3,4,5-tetrahydro-1H-2-benzazepine-4-acetic acid According to the procedure of Example 1(c), except substituting methyl (±)-8-[3-[(4-amino-2-pyridyl)amino]-1-propyloxy]-3-oxo-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the title compound was prepared as a white solid: MS (ES) m/e 385.4 (M+H)$^+$. Anal. Calcd for C$_{20}$H$_{24}$N$_4$O$_4$.1.25 H$_2$O: C, 59.03; H, 6.56; N, 13.76. Found: C, 58.80; H, 6.49; N, 13.62.

Example 3

Preparation of (±)-8-[3-[(4-methoxy-2-pyridyl)amino]-1-propyloxy]-3-oxo-2,3,4,5-tetrahydro-1H-2-benzazepine-4-acetic acid a) Methyl (±)-8-[3-[2-(4-methoxy-N-oxopyridyl)amino]-1-propyloxy]-3-oxo-2,3,4,5-tetrahydro-1H-2-benzazepine-4-acetate According to the procedure of Example 1(a), except substituting 2-[(3-hydroxy-1-propyl)amino]-4-methoxypyridine-N-oxide for the 2-[(3-hydroxy-1H-propyl)amino]pyridine-N-oxide, the title compound was prepared as a colorless oil: MS (ES) m/e 430.3 (M+H)$^+$.

b) Methyl (±)-8-[3-[(4-methoxy-2-pyridyl)amino]-1-propyloxy]-3-oxo-2,3,4,5-tetrahydro-1H-2-benzazepine-4-acetate According to the procedure of Example 1(b), except substituting methyl (±)-8-[3-[2-(4-methoxy-N-oxopyridyl)amino]-1-propyloxy]-3-oxo-2,3,4,5-tetrahydro-1H-2-benzazepine-4-acetate for the methyl (±)-8-[3-[2-(N-oxopyridyl)amino]-1-propyloxy]-3-oxo-2,3,4,5-tetrahydro-1H-2-benzazepine-4-acetate, the title compound was prepared as a pale yellow oil: MS (ES) m/e 414.4 (M+H)$^+$.

c) (±)-8-[3-[(4-Methoxy-2-pyridyl)amino]-1-propyloxy]-3-oxo-2,3,4,5-tetrahydro-1H-2-benzazepine-4-acetic acid According to the procedure of Example 1(c), except substituting methyl (±)-8-[3-[(4-methoxy-2-pyridyl)amino]-1-propyloxy]-3-oxo-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the title compound was prepared as an off-white solid: MS (ES) m/e 400.3 (M+H)$^+$. Anal. Calcd for C$_{21}$H$_{25}$N$_3$O$_5$·0.75 H$_2$O: C, 61.08; H, 6.47; N, 10.18. Found: C, 61.15; H, 6.20; N, 10.12.

Example 4

Preparation of (±)-8-[3-(2-pyridylamino)-1-propyloxy]-2-methyl-3-oxo-2,3,4,5-tetrahydro-1H-2-benzazepine-4-acetic acid a) Methyl (±)-8-[3-[2-(N-oxopyridyl)amino]-1-propyloxy]-2-methyl-3-oxo-2,3,4,5-tetrahydro-1H-2-benzazepine-4-acetate A solution of 2-[(3-hydroxy-1-propyl)amino]pyridine-N-oxide (252.3 mg, 1.5 mmole) and diethyl azodicarboxylate (0.24 mL, 1.5 mmole) in anhydrous DMF (7.5 mL) was added slowly dropwise to a solution of methyl (±)-8-hydroxy-2-methyl-3-oxo-2,3,4,5-tetrahydro-1H-2-benzazepine-4-acetate (197.5 mg, 0.75 mmole) and triphenylphosphine (413.1 mg, 1.58 mmole) in anhydrous DMF (7.5 mL) at RT. The addition required 15 min, and was mildly exothermic. After 2 hr, the reaction was concentrated and the residue was reconcentrated from xylenes. Silica gel chromatography (2:2:1 EtOAc/CHCl$_3$/MeOH) gave the R$_f$ 0.48 (TLC in 2:2:1 EtOAc/CHCl$_3$/MeOH) material as a cloudy, nearly colorless oil. This was rechromatographed on silica gel (absolute EtOH) to afford the title compound (243.9 mg, 79%) as an off-white foam: TLC (absolute EtOH) R$_f$ 0.33; $^1$H NMR (250, CDCl$_3$) δ 8.12 (app. dd, 1H), 7.10–7.23 (m, 1 H), 6.90–7.10 (m, 2 H), 6.78 (dd, J=8.4, 2.6 Hz, 1 H), 6.45–6.72 (m, 3 H), 5.28 (d, J=16.3 Hz, 1H), 3.95–4.25 (m, 2 H), 3.60–3.90 (m, 1 H), 3.76 (d, J=16.3 Hz, 1 H), 3.71 (s, 3 H), 3.51 (q, J=6.4 Hz, 2 H), 2.73–3.15 (m, 3 H), 3.04 (s, 3 H), 2.41 (dd, J=16.7, 5.4 Hz, 1 H), 2.05–2.28 (m, 2 H); MS (ES) m/e 414 (M+H)$^+$.

b) Methyl (±)-8-[3-(2-pyridylamino)-1-propyloxy]-2-methyl-3-oxo-2,3,4,5-tetrahydro-1H-2-benzazepine-4-acetate A mixture of methyl (±)-8-[3-[2-(N-oxopyridyl)amino]-1-propyloxy]-2-methyl-3-oxo-2,3,4,5-tetrahydro-1H-2-benzazepine-4-acetate (243.9 mg, 0.59 mmole), cyclohexene (0.60 mL, 5.9 mmole), and 10% Pd/C (63 mg, 0.06 mmole) in 2-propanol (6 mL) was heated at reflux. After 21.5 hr, the reaction was cooled to RT and filtered through celite®. The filtrate was concentrated, and the residue was reconcentrated from toluene. Silica gel chromatography (5% MeOH in 1:1 EtOAc/CHCl$_3$) gave the title compound (212.8 mg, 91%) as a colorless oil: TLC (5% MeOH in 1:1 EtOAc/CHCl$_3$) R$_f$ 0.39; $^1$H NMR (250, CDCl$_3$) δ 8.03–8.13 (m, 1 H), 7.35–7.48 (m, 1 H), 7.00 (d, J=8.4 Hz, 1 H), 6.77 (dd, J=8.4, 2.5 Hz, 1 H), 6.63 (d, J=2.5 Hz, 1 H), 6.52–6.62 (m, 1 H), 6.40 (d, J=8.5 Hz, 1 H), 5.27 (d, J=16.3 Hz, 1 H), 4.62–4.82 (m, 1 H), 3.95–4.20 (m, 2 H), 3.60–3.90 (m, 2 H), 3.71 (s, 3 H), 3.50 (q, J=6.3 Hz, 2 H), 2.75–3.15 (m, 3 H), 3.03 (s, 3 H), 2.40 (dd, J=16.7, 5.3 Hz, 1 H), 2.00–2.22 (m, 2 H); MS (ES) m/e 398 (M+H)$^+$.

c) (±)-8-[3-(2-Pyridylamino)-1-propyloxy]-2-methyl-3-oxo-2,3,4,5-tetrahydro-1H-2-benzazepine-4-acetic acid 1.0 N LiOH (0.80 mL, 0.80 mmole) was added to a solution of methyl (±)-8-[3-(2-pyridylamino)-1-propyloxy]-2-methyl-3-oxo-2,3,4,5-tetrahydro-1H-2-benzazepine-4-acetate (207.5 mg, 0.52 mmole) in THF (2.6 mL) and H$_2$O (1.8 mL) at RT. The initially cloudy solution became homogeneous within 1 min. After 18 hr, the reaction was acidified with TFA (0.12 mL, 1.56 mmole) and concentrated. ODS chromatography (20% CH$_3$CN/H$_2$O containing 0.1% TFA), concentration, and lyophilization gave the title compound (252.4 mg, 83%) as a light yellow, hygroscopic solid: HPLC (PRP-1®, 20% CH$_3$CN/H$_2$O containing 0.1% TFA) K'=2.4; $^1$H NMR (400 MHz, CD$_3$OD) δ 7.83–7.93 (m, 1 H), 7.76–7.83 (m, 1 H), 7.00–7.11 (m, 2 H), 6.83–6.91 (m, 1 H), 6.80 (dd, J=8.4, 2.6 Hz, 1 H), 6.76 (d, J=2.6 Hz, 1 H), 5.30 (d, J=16.5 Hz, 1 H), 4.05–4.18 (m, 2 H), 3.94 (d, J=16.5 Hz, 1 H), 3.77–3.90 (m, 1 H), 3.57 (t, J=6.8 Hz, 2 H), 3.03 (dd, J=17.0, 4.2 Hz, 1 H), 2.99 (s, 3 H), 2.83 (dd, J=17.0, 9.1 Hz, 1 H), 2.72 (dd, J=17.0, 13.5 Hz, 1 H), 2.44 (dd, J=17.0, 4.7 Hz, 1 H), 2.11–2.23 (m, 2 H); MS (ES) m/e 384 (M+H)$^+$. Anal. Calcd for C$_{21}$H$_{25}$N$_3$O$_4$·1.5 CF$_3$CO$_2$H·1.5 H$_2$O: C, 49.57; H, 5.11; N, 7.23. Found: C, 49.65; H, 4.95; N, 7.15.

Example 5

Preparation of (±)-8-[3-(2-imidazolylamino)-1-propyloxy]-3-oxo-2,3,4,5-tetrahydro-1H-2-benzazepine-4-acetic acid The title compound is prepared generally following the procedures detailed in Examples 1–4.

Example 6

Preparation of (±)-8-[3-[2-(1,4,5,6-tetrahydropyrimidinyl)amino]-1-propyloxy]-3-oxo-2,3,4,5-tetrahydro-1H-2-benzazepine-4-acetic acid a) Methyl (±)-8-[3-(tert-butoxycarbonylamino)-1-propyloxy]-3-oxo-2,3,4,5-tetrahydro-1H-2-benzazepine-4-acetate A solution of 3-[(tert-butoxycarbonyl)amino]-1-propanol (0.14 g, 0.8 mmol) and diethyl azodicarboxylate (0.13 mL, 0.8 mmole) in anhydrous DMF (2 mL) was added dropwise to a solution of methyl (±)-8-hydroxy-3-oxo-2,3,4,5-tetrahydro-1H-2-benzazepine-4-acetate (0.10 g, 0.4 mmole) and triphenylphosphine (0.21 g, 0.8 mmol) in anhydrous DMF (1.4 mL) and dry THF (2 mL) at RT under argon. The resulting solution was stirred for 18 hr, then was concentrated under vacuum. Silica gel chromatography (1%–3% MeOH/CH$_2$Cl$_2$) gave the title compound (0.11 g): MS (ES) m/e 407.3 (M+H)$^+$.

b) Methyl (±)-8-(3-amino-1-propyloxy)-3-oxo-2,3,4,5-tetrahydro-1H-2-benzazepine-4-acetate, trifluoroacetate salt A solution of methyl (±)-8-[3-(tert-butoxycarbonylamino)-1-propyloxy]-3-oxo-2,3,4,5-tetrahydro-1H-2-benzazepine-4-acetate (0.70 g) in CH$_2$Cl$_2$ (7 mL) and TFA (2 mL) was stirred under argon at 0° C. for 1 hr, then was concentrated to give the title compound (0.75 g, 100%) as a colorless glass: MS (ES) m/e 321.4 (M+H)$^+$.

c) Methyl (±)-8-[3-(pyrimidin-2-ylamino)-1-propyloxy]-3-oxo-2,3,4,5-tetrahydro-1H-2-benzazepine-4-acetate A mixture of methyl (±)-8-(3-amino-1-propyloxy)-3-oxo-2,3,4,5-tetrahydro-1H-2-benzazepine-4-acetate trifluoroacetate salt (0.75 g, 2 mmol), 2-bromopyrimidine (0.5 g, 3 mmol), NaHCO$_3$ (1.4 g, 17 mmol), and EtOH (10 mL) was heated to reflux. After 24 hr, the mixture was filtered and the insoluble material was washed with MeOH. The filtrate and washings were combined and concentrated, and the residue was purified by chromatography on silica gel (1%–6% MeOH/CH$_2$Cl$_2$) to give the title compound (0.54 g, 82%) as a white foam: MS (ES) m/e 385.5 (M+H)$^+$.

d) (±)-8-[3-[(1,4,5,6-Tetrahydropyrimidin-2-yl)amino]-1-propyloxy]-3-oxo-2,3,4,5-tetrahydro-1H-2-benzazepine-4-acetic acid A mixture of methyl (±)-8-[3-(pyrimidin-2-ylamino)-1-propyloxy]-3-oxo-2,3,4,5-tetrahydro-1H-2-benzazepine-4-acetate (0.36 g, 0.94 mmol), 4 M HCl in dioxane (0.25 mL, 1 mmol), 10% palladium on charcoal (0.24 g, 0.24 mmol), and MeOH (5 mL) was stirred under a balloon of hydrogen. After 18 hr, the mixture was filtered and the filtrate was concentrated. The residue was partitioned between EtOAc and aqueous K$_2$CO$_3$. A solid precipitated, which was collected by filtration and dried to give the title compound as a white solid: MS m/e 375.4 (M+H)$^+$. Anal. Calcd for C$_{19}$H$_{26}$N$_4$O$_4$·2.5 H$_2$O: C, 54.40; H, 7.45; N, 13.35. Found: C, 54.68; H, 7.12; N, 13.39.

Example 7
Preparation of (±)-8-[3-(6-amino-2-pyridylamino-1-propyloxy]-3-oxo-2,3,4,5-tetrahydro-1H-2-benzazepine-4-acetic acid The title compound is prepared generally following the procedures detailed in Examples 1–4.

Example 8
Preparation of (±)-8-[2-[6-(methylamino)pyridyl]ethoxy]-3-oxo-2,3,4,5-tetrahydro-1H-2-benzazepine-4-acetate acid a) Methyl (±)-8-[2-[6-(methylamino)pyridin-2-yl]-1-ethoxy]-3-oxo-2,3,4,5-tetrahydro-1H-2-benzazepine-4-acetic acid According to the procedure of Example 1(a), except substituting 6-(methylamino)-2-pyridylethanol for the 2-[(3-hydroxy-1H-propyl)amino]pyridine-N-oxide, the title compound was prepared as a white foam: MS (ES) m/e 384 (M+H)$^+$.

b) (±)-8-[2-[6-(Methylamino)pyridin-2-yl]-1-ethoxy]-3-oxo-2,3,4,5-tetrahydro-1H-2-benzazepine-4-acetic acid According to the procedure of Example 1(c), except substituting methyl (±)-8-[2-[6-(methylamino)pyridin-2-yl]-1-ethoxy]-3-oxo-2,3,4,5-tetrahydro-1H-2-benzazepine-4-acetate methyl for the ethyl (±)-8-[3-[2-pyridylamino-1-propyloxy]-3-oxo-2,3,4,5-tetrahydro-1H-2-benzodiazepine-4-acetate, the title compound was prepared as a white solid: MS (ES) m/e 370 (M+H)$^+$.

Example 9
Preparation of (±)-8-[2-(2-benzimidazolyl)ethoxy]-3-oxo-2,3,4,5-tetrahydro-1H-2-benzazepine-4-acetic acid a) Methyl (±)-8-[2-(benzimidazol-2-yl)-1-ethoxy]-3-oxo-2,3,4,5-tetrahydro-1H-2-benzazepine-4-acetate According to the procedure of Example 1(a), except substituting 2-(benzimidazol-2-yl)-1-ethanol for the 2-[(3-hydroxy-1-propyl)amino]pyridine-N-oxide, the title compound was prepared as an off white solid: MS (ES) m/e 394.4 (M+H)$^+$, 416.3 (M+Na)$^+$.

b) (±)-8-[2-(Benzimidazol-2-yl)-1-ethoxy]-3-oxo-2,3,4,5-tetrahydro-1H-2-benzazepine-4-acetic acid According to the procedure of Example 1(c), except substituting methyl (±)-8-[2-(benzimidazol-2-yl)-1-ethoxy]-3-oxo-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the title compound was prepared as a white powder: MS (ES) m/e 380.4 (M+H)$^+$, 402.3 (M+Na)$^+$.

Example 10
Preparation of (±)-8-[2-(4-aza-2-benzimidazolyl)ethoxy]-3-oxo-2,3,4,5-tetrahydro-1H-2-benzazepine-4-acetic acid The title compound is prepared generally following the procedures detailed in Example 9.

Example 11
Preparation of (±)-3-oxo-8-[3-(pyridin-2-ylamino)-1-propyloxy]-2-(2,2,2-trifluoroethyl)-2,3,4,5-tetrahydro-1H-2-benzazepine-4-acetic acid a) Methyl (±)-3-oxo-8-[3-(1-oxopyridin-2-ylamino)-1-propyloxy]-2-(2,2,2-trifluoroethyl)-2,3,4,5-1H-2-benzazepine-acetate A solution of 2-[(3-hydroxy-1H-propyl)amino]pyridine-N-oxide (252.3 mg, 1.5 mmole) and diethyl azodicarboxylate (0.24 mL, 1.5 mmole) in anhydrous DMF (7.5 mL) was added slowly dropwise over 3–4 min to a solution of methyl (±)-8-hydroxy-3-oxo-2-(2,2,2-trifluoroethyl)-2,3,4,5-tetrahydro-1H-2-benzazepine-4-acetate (248.5 mg, 0.75 mmole) and triphenylphosphine (413.1 mg, 1.58 mmole) in anhydrous DMF (7.5 mL) at RT. After 17 hr, the reaction was concentrated and the residue was reconcentrated from xylenes/CHCl$_3$. Silica gel chromatography (gradient: EtOAc (500 mL) then 5% MeOH/CHCl$_3$) gave the title compound (253.6 mg, 70%) as an off-white foam: $^1$H NMR (250, CDCl$_3$) δ 8.11 (dd, J=6.4, 1.4 Hz, 1 H), 7.10–7.23 (m, 1 H), 6.93–7.10 (m, 2 H), 6.81 (dd, J=8.4, 2.6 Hz, 1 H), 6.45–6.70 (m, 3 H), 5.34 (d, J=16.7 Hz, 1 H), 3.75–4.30 (m, 6 H), 3.71 (s, 3 H), 3.51 (q, J=6.4 Hz, 2 H), 2.80–3.15 (m, 3 H), 2.46 (dd, J=16.8, 5.5 Hz, 1 H), 2.07–2.28 (m, 2 H); MS (ES) m/e 482.2 (M+H)$^+$.

b) Methyl (±)-3-oxo-8-[3-(pyridin-2-ylamino)-1-propyloxy]-2-(2,2,2-trifluoroethyl)-2,3,4,5-tetrahydro-1H-2-benzazepine-4-acetate A mixture of methyl (±)-3-oxo-8-[3-(1-oxopyridin-2-ylamino)-1-propyloxy]-2-(2,2,2-trifluoroethyl)-2,3,4,5-tetrahydro-1H-2-benzazepine-4-acetate (253.6 mg, 0.53 mmole), cyclohexene (0.54 mL, 5.3 mmole), palladium black (11.3 mg, 0.11 mmole), and isopropanol (5.3 mL) was heated to reflux. After 0.5 hr, 10% Pd/C (28.2 mg, 0.03 mmole) was added, and after 1.45 hr, Pd black (11.3 mg, 0.11 mmole) and cyclohexene (0.27 mL, 2.65 mmole) were added. After an additional 48 hr, the reaction was hot-filtered through celite®, and the filter pad was washed with hot 1:1 MeOH/CHCl$_3$. Concentration and reconcentration from xylenes left a yellow oil. Silica gel chromatography (5% MeOH in 1:1 EtOAc/CHCl$_3$) gave the title compound (194.0 mg, 79%) as a light yellow oil: TLC (5% MeOH in 1:1 EtOAc/CHCl$_3$) R$_f$ 0.53; $^1$H NMR (250, CDCl$_3$) δ 8.08 (dd, J=5.0, 1.0 Hz, 1 H), 7.37–7.48 (m, 1 H), 7.02 (d, J=8.4 Hz, 1 H), 6.79 (dd, J=8.4, 2.5 Hz, 1 H), 6.63 (d, J=2.5 Hz, 1 H), 6.52–6.62 (m, 1 H), 6.40 (d, J=8.4 Hz, 1 H), 5.34 (d, J=16.6 Hz, 1 H), 4.60–4.80 (m, 1 H), 3.75–4.30 (m, 6 H), 3.71 (s, 3H), 3.50 (q, J=6.4 Hz, 2 H), 2.80–3.15 (m, 3 H), 2.46 (dd, J=16.8, 5.4 Hz, 1 H), 2.00–2.25 (m, 2 H); MS (ES) m/e 466 (M+H)$^+$.

c) (±)-3-Oxo-8-[3-(pyridin-2-ylamino)-1-propyloxy]-2-(2,2,2-trifluoroethyl)-2,3,4,5-tetrahydro-1H-2-benzazepine-4-acetic acid 1.0 N LiOH (0.44 mL, 0.44 mmole) was added to a solution of methyl (±)-8-[3-(2-pyridylamino)-1-propyloxy]-3-oxo-2-(2,2,2-trifluoroethyl)-2,3,4,5-tetrahydro-1H-2-benzazepine-4-acetate (159.5 mg, 0.34 mmole) in THF (1.7 mL) and H$_2$O (1.3 mL) at RT. The yellow, cloudy reaction became homogeneous within 10 min. After 24 hr, the reaction was concentrated to dryness and the yellow residue was dissolved in H$_2$O (4 mL). The solution was filtered, then was carefully neutralized (pH≈7) with 1.0 N HCl. The precipitate was collected, washed with plenty of H$_2$O, and dried in high vacuum at 40–45° C. to afford the title compound (130.0 mg, 83%) as an off-white solid: HPLC (PRP-1®, 25% CH$_3$CN/H$_2$O containing 0.1% TFA) k'=3.1; $^1$H NMR (400 MHz, DMSO-d$_6$) δ 7.91–8.00 (m, 1 H), 7.28–7.40 (m, 1 H), 7.02 (d, J=9.2 Hz, 1 H), 6.76–6.87 (m, 2 H), 6.51–6.02 (m, 1 H), 6.39–6.50 (m, 2 H), 5.30 (d, J=16.6 Hz, 1 H), 4.10–4.30 (m, 3 H), 4.02(t, J=6.3 Hz, 1 H), 3.70–3.82 (m, 1 H), 3.20–3.45 (m, 2 H, partially obscured by residual solvent signal), 2.99 (dd, 1 H), 2.59–2.74 (m, 2 H), 2.39 (dd, J=16.9, 4.8 Hz, 1 H), 1.90–2.03 (m, 2 H); MS (ES) m/e 452 (M+H)$^+$. Anal. Calcd for C$_{22}$H$_{24}$F$_3$N$_3$O$_4$.0.5 H$_2$O: C, 57.39; H. 5.47; N, 9.13. Found: C, 57.39; H, 5.18; N, 9.00.

Example 12
Preparation of (±)-8-[3-(4,6-dimethylpyridin-2-ylamino)-1-propyloxy]-2-methyl-3-oxo-2,3,4,5-tetrahydro-1H-benzazepine-4-acetic acid a) Methyl (±)-8-[3-(4,6-dimethyl-1-oxopyridin-2-ylamino)-1-propyloxy]-2-methyl-3-oxo-2,3,4,5-tetrahydro-1H-benzazepine-4-acetate According to the procedure of Example 1(a), except substituting 2-[(3-hydroxy-1-propyl)amino]-4,6-dimethylpyridine-N-oxide for the 2-[(3-hydroxy-1-amino]pyridine-N-oxide, the title compound was prepared as white foam: MS (ES) m/e 442.3 (M+H)+.

b) Methyl (±)-8-[3-(4,6-dimethylpyridin-2-ylamino]-1-propyloxy]-2-methyl-3-oxo-2,3,4,5-tetrahydro-1H-2-benzazepine-4-acetate According to the procedure of Example 1(b), except substituting methyl (±)-8-[3-(4,6-dimethyl-1-oxopyridin-2-ylamino)-1-propyloxy]-2-methyl-3-oxo-2,3,4,5-tetrahydro-1H-2-benzazepine-4-acetate for the methyl (±)-8-[3-[2-(N-oxopyridyl)amino]-1-propyloxy]-3-oxo-2,3,4,5-tetrahydro-2-benzazepine-4-acetate, the title compound was prepared as a pale yellow solid: MS (ES) m/e 426.3 (M+H)+.

c) (±)-8-[3-(4,6-Dimethylpyridin-2-ylamino)-1-propyloxy]-2-methyl-3-oxo-2,3,4,5-tetrahydro-1H-2-benzazepine-4-acetic acid According to the procedure of Example 1(c), except substituting methyl (±)-8-[3-[(4,6-dimethylpyridin-2-yl)amino]-1-propyloxy]-2-methyl-3-oxo-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the title compound was prepared as a white solid: MS (ES) m/e 412.2 (M+H)+. Anal. Calcd for $C_{23}H_{29}N_3O_4 \cdot 0.5$ HCl. 0.25 $H_2O$: C, 63.62; H, 6.96; N, 9.68. Found: C, 63.62; H, 6.96; N, 9.69.

Example 13

Preparation of (±)-8-[2-(2-aminothiazol-4-yl)-1-ethoxy]-2-methyl-3-oxo-2,3,4,5-tetrahydro-1H-2-benzazepine-4-acetic acid a) Methyl (±)-8-[2-(2-aminothiazol-4-yl)-1-ethoxy]-2-methyl-3-oxo-2,3,4,5-tetrahydro-1H-2-benzazepine-4-acetate According to the procedure of Example 1(a), except substituting 2-(2-aminothiazol-4-yl)ethanol (WO 95/32710) for the 2-[(3-hydroxy-1H-propyl)amino]pyridine-N-oxide, the title compound was prepared as white foam: MS (ES) m/e 390 (M+H)+.

b) (±)-8-[2-(2-Aminothiazol-4-yl)-1H-ethoxy]-2-methyl-3-oxo-2,3,4,5-tetrahydro-1H-2-benzazepine-4-acetic acid According to the procedure of Example 1(c) except substituting methyl (±)-8-[2-(2-aminothiazol-4-yl)-1-ethoxy]-2-methyl-3-oxo-2,3,4,5-tetrahydro-1H-2-benzazepine-4-acetate for the ethyl (±)-8-[3-(2-pyridylamino-1-propyloxy)-3-oxo-2,3,4,5-tetrahydro-1H-2-benzazepine-4-acetate, the title compound was prepared as a white solid: MS (ES) m/e 376 (M+H)+. Anal. Calcd for $C_{18}H_{21}N_3O_4S \cdot 1.3$ $CF_3CO_2H \cdot 0.36$ $H_2O$: C, 46.62; H, 4.38; N, 7.93. Found: C, 46.45; H 4.57; N, 8.27.

Example 14

Preparation of (±)-8-[3-(4-aminopyridin-2-ylamino)-1-propyloxy]-2-methyl-3-oxo-2,3,4,5-tetrahydro-1H-2-benzazepine-4-acetic acid a) Methyl (±)-8-[3-(4-nitro-1-oxopyridin-2-ylamino)-1-propyloxy]-2-methyl-3-oxo-2,3,4,5-tetrahydro-1H-2-benzazepine-4-acetate According to the procedure of Example 1(a), except substituting 2-[(3-hydroxy-1-propyl)amino]-4-nitropyridine-N-oxide for the 2-[(3-hydroxy-1-propyl)amino]pyridine-N-oxide and substituting methyl (±)-8-hydroxy-2-methyl-3-oxo-2,3,4,5-tetrahydro-1H-2-benzazepine-4-acetate for the methyl (±)-8-hydroxy-3-oxo-2,3,4,5-tetrahydro-1H-2-benzazepine-4-acetate, the title compound was prepared: MS (ES) m/e 459 (M+H)+.

b) Methyl (±)-8-[3-(4-aminopyridin-2-ylamino)-1-propyloxy]-2-methyl-3-oxo-2,3,4,5-tetrahydro-1H-2-benzazepine-4-acetate According to the procedure of Example 1(b), except substituting methyl (±)-8-[3-(4-nitro-1-oxopyridin-2-ylamino-1-propyloxy]-2-methyl-3-oxo-2,3,4,5-tetrahydro-1H-2-benzazepine-4-acetate for the methyl (±)-8-[3-(4-nitro-N-oxopyridin-2-ylamino)-1-propyloxy]-3-oxo-2,3,4,5-tetrahydro-1H-2-benzazepine-4-acetate, the title compound was prepared as a white foam: MS (ES) m/e 413 (M+H)+.

b) (±)-8-[3-(4-Aminopyridin-2-ylamino)-1-propyloxy]-2-methyl-3-oxo-2,3,4,5-tetrahydro-1H-2-benzazepine-4-acetic acid According to the procedure of Example 1(c), except substituting methyl (±)-8-[3-(4-aminopyridin-2-ylamino)-1-propyloxy]-2-methyl-3-oxo-2,3,4,5-tetrahydro-1H-2-benzazepine-4-acetate for the ethyl (±)-8-[3-[2-pyridylamino)-1-propyloxy]-3-oxo-2,3,4,5-tetrahydro-1H-2-benzazepine-4-acetate, the title compound was prepared as a white solid: MS (ES) m/e 399 (M+H)+. Anal. Calcd for $C_{21}H_{26}N_4O_4 \cdot 1.5CF_3CO_2H \cdot 0.125H_2O$: C, 50.62: H, 4.91; N, 9.83. Found: C, 50.63; H 5.26; N, 9.90.

Example 15

Preparation of (±)-8-[3-(Pyrimidin-2-ylamino)-1-propyloxy]-3-oxo-2,3,4,5-tetrahydro-1H-2-benzazepine-4-acetic acid A mixture of methyl (±)-8-[3-(pyrimidin-2-ylamino)-1-propyloxy]-3-oxo-2,3,4,5-tetrahydro-1H-2-benzazepine-4-acetate (0.071 g, 0:18 mmol) and lithium hydroxide monohydrate (0.009 g, 2 mmol) in THF (5 mL) and $H_2O$ (2 mL) was stirred at room temperature for 18 hr, then was concentrated. The residue was dissolved in $H_2O$ and the pH was adjusted to 4 with 3 N HCl. The resulting solid was collected by filtration and dried to give the title compound (0.05 g, 73%) as a white solid: MS m/e 371.4 (M+H)+. Anal. Calcd for $C_{19}H_{22}N_4O_4 \cdot 0.5$ $H_2O$: C, 60.15; H, 6.11; N, 14.77. Found: C, 60.14; H, 6.06; N, 14.71.

Example 16

Preparation of (R)-8-[3-[(4-amino-2-pyridyl)amino]-1-propyloxy]-3-oxo-2,3,4,5-tetrahydro-1H-2-benzazepine-4-acetic acid a) Methyl (R)-8-[3-[2-(4-nitro-1H-oxopyridyl)amino]-1-propyloxy]-3-oxo-2,3,4,5-tetrahydro-1H-2-benzazepine-4-acetate According to the procedure of Example 1(a), except substituting 2-[(3-hydroxy-1propyl)amino]-4-nitropyridine-N-oxide for the 2-[(3-hydroxy-1H-propyl)amino]pyridine-N-oxide, the title compound was prepared as an orange foam: MS (ES) m/e 445.3 (M+H)+.

b) Methyl (R)-8-[3-[(4-amino-2-pyridyl)amino]-1-propyloxy]-3-oxo-2,3,4,5-tetrahydro-1H-2-benzazepine-4-acetate According to the procedure of Example 1(b), except substituting methyl (R)-8-[3-[2-(4-amino-N-oxopyridyl)amino]-1-propyloxy]-3-oxo-2,3,4,5-tetrahydro-1H-2-benzazepine-4-acetate for the methyl (±)-8-[3-[2-(N-oxopyridyl)amino]-1-propyloxy]-3-oxo-2,3,4,5-tetrahydro-1H-2-benzazepine-4-acetate, the title compound was prepared a white foam: MS (ES) m/e 399.4 (M+H)+.

c) (R)-8-[3-[(4-amino-2-pyridyl)amino]-1-propyloxy]-3-oxo-2,3,4,5-tetrahydro-1H-2-benzazepine-4-acetic acid According to the procedure of Example 1(c), except substituting methyl (R)-8-[3-[(4-amino-2-pyridyl)amino]-1-propyloxy]-3-oxo-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the title compound was prepared as an off-white solid: $[\alpha]_D^{23}$+74.97° (c 1.45, MeOH); MS (ES) m/e 385.4

(M+H)+. Anal. Calcd for C<sub>20</sub>H<sub>24</sub>N<sub>4</sub>O<sub>4</sub>. HCl.1.5 H<sub>2</sub>O: C, 53.63; H, 6.30; N, 12.50. Found: C, 53.87; H, 6.13; N, 12.42.

Example 17

Preparation of (S)-8-[3-[(4-amino-2-pyridyl)amino]-1-propyloxy]-3-oxo-2,3,4,5-tetrahydro-1H-2-benzazepine-4-acetic acid a) Methyl (S)-8-[3-[2-(4-nitro-N-oxopyridyl)amino]-1H-propyloxy-3-oxo-2,3,4,5-tetrahydro-1H-2-benzazepine-4-acetate According to the procedure of Example 1(a). except substituting 2-[(3-hydroxy-1propyl)amino]-4-nitropyridine-N-oxide for the 2-[(3-hydroxy-1H-propyl)amino]pyridine-N-oxide, the title compound was prepared as an orange foam: MS (ES) m/e 445.3 (M+H)+.

b) Methyl (S)-8-[3-[(4-amino-2-pyridyl)amino]-1-propyloxy]-3-oxo-2,3,4,5-tetrahydro-1H-2-benzazepine-4-acetate According to the procedure of Example 1(b). except substituting methyl (S)-8-[3-[2-(4-amino-N-oxopyridyl)amino]-1-propyloxy]-3-oxo-2,3,4,5-tetrahydro-1H-2-benzazepine-4-acetate for the methyl (±)-8-[3-[2-(N-oxopyridyl)amino]-1-propyloxy]-3-oxo-2,3,4,5-tetrahydro-1H-2-benzazepine-4-acetate, the title compound was prepared as a white foam: MS (ES) m/e 399.4 (M+H)+.

c) (S)-8-[3-[(4-amino-2-pyridyl)amino]-1-propyloxy]-3-oxo-2,3,4,5-tetrahydro-1H-2-benzazepine-4-acetate acid According to the procedure of Example 1(c), except substituting methyl (S)-8-[3-[(4-amino-2-pyridyl)amino]-1-propyloxy]-3-oxo-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the title compound was prepared as an off-white solid: [α]<sub>D</sub><sup>23</sup> −77.5° (c 1.45, MeOH); MS (ES) m/e 385.4 (M+H)+. Anal. Calcd for C<sub>20</sub>H<sub>24</sub>N<sub>4</sub>O<sub>4</sub>. 1.125 H<sub>2</sub>O: C, 59.36; H, 6.54; N, 13.84. Found: C, 59.31; H, 6.74; N, 13.73.

Example 18

Preparation of Ethyl (±)-8-[3-(2-pyridylamino)-1-propyloxy]-2-methyl-3-oxo-2,3,4,5-tetrahydro-1H-2-benzazepine-4-acetate a) Ethyl (±)-8-[3-(2-pyridylamino)-1-propyloxy]-2-methyl-3-oxo-2,3,4,5-tetrahydro-1H-2-benzazepine-4-acetate A solution of (±)-8-[3-[(4-amino-2-pyridyl)amino]-1-propyloxy]-3-oxo-2,3,4,5-tetrahydro-1H-2-benzazepine-4-acetic acid (0.27 g, 0.7 mmol) and 4 M HCl in dioxane (0.2 mL, 0.8 mmol) in ethanol (10 mL) was heated to reflux. After 72 hr, the reaction was concentrated and the residue was partitioned between EtOAc and aqueous K<sub>2</sub>CO<sub>3</sub>. The organic phase was washed with brine, dried (MgSO<sub>4</sub>), and concentrated. The residue was dissolved in toluene (5 mL) and triethylamine (0.35 mL, 2.5 mmol). and the resulting solution was heated to reflux. After 18 hr, the reaction was concentrated under vacuum to give the title compound (0.20 g, 69%) as a tan foam: MS (ES) m/e 413.4 (M+H)+. Anal. Calcd for C<sub>22</sub>H<sub>28</sub>N<sub>4</sub>O<sub>4</sub>.0.25 H<sub>2</sub>O: C, 63.37; H, 6.89; N,13.44. Found: C, 63.32; H, 7.17; N, 13.05.

Example 19

Preparation of (±)-8-[3-[(2-imidazolin-2-yl)amino]-1-propyloxy]-2-methyl-3-oxo-2,3,4,5-tetrahydro-1H-2-benzazepine-4-acetic acid a) Preparation of methyl(±)-8-[3-(4-nitrobenzyloxycarbonylamino)-1-propyloxy]-2-methyl-3-oxo-2,3,4,5-tetrahydro-1H-2-benzazepine-4-acetate According to the procedure of Example 1(a), except substituting 3-(4-nitrobenzyloxycarbonylamino)-1-propanol for the 2-[(3-hydroxy-1-propyl)amino]pyridine-N-oxide, and substituting methyl (±)-8-hydroxy-2-methyl-3-oxo-2,3,4,5-tetrahydro-1H-2-benzazepine-4-acetate for the methyl (±)-8-hydroxy-3-oxo-2,3,4,5-tetrahydro-1H-2-benzazepine-4-acetate, the title compound was prepared as a colorless oil: MS (ES) m/e 500.3 (M+H)+.

b) Methyl (±)-8-[3-amino-1-propyloxy]-2-methyl-3-oxo-2,3,4,5-tetrahydro-1H-2-benzazepine-4-acetate A mixture of methyl (±)-8-[3-(4-nitrobenzyloxycarbonylamino)-1-propyloxy]-2-methyl-3-oxo-2,3,4,5-tetrahydro-1H-2-benzazepine-4-acetate (1.4 g, 3 mmol), 10% palladium on charcoal (0.55 g, 0.6 mmol), and EtOH (20 mL) was stirred at RT under a balloon of hydrogen. After 18 hr, the mixture was filtered and the filtrate was concentrated to give the title compound (0.89 g, 99%) as a tan solid: MS (ES) m/e 321.4 (M+H)+.

c) Methyl(±)-8-[3-[(2-imidazolin-2-yl)amino]-1-propyloxy]-2-methyl-3-oxo-2,3,4,5-tetrahydro-1H-2-benzazepine-4-acetate A mixture of methyl (±)-8-[3-amino-1-propyloxy]-2-methyl-3-oxo-2,3,4,5-tetrahydro-1H-2-benzazepine-4-acetate (0.3 g, 1 mmol), 2-methylthioimidazoline (0.46 g, 2 mmol), diisopropylethylamine (0.42 mL, 2 mmol) and dimethylacetamide (3 mL) was heated to 100° C. under argon. After 2 hr, the reaction was concentrated under vacuum and the residue was partitioned between CHCl<sub>3</sub> and H<sub>2</sub>O. The organic phase was dried (MgSO<sub>4</sub>) and concentrated, and the residue was purified by preparative HPLC to give the title compound (0.24 g, 51%) as a yellow oil: MS (ES) m/e 389.4 (M+H)+.

d) (±)-8-[3-[(2-Imidazolin-2-yl)amino-1-propyloxy]-2-methyl-3-oxo-2,3,4,5-tetrahydro-1H-2-benzazepine-4-acetic acid Methyl(±)-8-[3-[(2-imidazolin-2-yl)amino]-1-propyloxy]-2-methyl-3-oxo-2,3,4,5-tetrahydro-benzazepine-4-acetate was saponified according to the procedure of Example 1(c). Purification by preparative HPLC gave the title compound as a white solid: MS (ES) m/e 375.4 (M+H)+. Anal. Calcd for C<sub>21</sub>H<sub>26</sub>N<sub>4</sub>O<sub>4</sub>.1.96 CF<sub>3</sub>CO<sub>2</sub>H: C, 46.08; H, 4.73; N, 9.39; Found: C, 46.37; H, 4.53; N, 9.01.

Example 20

Preparation of (±)-8-[3-[(4,5,6,7-tetrahydro-1H-2-diazepin-2-yl)amino]-1-propyloxy]-2-methyl-3-oxo-2,3,4,5-tetrahydro-1H-2-benzazepine-4-acetic acid a) Methyl (±)-8-[3-[(2-diazepin-2-yl)amino]-1-propyloxy]-2-methyl-3-oxo-2,3,4,5-tetrahydro-1H-2-benzazepine-4-acetate According to the procedure of Example 19(c), except substituting 2-methylthio-1,3-diazepine for the 2-methylthioimidazoline, the title compound was prepared: MS (ES) m/e 417.4 (M+H)+.

b) (±)-8-[3-[(2-Diazepin-2-yl)amino]-1-propyloxy]-2-methyl-3-oxo-2,3,4,5-tetrahydro-1H-2-benzazepine-4-acetic acid According to the procedure of Example 19(d), except substituting methyl (±)-8-[3-[(2-diazepin-2-yl)amino)-1-propyloxy]-2-methyl-3-oxo-2,3,4,5-tetrahydro-1H-2-benzazepine-4-acetate for the methyl(±)-8-[3-[(2-imidazolin-2-yl)amino)-1-propyloxy]-2-methyl-3-oxo-2,3,4,5-tetrahydro-1H-2-benzazepine-4-acetate the title compound was prepared: MS (ES) m/e 403.4 (M+H)+.

Example 21

Preparation of (±)-3-oxo-8-[3-(4-methylpyridin-2-ylamino)-1-propyloxy]-2-(2,2,2-trifluoroethyl)-2,3,4,5-tetrahydro-1H-2-benzazepine-4-acetic acid a) Methyl (±)-3-oxo-8-[3-(4-methyl-1-oxopyridin-2-ylamino)-1-propyloxy]-2-(2,2,2-trifluoroethyl)-2,3,4,5-tetrahydro-1H-2-1H-2-benzazepine-4-acetate Following the procedure of Example 1(a), except substituting 2-[(3-hydroxy-1-propyl)amino]-4-methylpyridine-N-oxide for the 2-[(3-hydroxy-1H-propyl)amino]pyridine-N-oxide, and substituting methyl(±)-3-oxo-8-hydroxy-2-(2,2,2-trifluoroethyl)-2,3,4,5-tetrahydro-1H-2-benzazepine-4-acetate for the methyl (±)-8-hydroxy-3-oxo-2,3,4,5-tetrahydro-1H-2-benzazepine-4-acetate the title compound was prepared: MS (ES) m/e 496.3 (M+H)⁺.

b) Methyl(±)-3-oxo-8-[3-(4-methylpyridin-2-ylamino)-1-propyloxy]-2-(2,2,2-trifluoroethyl)-2,3,4,5-tetrahydro-1H-2-benzazepine-4-acetate Following the procedure of Example 1(b), except substituting methyl(±)-3-oxo-8-[3-(4-methyl-1-oxopyridin-2-ylamino)-1-propyloxy]-2-(2,2,2-trifluoroethyl)-2,3,4,5-tetrahydro-1H-2-benzazepine-4-acetate for the methyl (±)-8-[3-[2-(N-oxopyridyl)amino]-1-propyloxy]-3-oxo-2,3,4,5-tetrahydro-1H-2-benzazepine-4-acetate, the title compound was prepared: MS (ES) m/e 480.2 (M+H)⁺.

c) (±)-3-Oxo-8-[3-(4-methylpyridin-2-ylamino)-1-propyloxy]-2-(2,2,2-trifluoroethyl)-2,3,4,5-1H-2-benzazepine-4-acetic acid Following the procedure of Example 1(c), except substituting methyl(±)-3-oxo-8-[3-(4-methylpyridin-2-ylamino)-1-propyloxy]-2-(2,2,2-trifluoroethyl)-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the title compound was prepared: MS (ES) m/e 466.2 (M+H)⁺. Anal. Calcd for $C_{23}H_{26}F_3N_3O_4 \cdot 0.5 H_2O$: C, 58.22; H, 5.74; N, 8.86. Found: C, 58.54; H, 5.58; N, 8.64.

Example 22

Preparation of (±)-3-oxo-8-[3-[N-(pyridin-2-yl)-N-(tert-butoxycarbonyl)amino[-1-1-propyloxy]-2,3,4,5-tetrahydro-1H-2-benzazepine-4-acetic acid (a) Methyl (±)-8-[3-[N-(pyridin-2-yl)-N-(tert-butoxycarbonyl)amino]-1-propyloxy]-3-oxo-2,3,4,5-tetrahydro-1H-2-benzazepine-4-acetic acid According to the procedure of Example 1(b), except substituting methyl (±)-8-[3-[N-(1-oxopyridin-2-yl)-N-(tert-butoxycarbonyl)amino]-1-propyloxy]-3-oxo-2,3,4,5-tetrahydro-1H-2-benzazepine-4-acetic acid for the methyl (±)-8-[3-[2-(N-oxopyridyl)amino]-1-propyloxy]-3-oxo-2,3,4,5-tetrahydro-2-benzazepine-4-acetate, the title compound was prepared as a white foam: MS (ES) m/e 484.4 (M+H)⁺.

(b) (±)-3-oxo-8-[3-[N-pyridin-2-yl)-N-(tert-butoxycarbonyl)amino-1-propyloxy]-2,3,4,5-tetrahydro-1H-2-benzazepine-4-acetic acid According to the procedure of Example 1(c), except substituting methyl (±)-8-[3-[N-(pyridin-2-yl)-N-(tert-butoxycarbonyl)amino]-1-propyloxy]-3-oxo-2,3,4,5-tetrahydro-1H-2-benzazepine-4-acetic acid for the ethyl (±)-8-[3-(2-pyridylamino)-1H-propyloxy)-3-oxo-2,3,4,5-tetrahydro-1H-2-benzazepine-4-acetate, the title compound was prepared as a white powder: MS (ES) m/e 470.4 (M+H)⁺. Anal. Calcd for $C_{25}H_{30}NaN_3O_6 \cdot 3.25 H_2O$: C, 54.59; H, 6.69: N, 7.64. Found: C, 54.47; H, 6.32; N, 7.95.

Example 23

Preparation of (±)-8-[3-[N-(1-oxopyridin-2-yl)-N-(tert-butoxycarbonyl)amino]-1-propyloxy]-3-oxo-2,3,4,5-tetrahydro-1H-2-benzazepine-4-acetic acid (a) (±)-8-[3-[N-(1-oxopyridin-2-yl)-N-(tert-butoxycarbonyl)amino]-1-propyloxy]-3-oxo-2,3,4,5-tetrahydro-1H-2-benzazepine-4-acetic acid According to the procedure of Example 1(c), except substituting methyl(±)-8-[3-[N-(1-oxopyridin-2-yl)-N-(tert-butoxycarbonyl)amino]-1-propyloxy]-3-oxo-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the title compound was prepared as a white powder: ¹H NMR (400 MHz, DMSO-d₆) δ 6.6–8.3 (m, 8 H), 3.7–4.6 (m, 3 H), 3.3–3.6 (m, 5 H), 1.8–3.0 (m, 5 H), 1.6 (s, 6 H), 1.3 (s, 3 H); MS (ES) m/e 486.4 (M+H)⁺.

Example 24

Preparation of (±)-3-oxo-8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetic acid (a) Methyl(±)-3-oxo-8-[3-[N-(1-oxopyridin-2-yl)-N-(tert-butoxycarbonyl)amino]-1-propyloxy]-2-(4-trifluoromethylbenzyl)-2,3,4,5-tetrahydro-1H-2-benzazepine-4-acetate A solution of methyl (±)-8-[3-[N-(1-oxopyridin-2-yl)-N-(tert-butoxycarbonyl)amino]-1-propyloxy]-3-oxo-2,3,4,5-tetrahydro-1H-2-benzazepine-4-acetic acid (0.4 g, 0.8 mmol) in DMF (5 mL) was cooled to −20° C. (CCl₄/dry ice bath), and (TMS)₂NLi (1.0 M solution in THF, 0.9 mL, 0.9 mmol) was added dropwise. After 10 min a solution of 4-trifluoromethylbenzyl bromide (0.211 g, 0.88 mmol) in DMF (0.5 mL) was added. The solution was stirred under an argon atmosphere at −20° C. for 10 min then at RT for 18 h. The solution was concentrated, and the residue was taken up in EtOAc and washed successively with 5% NaHCO₃ (2×), H₂O (1×), 5% citric acid (2×), H₂O (1×), and brine (1×). The EtOAc layer was dried (MgSO₄) and concentrated to give the title compound (0.42 g, 80%): MS (ES) m/e 658.3 (M+H)+.

(b) Methyl (±)-3-oxo-8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetate According to the procedure of Example 1(b), except substituting methyl (±)-3-oxo-8-[3-[N-(1-oxopyridin-2-yl)-N-(tert-butoxycarbonyl)amino]-1-propyloxy]-2-(4-trifluoromethylbenzyl)-2,3,4,5-tetrahydro-1H-2-benzazepine-4-acetate for the ethyl (±)-8-[3-[2-(N-oxopyridyl)amino]-1-propyloxy]-3-oxo-2,3,4,5-tetrahydro-2-benzazepine-4-acetate, the title compound (0.321 g, 78%) was prepared as a clear oil: MS (ES) m/e 642.3 (M+H)⁺.

(c) (±)-3-Oxo-8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetic acid According to the procedure of Example 1(c), except substituting methyl (±)-3-oxo8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the title compound was prepared as an off-white solid: MS (ES) m/e 628.4 (M+H)⁺. Anal. Calcd for $C_{33}H_{36}F_3N_3O_6 \cdot 0.5 H_2O$: C, 62.25; H, 5.86; N, 6.60. Found C, 62.01; H, 5.92; N, 6.81.

Example 25

Preparation of (±)-3-oxo-8-[3-(pyridin-2-ylamino)-1-propyloxy]-2-(4-trifluoromethylbenzyl)-2,3,4,5-tetrahydro-1H-2-benzazepine-4-acetic acid (a) (±)-3-Oxo-8-[3-(pyridin-2-ylamino)-1-propyloxy]-2-(4-trifluoromethylbenzyl)-2,3,4,5-tetrahydro-1H-2-benzazepine-4-acetic acid (±)-3-Oxo-8-[3-[N-(pyridin-2-yl)-N-(tert-butoxycarbonyl)amino]-1-propyloxy]-2-(4- trifluoromethylbenzyl)-2,3,4,5-tetrahydro-1H-2-benzazepine-4-acetic acid (0.158 g, 0.25 mmol) was treated with 4 M HCl in dioxane (3 mL) at RT for 1 h, then the solution was concentrated. ODS chromatography (gradient 5–60% $CH_3CN/H_2O$ containing 0.1% TFA over 1 h), concentration and lyophilization gave the title compound (0.117 g, 82%): MS (ES) m/e 528.4 $(M+H)^+$. Anal. Calcd for $C_{28}H_{28}N_3O_4 \cdot 1\ CF_3CO_2H \cdot 1.5\ H_2O$: C, 53.89; H, 4.82; N. 6.28. Found: C, 53.55; H, 4.55; N, 6.04.

Example 26

Preparation of (±)-2-methyl-3-oxo-8-[3-[N-(pyridin-2-yl)-N-(methyl)amino)]-1-propyloxy]-2,3,4,5-tetrahydro-1H-2-benzazepine-4-acetic acid (a) Methyl (±)-8-[3-[2-(N-oxopyridyl)-N-(methyl)amino]-1-propyloxy]-3-oxo-2,3,4,5-tetrahydro-1H-2-methyl-benzazepine-4-acetate A solution of methyl (±)-8-[3-[2-(N-oxopyridyl)amino]-1-propyloxy]-3-oxo-2,3,4,5-tetrahydro-1H-2-benzazepine-4-acetate (1.5 g, 3.8 mmol) in DMF (10 mL) was cooled to –20° C. under an argon atmosphere, and $(TMS)_2NLi$ (1.0 M solution in THF, 8 mL, 8 mmol) was added dropwise. The reaction was stirred at –20° C. for 30 minutes. then $CH_3I$ (0.5 mL, 7.6 mmol) was added. The solution was stirred at RT for 18 h, then was concentrated. Silica gel chromatography (10% $MeOH/CH_2Cl_2$) gave the title compound (1 g, 62%): MS (ES) m/e 428.4 $(M+H)^+$.

(b) Methyl (±)-2-methyl-3-oxo-8-[3-[N-(pyridin-2-yl)-N-(methyl)amino)]-1-propyloxy]-2,3,4,5-tetrahydro-1H-2-benzazepine-4-acetate According to the procedure of Example 1(b), except substituting methyl (±)-8-[3-[2-(N-oxopyridyl)-N-(methyl)amino]-1-propyloxy]-3-oxo-2,3,4,5-tetrahydro-1H-2-methyl-benzazepine-4-acetate for the ethyl (±)-8-[3-(2-pyridylamino)-1-propyloxy]-3-oxo-2,3,4,5-tetrahydro-1H-2-benzazepine-4-acetate, the title compound (0.7 g, 73%) was prepared: MS (ES) m/e 412.4 $(M+H)^+$.

(c) (±)-2-Methyl-3-oxo-8-[3-[N-(pyridin-2-yl)-N-(methyl)amino)]-1-propyloxy]-2,3,4,5-tetrahydro-1H-2-benzazepine-4-acetic acid According to the procedure of Example 1(c), except substituting methyl (±)-2-methyl-3-oxo-8-[3-[N-(pyridin-2-yl)-N-(methyl)amino)]-1-propyloxy]-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the crude title compound was prepared. Purification by ODS chromatography (5–60% $CH_3CN/H_2O$ containing 0.1% TFA over 1 h). concentration and lyophilization gave the title compound: MS (ES) m/e 398.4 $(M+H)^+$. Anal. Calcd for $C_{22}H_{27}N_3O_4 \cdot 1.5\ CF_3CO_2H \cdot 0.25\ H_2O$: C, 52.40; H, 5.10; N, 7.33. Found: C, 52.09; H, 5.26; N, 7.20.

Example 27

Preparation of (±)-2-benzyl-3-oxo-8-[3-(pyridin-2-ylamino)-1-propyloxy]-2,3,4,5-tetrahydro-1H-2-benzazepine-4-acetic acid (a) Methyl (±)-2-benzyl-3-oxo-8-[3-[N-(1-oxopyridin-2-yl)-N-(tert-butoxycarbonyl)amino]-1-propyloxy]-2,3,4,5-tetrahydro-1H-2-benzazepine-4-acetate According to the procedure of Example 24(a), except substituting benzyl bromide for the 4-trifluoromethylbenzyl bromide, the title compound (0.1 05 g, 20%) was prepared: MS (ES) m/e 590.4 $(M+H)^+$.

(b) Methyl (±)-2-benzyl-3-oxo-8-[3-[N-(pyridin-2-yl)-N-(tert-butoxycarbonyl)amino]-1-propyloxy]-2,3,4,5-tetrahydro-1H-2-benzazepine-4-acetate According to the procedure of Example 24(b), except substituting methyl (±)-2-benzyl-3-oxo-8-[3-[N-(1-oxopyridin-2-yl)-N-(tert-butoxycarbonyl)amino]-1-propyloxy]-2,3,4,5-tetrahydro-1H-2-benzazepine-4-acetate for the methyl (±)-3-oxo-8-[3-[N-(1-oxopyridin-2-yl)-N-(tert-butoxycarbonyl)amino]-1-propyloxy]-2-(4trifluoromethylbenzyl)-2,3,4,5-tetrahydro-1H-2-benzazepine-4-acetate, the title compound (0.045 g, 44%) was prepared: MS (ES) m/e 574.4 $(M+H)^+$.

(c) (±)-2-Benzyl-3-oxo-8-[3-[N-(pyridin-2-yl)-N-(tert-butoxycarbonyl)amino)-1-propyloxy]-2,3,4,5-tetrahydro-1H-2-benzazepine-4-acetic acid According to the procedure of Example 1(c), except substituting methyl (±)-2-benzyl-3-oxo-8-[3-[N-(pyridin-2-yl)-N-(tert-butoxycarbonyl)amino]-1-propyloxy]-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the title compound (0.044 g, quantitative) was prepared: MS (ES) m/e 560.3 $(M+H)^+$.

(d) (±)-2-Benzyl-3-oxo-8-[3-(pyridin-2-ylamino)-1-propyloxy]-2,3,4,5-tetrahydro-1H-2-benzazepine-4-acetic acid According to the procedure of Example 25(a) except substituting (±)-2-benzyl-3-oxo-8-[3-[N-(pyridin-2-yl)-N-(tert-butoxycarbonyl)amino]-1-propyloxy]-2,3,4,5-tetrahydro-1H-2-benzazepine-4-acetic acid for the (±)-3-oxo-8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetic acid, the title compound (0.014 g, 40%) was prepared: MS (ES) m/e 460.4 $(M+H)^+$. Anal. Calcd for $C_{27}H_{29}N_3O_4 \cdot CF_3CO_2H \cdot 2\ H_2O$: C, 57.14; H, 5.62; N, 6.89. Found: C, 57.44; H, 5.32; N, 6.87.

Example 28

Preparation of (±)-2-(carboxymethyl)-3-oxo-8-[3-(pyridin-2-ylamino)-1-propyloxy]-2,3,4,5-tetrahydro-1H-2-benzazepine-4-acetic acid (a) Methyl (±)-2-(tert-butoxycarbonylmethyl)-3-oxo-8-[3-[N-(1-oxo-pyridin-2-yl)-N-(tert-butoxycarbonyl)amino]-1-propyloxy]-2,3,4,5-tetrahydro-1H-2-benzazepine-4-acetate According to the procedure of Example 24(a) except substituting tert-butyl bromoacetate for the 4-trifluoromethylbenzyl bromide, the title compound (1.0 g, 80%) was prepared: MS (ES) m/e 614.4 $(M+H)^+$.

(b) Methyl (±)-2-(tert-butoxycarbonylmethyl)-3-oxo-8-[3-[N-(pyridin-2-yl)-N-(tert-butoxycarbonyl)amino]-1-propyloxy]-2,3,4,5-tetrahydro-1H-2-benzazepine-4-acetate According to the procedure of Example 24(b) except substituting methyl (±)-2-(tert-butoxycarbonylmethyl)-3-oxo-8-[3-[N-(1-oxo-pyridin-2-yl)-N-(tert-butoxycarbonyl)amino]-1-propyloxy]-2,3,4,5-tetrahydro-1H-2-benzazepine-4-acetate for the methyl (±)-3-oxo-8-[3-[N-(1-oxopyridin-2-yl)-N-(tert-butoxycarbonyl)amino]-1-propyloxy]-2-(4-trifluoromethylbenzyl)-2,3,4,5-tetrahydro-1H-2-benzazepine-4-acetate, the title compound (0.72 g, 77%) was prepared: MS (ES) m/e 598.4 $(M+H)^+$.

(c) Methyl (±)-2-(carboxymethyl)-3-oxo-8-[3-(pyridin-2-ylamino)-1-propyloxy]-2,3,4,5-tetrahydro-1H-2-benzazepine-4-acetate According to the procedure of Example 25(a) except substituting methyl (±)-2-(tert-butoxycarbonylmethyl)-3-oxo-8-[3-N-(pyridin-2-yl)-N-(tert-butoxycarbonyl)amino]-1-propyloxy]-2,3,4,5-tetrahydro-1H-2-benzazepine-4-acetate for the (±)-3-oxo-8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetic acid, the title compound (0.57 g. quantitative) was prepared: MS (ES) m/e 442.3 $(M+H)^+$.

(d) (±)-2-(Carboxymethyl)-3-oxo-8-[3-(pyridin-2-ylamino)-1-propyloxy]-2,3,4,5-tetrahydro-1H-2-benzazepine-4-acetic acid According to the procedure of Example 1(c) except substituting methyl (±)-2-(carboxymethyl)-3-oxo-8-[3-(pyridin-2-ylamino)-1-propyloxy]-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the title compound (0.30 g, 56%) was prepared: MS (ES) m/e 428.4 (M+H)$^+$. Anal. Calcd for $C_{22}H_{25}N_3O_6 \cdot 2 H_2O$: C, 57.01; H, 6.31; N, 9.07; Found: C, 57.27; H, 6.24; N, 8.86.

Example 29

Preparation of (±)-2-(4-aminobenzyl)-3-oxo-8-[3-(pyridin-2-ylamino)-1-propyloxy]-2,3,4,5-tetrahydro-1H-2-benzazepine-4-acetic acid (a) Methyl(±)-2-(4-nitrobenzyl)-3-oxo-8-[3-[N-(1-oxo-pyridin-2-yl)-N-(tert-butoxycarbonyl)amino]-1-propyloxy]-2,3,4,5-tetrahydro-1H-2-benzazepine-4-acetate According to the procedure of Example 24(a), except substituting 4-nitrobenzylbromide for the 4-trifluoromethylbenzyl bromide, the title compound (0.284 g, 69%) was prepared: MS (ES) m/e 635.3 (M+H)$^+$.

(b) Methyl(±)-2-(4-aminobenzyl)-3-oxo-8-[3-[N-(1-oxo-pyridin-2-yl)-N-(tert-butoxycarbonyl)amino]-1-propyloxy]-2,3,4,5-tetrahydro-1H-2-benzazepine-4-acetate According to the procedure of Example 24(b) except substituting methyl(±)-2-(4-nitrobenzyl)-3-oxo-8-[3-[N-(1-oxo-pyridin-2-yl)-N-(tert-butoxycarbonyl)amino]-1-propyloxy]-2,3,4,5-tetrahydro-1H-2-benzazepine-4-acetate for the methyl (±)-3-oxo-8-[3-[N-(1-oxopyridin-2-yl)-N-(tert-butoxycarbonyl)amino]-1-propyloxy]-2-(4-trifluoromethylbenzyl)-2,3,4,5-tetrahydro-1H-2-benzazepine-4-acetate, the title compound (0.104 g, 40%) was prepared: MS (ES) m/e 589.3 (M+H)$^+$.

(c) (±)-2-(4-Aminobenzyl)-3-oxo-8-[3-[N-(pyridin-2-yl)-N-(tert-butoxycarbonyl)amino]-1-propyloxy]-2,3,4,5-tetrahydro-1H-2-benzazepine-4-acetic acid According to the procedure of Example 1(c), except substituting methyl(±)-2-(4-aminobenzyl)-3-oxo-8-[3-[N-(1-oxo-pyridin-2-yl)-N-(tert-butoxycarbonyl)amino]-1-propyloxy]-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the title compound (0.08 g, 79%) was prepared: MS (ES) m/e 575.4 (M+H)$^+$.

(d) (±)-2-(4-Aminobenzyl)-3-oxo-8-[3-(pyridin-2-yl-amino)-1-propyloxy]-2,3,4,5-tetrahydro-1H-2-benzazepine-4-acetic acid According to the procedure of Example 25(a) except substituting (±)-2-(4-aminobenzyl)-3-oxo-8-[3-[N-(pyridin-2-yl)-N-(tert-butoxycarbonyl)amino]-1-propyloxy]-2,3,4,5-tetrahydro-1H-2-benzazepine-4-acetic acid for the (±)-3-oxo-8-[3-[N-(pyridin-2-yl)-N-(tert-butoxycarbonyl)amino]-1-propyloxy]-2-(4-triflouromethylbenzyl)-2,3,4,5-tetrahydro-1H-2-benzazepine-4-acetic acid, the title compound (0.029 g, 44%) was prepared: MS (ES) m/e 475.4 (M+H)$^+$. Anal. Calcd for $C_{27}H_{30}N_4O_4 \cdot 2 CF_3CO_2H \cdot 1.5 H_2O$: C, 51.03; H, 4.83; N, 7.68. Found: C, 50.92; H, 4.78; N, 7.64.

Example 30

Preparation of (±)-3-oxo-8-[3-[N-(pyridin-2-yl)-N-(benzoyl)amino]-1-propyloxy]-2-(4-trifluoromethylbenzyl)-2,3,4,5-tetrahydro-1H-2-benzazepine-4-acetic acid (a) Methyl (±)-3-oxo-8-[3-(1-oxo-pyridin-2-yl)amino-1-propyloxy]-2-(4-trifluoromethylbenzyl)-2,3,4,5-tetrahydro-1H-2-benzazepine-4-acetate According to the procedure of Example 25(a), except substituting methyl (±)-3-oxo-8-[3-[N-(1-oxopyridin-2-yl)-N-(tert-butoxycarbonyl)amino]-1-propyloxy]-2-(4-trifluoromethylbenzyl)-2,3,4,5-tetrahydro-1H-2-benzazepine-4-acetate for the (±)-3-oxo-8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetic acid, the title compound (1.9 g, 90%) was prepared: MS (ES) m/e 558.3 (M+H)$^+$.

(b) Methyl (±)-3-oxo-8-[3-(pyridin-2-yl)amino]-1-propyloxy]-2-(4-trifluoromethylbenzyl)-2,3,4,5-tetrahydro-1H-2-benzazepine-4-acetate According to the procedure of Example 24(b), except substituting methyl (±)-3-oxo-8-[3-(1-oxo-pyridin-2-yl)amino-1-propyloxy]-2-(4-trifluoromethylbenzyl)-2,3,4,5-tetrahydro-1H-2-benzazepine-4-acetate for the methyl (±)-3-oxo-8-[3-[N-(1-oxopyridin-2-yl)-N-(tert-butoxycarbonyl)amino]-1-propyloxy]-2-(4-trifluoromethylbenzyl)-2,3,4,5-tetrahydro-1H-2-benzazepine-4-acetate, the title compound (0.40 g, 88%) was prepared: MS (ES) m/e 542.3 (M+H)$^+$.

(c) Methyl(±)-3-oxo-8-[3-[N-(pyridin-2-yl)-N-(benzoyl)amino]-1-propyloxy]-2-(4-trifluoromethylbenzyl)-2,3,4,5-tetrahydro-1H-2-benzazepine-4-acetate Benzoyl chloride (0.094 mL, 0.8 mmol) was added dropwise to a solution of methyl (±)-3-oxo-8-[3-(pyridin-2-yl)amino]-1-propyloxy]-2-(4-trifluoromethylbenzyl)-2,3,4,5-tetrahydro-1H-2-benzazepine-4-acetate (0.4 g, 0.74 mmol) and diisopropylethylamine (0.5 mL, 2.9 mmol) in $CH_2Cl_2$ (10 mL). After 18 h, the solution was concentrated, and the residue was purified by silica gel chromatography (1:1 EtOAc/Hexane) to give the title compound (0.293 g, 61%): MS (ES) m/e 646.2 (M+H)$^+$.

(d) (±)-3-Oxo-8-[3-[N-(pyridin-2-yl)-N-(benzoyl)amino]-1-propyloxy]-2-(4-trifluoromethylbenzyl)-2,3,4,5-tetrahydro-1H-2-benzazepine-4-acetic acid According to the procedure of Example 1(c) except substituting methyl(±)-3-oxo-8-[3-[N-(pyridin-2-yl)-N-(benzoyl)amino]-1-propyloxy]-2-(4-trifluoromethylbenzyl)-2,3,4,5-tetrahydro-1H-2-benzazepine-4-acetate, for the ethyl (±)-8-[3-(2-pyridylamino)-1-propyloxy]-3-oxo-2,3,4,5-tetrahydro-1H-2-benzazepine-4-acetate, the crude title compound was prepared. Purification by ODS chromatography (10–80% $CH_3CN/H_2O$ containing 0.1% TFA over 1 h), concentration and lyophilization gave the title compound (0.025 g, 10%): MS (ES) m/e 632.4 (M+H)$^+$. Anal. Calcd for $C_{35}H_{32}F_3N_3O_5 \cdot 0.85 CF_3CO_2H$: C, 60.50; H, 4.54; N, 5.74. Found: C, 60.22; H, 4.35; N, 5.77.

Example 31

Preparation of (±)-3-oxo-8-[3-[N-(pyridin-2-yl)-N-(tert-butylacetyl)amino]-1-propyloxy]-2-(4-trifluoromethylbenzyl)-2,3,4,5-tetrahydro-1H-2-benzazepine-4-acetic acid (a) Methyl (±)-3-oxo-8-[3-[N-(1-oxo-pyridin-2-yl)-N-(tert-butylacetyl)amino]-1-propyloxy]-2-(4-trifluoromethylbenzyl)-2,3,4,5-tetrahydro-1H-2-benzazepine-4-acetate A solution of tert-butyl acetic acid (0.228 mL, 1.2 mmol) in $CH_2Cl_2$ (10 mL) was treated with oxalyl chloride (1 mL, 11.4 mmol), followed by DMF (0.0005 mL, 0.06 mmol). The reaction was stirred at RT for 1.5 h, then was concentrated. The residue was taken up in $CH_2Cl_2$ (5 mL) and was added dropwise to a solution of methyl (±)-3-oxo-8-[3-(1-oxo-pyridin-2-yl)amino-1-propyloxy]-2-(4-trifluoromethylbenzyl)-2,3,4,5-tetrahydro-1H-2-benzazepine-4-acetate (0.35 g, 0.6 mmol) and $Et_3N$ (0.5 mL, 2.4 mmol) in $CH_2Cl_2$ (10 mL). After 18 h the solution was washed sequentially with $H_2O$ (1×), 5% $NaHCO_3$ (2×), $H_2O$ (1×), 5% citric acid (2×), $H_2O$ (1×) and satd NaCl (1×). The organic layer was concentrated to give the title compound (0.4 g, 97%): MS (ES) m/e 656.4 (M+H)⁺.

(b) Methyl (±)-3-oxo-8-[3-[N-(pyridin-2-yl)-N-(tert-butylacetyl)amino]-1H-propyloxy]-2-(4-trifluoromethylbenzyl)-2,3,4,5-tetrahydro-1H-2-benzazepine-4-acetate According to the procedure of Example 24(b), except substituting methyl (±)-3-oxo-8-[3-[N-(1-oxo-pyridin-2-yl)-N-(tert-butylacetyl)amino]-1-propyloxy]-2-(4-trifluoromethylbenzyl)-2,3,4,5-tetrahydro-1 H-2-benzazepine-4-acetate for the methyl (±)-3-oxo-8-[3-[N-(1-oxopyridin-2-yl)-N-(tert-butoxycarbonyl)amino]-1-propyloxy]-2-(4-trifluoromethylbenzyl)-2,3,4,5-tetrahydro-1H-2-benzazepine-4-acetate, the title compound (0.22 g, 56%) was prepared: MS (ES) m/e 642.3 (M+H)⁺.

(c) (±)-3-Oxo-8-[3-[N-(pyridin-2-yl)-N-(tert-butylacetyl)amino]-1-propyloxy]-2-(4-trifluoromethylbenzyl)-2,3,4,5-tetrahydro-1H-2-benzazepine-4-acetic acid According to the procedure of Example 1(c), except substituting methyl (±)-3-oxo-8-[3-[N-(pyridin-2-yl)-N-(tert-butylacetyl)amino]-1-propyloxy]-2-(4-trifluoromethylbenzyl)-2,3,4,5-tetrahydro-1H-2-benzazepine-4-acetate for the ethyl (±)-8-[3-(2-pyridylamino)-1H-propyloxy]-3-oxo-2,3,4,5-tetrahydro-1H-2-benzazepine-4-acetate, the crude title compound was prepared. Purification by ODS chromatography (10–80% $CH_3CN/H_2O$ containing 0.1% TFA over 1 h), concentration and lyophilization gave the title compound (0.022 g, 10%): MS (ES) m/e 626.4 (M+H)⁺. Anal. Calcd for $C_{34}H_{38}F_3N_3O_5$.1 $H_2O$: C, 63.44; H, 6.26; N, 6.53. Found: C, 63.24; H, 5.96; N, 6.39.

Example 32
Preparation of (±)-3-Oxo-8-[3-[N-(pyridin-2-yl)-N-(isobutoxycarbonyl)amino]-1-propyloxy]-2-(4-trifluoromethylbenzyl)-2,3,4,5-tetrahydro-1H-2-benzazepine-4-acetic acid (a) Methyl (±)-3-oxo-8-[3-[N-(1-oxo-pyridin-2-yl)-N-(isobutoxycarbonyl)amino]-1-propyloxy]-2-(4-trifluoromethylbenzyl)-2,3,4,5-tetrahydro-1H-2-benzazepine-4-acetate According to the procedure of Example 30(c), except substituting isobutyl chloroformate for the benzoyl chloride, the title compound (0.47 g, 80%) was prepared: MS (ES) m/e 658.3 (M+H)⁺.

(b) Methyl (±)-3-oxo-8-[3-[N-(pyridin-2-yl)-N-(isobutoxycarbonyl)amino]-1-propyloxy]-2-(4-trifluoromethylbenzyl)-2,3,4,5-tetrahydro-1H-2-benzazepine-4-acetate According to the procedure of Example 24(b), except substituting methyl(±)-3-oxo-8-[3-[N-(1-oxo-pyridin-2-yl)-N-(isobutoxycarbonyl)amino]-1-propyloxy]-2-(4-trifluoromethylbenzyl)-2,3,4,5-tetrahydro-1H-2-benzazepine-4-acetate for the methyl (±)-3-oxo-8-[3-[N-(1-oxopyridin-2-yl)-N-(tert-butoxycarbonyl)amino]-1-propyloxy]-2-(4-trifluoromethylbenzyl)-2,3,4,5-tetrahydro-1H-2-benzazepine-4-acetate, the title compound (0.4 g, 63%) was prepared: MS (ES) n/e 642.3 (M+H)⁺.

(c) (±)-3-Oxo-8-[3-[N-(pyridin-2-yl)-N-(isobutoxycarbonyl)amino]-1-propyloxy]-2-(4-trifluoromethylbenzyl)-2,3,4,5-tetrahydro-1H-2-benzazepine-4-acetic acid According to the procedure of Example 1(c), except substituting methyl(S)-3-oxo-8-[3-[N-(pyridin-2-yl)-N-(isobutoxycarbonyl)amino]-1-propyloxy]-2-(4-trifluorobenzyl)-2,3,4,5-tetrahydro-1H-2-benzazepine-4-acetate for the ethyl (±)-8-[3-(2-pyridylamino)-1-propyloxy]-3-oxo-2,3,4,5-tetrahydro-1H-2-benzazepine-4-acetate, the crude title compound was prepared. Purification by ODS chromatography (10–80% $CH_3CN/H_2O$ containing 0.1% TFA over 1 h), concentration and lyophilization gave the title compound (0.008 g, 20%): MS (ES) m/e 628.3 (M+H)⁺. Anal Calcd. for $C_{33}H_{36}F_3N_3O_6$.0.25 $CF_3CO_2H$.0.5 $H_2O$: C, 60.49; H, 5.64; N, 6.32. Found: C, 60.78; H, 5.50; N, 6.28.

Example 33
Preparation of (S)-3-oxo-8-[3-(pyridin-2-ylamino)-1-propyloxy]-2-(4-trifluoromethylbenzyl)-2,3,4,5-tetrahydro-1H-2-benzazepine-4-acetic acid (a) Methyl (S)-3-oxo-8-[3-[N-(1-oxo-pyridin-2-yl)-N-(tert-butoxycarbonyl)amino]-1-propyloxy]-2-(4-trifluoromethylbenzyl)-2,3,4,5-tetrahydro-1H-2-benzazepine-4-acetate According to the procedure of Example 1(a), except substituting methyl (S)-8-hydroxy-3-oxo-2,3,4,5-tetrahydro-1H-2-benzazepine-4-acetate for the methyl (±)-8-hydroxy-3-oxo-2,3,4,5-tetrahydro-1H-2-benzazepine-4-acetate, the title compound (3.0 g, 83%) was prepared: MS (ES) m/e 500.3 (M+H)⁺.

(b) Methyl (S)-3-oxo-8-[3-[N-(1-oxo-pyridin-2-yl)-N-(tert-butoxycarbonyl)amino]-1-propyloxy]-2-(4-trifluoromethylbenzyl)-2,3,4,5-tetrahydro-1H-2-benzazepine-4-acetate According to the procedure of Example 24(a), except substituting methyl (S)-3-oxo-8-[3-[N-(1-oxo-pyridin-2-yl)-N-(tert-butoxycarbonyl)amino]-1-propyloxy]-2,3,4,5-tetrahydro-1H-2-benzazepine-4-acetate for the methyl-(±)-3-oxo-8-[3-[N-(1-oxo-pyridin-2-yl)-N-(tert-butoxycarbonyl)amino]-1-propyloxy]-2,3,4,5-tetrahydro-1H-2-benzazepine-4-acetate, the title compound (2.3 g, 72%) was prepared: MS (ES) m/e 658.2 (M+H)⁺.

(c) Methyl (S)-3-oxo-8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetate According to the procedure of Example 24(b), except substituting methyl (S)-3-oxo-8-[3-[N-(1-oxo-pyridin-2-yl)-N-(tert-butoxycarbonyl)amino]-1-propyloxy]-2-(4-trifluoromethylbenzyl)-2,3,4,5-tetrahydro-1H-2-benzazepine-4-acetate for the methyl (±)-3-oxo-8-[3-[N-(1-oxopyridin-2-yl)-N-(tert-butoxycarbonyl)amino]-1-propyloxy]-2-(4-trifluoromethylbenzyl)-2,3,4,5-tetrahydro-1H-2-benzazepine-4-acetate, the title compound (1.1 g, 50%) was prepared: MS (ES) m/e 642.1 (M+H)⁺.

(d) (S)-3-oxo-8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetic acid According to the procedure of Example 24(c) except substituting methyl (S)-3-oxo-8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetate for the methyl (±)-3-oxo-8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetate, the title compound (0.8 g, 60%) was prepared: MS (ES) m/e 628.1 (M+H)⁺.

(e) (S)-3-Oxo-8-[3-(pyridin-2-yl-amino)-1-propyloxy]-2-(4-trifluoromethylbenzyl)-2,3,4,5-tetrahydro-1H-2-benzazepine-4-acetic acid According to the procedure of Example 25(a) except substituting (S)-3-oxo-8-[3-[N-(pyridin-2-yl)-N-(tert-butoxycarbonyl)amino]-1-propyloxy]-2-(4trifluoromethylbenzyl)-2,3,4,5-tetrahydro-1H-2-benzazepine-4-acetic acid for the (±)-3-oxo-8-[3-[N-(pyridin-2-yl)-N-(tert-butoxycarbonyl)amino]-1- propyloxy]-2-(4-trifluoromethylbenzyl)-2,3,4,5-tetrahydro-1H-2-benzazepine-4-acetic acid, the crude title compound was prepared. Purification by ODS chromatography (30% CH$_3$CN/H$_2$O containing 0.1% TFA over 1 h), concentration and lyophilization gave the title (0.657 g, 72%) compound: [α]$_D$ –42° (c 1.0, MeOH); MS (ES) m/e 528.1 (M+H)$^+$. Anal. Calcd for C$_{28}$H$_{28}$F$_3$N$_3$O$_4$.2 CF$_3$CO$_2$H.3.75 H$_2$O: C, 46.69; H, 4.59; N, 5.10. Found: C, 46.47; H, 4.58; N, 5.48.

Example 34

Preparation of Methyl (±)-3-oxo-8-[3-(pyridin-2-ylamino)-1-propyloxy]-2,3,4,5-tetrahydro-1H-2-benzazepine-4-acetate (a) Methyl (±)-3-oxo-8-[3-(pyridin-2-ylamino)-1-propyloxy]-2,3,4,5-tetrahydro-1H-2-benzazepine-4-acetate According to the procedure of Example 1(b), except substituting isopropanol for the ethanol, the title compound (0.35 g, 76%) was prepared: MS (ES) m/e 384.4 (M+H)$^+$.

Example 35

Preparation of (S)-3-oxo-8-[3-(1,4,5,6-tetrahydropyrimid-2-ylamino)-1-propyloxy]-2-[4-(trifluoromethyl)benzyl]-2,3,4,5-tetrahydro-1H-2-benzazepine-4-acetic acid a) Methyl (S)-8-[3-(4-nitrobenzyloxycarbonylamino)-1-propyloxy]-3-oxo-2-4-(trifluoromethyl)benzyl]-2,3,4,5-tetrahydro-1H-2-benzazepine-4-acetate To methyl (S)-8-hydroxy-3-oxo-2-[4-(trifluoromethyl)benzyl]-2,3,4,5-tetrahydro-1H-2-benzazepine-4-acetate (0.14 g, 0.34 mmol) and Ph$_3$P (0.13 g, 0.50 mmol) in CH$_2$Cl$_2$ (2 mL) at 0° C. was added dropwise a solution of 3-(4-nitrobenzyloxycarbonylamino)-1-propanol (0.13 g, 0.51 mmol) and diethylazodicarboxylate (0.08 mL, 0.50 mL). When the addition was complete, the ice bath was removed and the reaction was stirred at RT. After 18 h, the solvent was removed and the product was isolated by flash chromatography on silica gel (100% CHCl$_3$ to 5% MeOH/CHCl$_3$) to give the title compound (0.12 g) as a clear oil. $^1$H NMR (400 MHz, CDCl$_3$) δ 8.18 (d, J=8.2 Hz, 2H), 7.65 (m, 1H), 7.50 (m, 5H), 7.40 (d, J=8.2 Hz, 1H), 7.03 (d, J=9.8 Hz, 1H), 6.70 (m, 1H), 6.30 (s, 1H), 5.23 (m, 3H), 4.95 (d, J=16.4 Hz, 1H), 4.50 (d, J=16.4 Hz, 1H), 3.95 (m, 3H), 3.78 (s, 3H), 3.70 (m, 1H), 3.45 (m, 2H), 3.15–2.90 (m, 3H), 2.50 (dd, J=19.2, 5.5 Hz, 1H), 1.95 (m, 2H).

b) Methyl (S)-8-(3-amino-1-propyloxy)-3-oxo-2-[4-(trifluoromethyl)benzyl]-2,3,4,5-tetrahydro-1H-2-benzazepine-4-acetate To methyl (S)-8-[3-(4-nitrobenzyloxycarbonylamino)-1-propyloxy]-3-oxo-2-[4-(trifluoromethyl)benzyl]-2,3,4,5-tetrahydro-1H-2-benzazepine-4-acetate (0.12 g, 0.19 mmol) in MeOH (2 mL) was added 10% Pd/C (20 mg). The reaction vessel was flushed with hydrogen and then fitted with a hydrogen-filled balloon. After 4.5 h, the hydrogen was vented and the catalyst was removed by filtration through celite®. Removal of solvent gave the title compound (0.09 g) as a pale yellow residue. This material was used without further purification. MS (ES) m/e 465.3 (M+H)$^+$.

c) Methyl (S)-3-oxo-8-[3-(pyrimidin-2-ylamino)-1-propyloxy]-2-[4-(trifluoromethyl)benzyl]-2,3,4,5-tetrahydro-1H-2-benzazepine-4-acetate A solution of methyl (S)-8-(3-amino-1-propyloxy)-3-oxo-2-[4-(trifluoromethyl)benzyl]-2,3,4,5-tetrahydro-1H-2-benzazepine-4-acetate (0.09 g, 0.19 mmol), 2-bromopyrimidine (0.09 g, 0.57 mmol) and diisopropylethylamine (0.17 mL, 0.98 mmol) in DMF (2 mL) was heated at 80° C. for 18 h. The reaction was allowed to cool to RT and was concentrated to give a yellow residue. Flash chromatography on silica gel (2% MeOH/EtOAc) gave the title compound (42 mg) as a clear oil. MS (ES) m/e 543.1 (M+H)$^+$.

d) Methyl (S)-3-oxo-8-[3-(3,4,5,6-tetrahydropyrimid-2-ylamino)-1-propyloxy]-2-[4-(trifluoromethyl)benzyl]-2,3,4,5-tetrahydro-1H-2-benzazepine-4-acetate A Parr hydrogenation apparatus was charged with methyl (S)-3-oxo-8-[3-(pyrimidin-2-ylamino)-1-propyloxy]-2-[4-(trifluoromethyl)benzyl]-2,3,4,5-tetrahydro-1H-2-benzazepine-4-acetate (42 mg, 0.08 mmol), glacial acetic acid (2 mL), concentrated HCl (0.2 mL), and 10% Pd/C (10 mg). The mixture was shaken under hydrogen (40 psi) for 5 h, then the hydrogen was vented and the catalyst was removed by filtration through celite®. Evaporation of the solvents gave the crude title compound (52 mg) as a dark residue. This was used without further purification. MS (ES) m/e 547.2 (M+H)$^+$.

e) (S)-3-Oxo-8-[3-(3,4,5,6-tetrahydropyrimid-2-ylamino)-1-propyloxy]-2-[4-(trifluoromethyl)benzyl]-2,3,4,5-tetrahydro-1H-2-benzazepine-4-acetic acid To the crude methyl (S)-3-oxo-8-[3-(3,4,5,6-tetrahydropyrimid-2-ylamino)-1-propyloxy]-2-[4-(trifluoro)benzyl]-2,3,4,5-tetrahydro-1H-2-benzazepine-4-acetate from Example 35d in EtOH (1 mL) was added 1 N NaOH (0.25 mL, 0.25 mmol). After stirring at RT for 8.5 h, the reaction was quenched by adding 1 N HCl (0.25 mL, 0.25 mmol). Removal of solvent gave a pale yellow solid. Preparative reverse phase HPLC (Hamilton PRP-1®, 30% CH$_3$CN/H$_2$O containing 0.1% TFA) gave the title compound (18.1 mg) as a white powder. MS (ES) m/e 533.3 (M+H)$^+$. Anal. Calcd for C$_{27}$H$_{31}$N$_4$F$_3$O$_4$.2 H$_2$O.2 CF$_3$CO$_2$H: C, 46.74; H, 4.68; N, 7.03. Found: C, 46.34; H, 4.31; N, 6.82.

Example 36

Preparation of (±)-3-oxo-8-[3-(N-(pyridin-2-yl)-N-(methyl)amino)-1-propyloxy]-2-[4-(trifluoromethyl)benzyl]-2,3,4,5-tetrahydro-1H-2-benzazepine-4-acetic acid a) Methyl(±)-3-oxo-8-[3-[N-(1-oxopyridin-2-yl)-N-(methyl)amino)]-1-propyloxy]-2-[4-(trifluoromethyl)benzyl]-2,3,4,5-tetrahydro-1H-2-benzazepine-4-acetic acid According to the procedure of Example 25(a), except substituting methyl(±)-3-oxo-8-[3-[N-(1-oxopyridin-2-yl)-N-(tert-butoxycarbonyl)amino]-1-propyloxy]-2-(4-trifluoromethylbenzyl)-2,3,4,5-tetrahydro-1H-2-benzazepine-4-acetate for the (±)-3-oxo-8-[3-[N-(pyridin-2-yl)-N-(tert-butoxycarbonyl)amino]-1-propyloxy]-2-(4-trifluoromethylbenzyl)-2,3,4,5-tetrahydro-1H-2-benzazepine-4-acetic acid, the HCl salt was prepared. This material was converted to the free base by partitioning between EtOAc and 5% NaHCO$_3$. The EtOAc layer was separated and concentrated to give the title compound (4.1 g, 100%): MS (ES) m/e 558.3 (M+H)$^+$.

b) Methyl(±)-3-oxo-8-[3-(N-(1-oxopyridin-2-yl)-N-methylamino)-1-propyloxy]-2-(4-trifluoromethylbenzyl)-2,3,4,5-tetrahydro-1H-2-benzazepine-4-acetate According to the procedure of Example 26(a), except substituting methyl(±)-3-oxo-8-[3-[N-(1-oxopyridin-2-yl)-N-(methyl)amino)]-1-propyloxy]-2-[4-(trifluoromethyl)benzyl]-2,3,4,5-tetrahydro-1H-2-benzazepine-4-acetic acid for the methyl (±)-8-[3-[2-(N-oxopyridyl)amino]-1-propyloxy]-3-oxo-2,3,4,5-tetrahydro-1H-2-benzazepine-4-acetate, the title compound (3.0 g, 94%) was prepared: MS (ES) m/e 572.3 (M+H)$^+$.

c) Methyl(±)-3-oxo-8-[3-(N-(pyridin-2-yl)-N-(methyl)amino)-1-propyloxy]-2-(4-trifluoromethylbenzyl)-2,3,4,5-tetrahydro-1H-2-benzazepine-4-acetate According to the procedure of Example 4(b), except substituting methyl(±)-3-oxo-8-[3-(N-(1-oxopyridin-2-yl)-N-(methyl)amino)-1-propyloxy]-2-(4-trifluoromethylbenzyl)-2,3,4,5-tetrahydro-1H-2-benzazepine-4-acetate for the methyl (±)-8-[3-[2-(N- oxopyridyl)amino]-1-propyloxy]-2-methyl-3-oxo-2,3,4,5-tetrahydro-1H-2-benzazepine-4-acetate, the title compound (0.32 g, 60%) was prepared: MS (ES) m/e 556.2 (M+H)⁺.

d) (±)-3-Oxo-8-[3-(N-(pyridin-2-yl)-N-(methyl)amino)-1-propyloxy]-2-[4-(trifluoromethyl)benzyl]-2,3,4,5-tetrahydro-1H-2-benzazepine-4-acetic acid According to the procedure of Example 4 (c), except substituting methyl(±)-3-oxo-8-[3-(N-(pyridin-2-yl)-N-(methyl)amino)-1-propyloxy]-2-(4-trifluoromethylbenzyl)-2,3,4,5-tetrahydro-1H-2-benzazepine-4-acetate for the methyl(±)-8-[3-(2-pyridylamino)-1-propyloxy]-2-methyl-3-oxo-2,3,4,5-tetrahydro-1H-2-benzazepine-4-acetate, the title compound (0.02 g, 15%) was prepared: MS (ES) m/e 542.1 (M+H)⁺. Anal. Calcd for $C_{29}H_{30}N_3O_4F_3 \cdot CF_3CO_2H \cdot H_2O$: C, 55.28; H, 4.94; N, 6.24. Found: C, 55.45; H, 4.68; N, 6.14.

Example 37

Preparation of (S)-3-oxo-8-[3-(pyridin-2-ylamino)-1-propyloxy]-2-(2,2,2-trifluoroethyl)-2,3,4,5-tetrahydro-1H-2-benzazepine-4-acetic acid a) Methyl (S)-3-oxo-8-[3-(1-oxopyridin-2-ylamino)-1-propyloxy]-2-(2,2,2-trifluoroethyl)-2,3,4,5-tetrahydro-1H-2-benzazepine-4-acetate To a stirred solution of methyl (S)-8-hydroxy-2-methyl-3-oxo-2,3,4,5-tetrahydro-1H-2-benzazepine-4-acetate (19 g, 57.4 mmol) in dry THF (400 mL) and dry DMF (200 mL) under argon were added 2-(3-hydroxypropylamino)pyridine N-oxide (11.6 g, 69 mmol) and triphenylphosphine (18.0 g, 69 mmol). After all solids had completely dissolved (~30 minutes), the reaction was cooled to 0° C. in an ice bath and diisopropyl azodicarboxylate (14.3 mL, 69 mmol) was added via syringe. The reaction was allowed to warm slowly to RT and was stirred for 18 h. Concentration and flash chromatography on silica gel (8:2:1 CHCl₃/EtOAc/EtOH) gave the title compound (20.83 g, 75%) as a solid foam. An additional 5.73 g of product can be obtained by recycling of the recovered starting material from the above reaction to give a total of 26.56 g (96%) of the title compound: MS (ES) m/e 482.2 (M+H)⁺; ¹H NMR (400 MHz, DMSO-d₆) δ 8.09 (dd, J=6.5, 1.3 Hz, 1H), 7.29 (t, 1H), 7.18 (t, 1H), 7.02 (d, J=9.2 Hz, 1H), 6.84–6.79 (m, 3H), 6.59 (t, 1H), 5.32 (d, J=16.5 Hz, 1H), 4.28–4.14 (m, 2H), 4.16 (d, J=16.5 Hz, 1H), 4.02 (t, 2H), 3.84 (m, 1H), 3.58 (s, 3H), 3.40 (dd, 2H), 3.01 (dd, 1H), 2.73 (dd, 1H), 2.70 (dd, 1H), 2.52 (dd, 1H), 2.02 (ddd, 2H).

b) Methyl (S)-3-oxo-8-[3-(pyridin-2-ylamino)-1-propyloxy]-2-(2,2,2-trifluoroethyl)-2,3,4,5-tetrahydro-1H-2-benzazepine-4-acetate To a stirred solution of methyl (S)-3-oxo-8-[3-(1-oxopyridin-2-ylamino)-1-propyloxy]-2-(2,2,2-trifluoroethyl)-2,3,4,5-tetrahydro-1H-2-benzazepine-4-acetate (26.56 g, 55 mmol) in isopropanol (500 mL) were added 10% palladium on activated carbon (8 g, 7.5 mmol, carefully pre-wetted in isopropanol under Argon) and cyclohexene (55.7 mL, 550 mmol). The reaction was then heated to reflux under Argon in an oil bath set at 90° C. After 6 h an additional amount of 10% palladium on activated carbon (8 g, 7.5 mmol, carefully pre-wetted in isopropanol under Argon) and cyclohexene (55.7 mL, 550 mmol) were added. After an additional 18 h the reaction was hot-filtered through celite®, and the filter pad was washed with 1:1 MeOH/CHCl₃ (400 mL). The filtrate was concentrated under vacuum and the residue was purified by flash chromatography on silica gel (95:5 CHCl₃/MeOH) to give the title compound (19.50 g, 76%) as a white sticky foam: TLC (silica, 5% MeOH in CHCl₃) R_f 0.52; MS (ES) m/e 466.3 (M+H)⁺; ¹H NMR (400 MHz, DMSO-d₆) δ 7.94 (dd, 1H), 7.34 (t, 1H), 7.02 (d, J=9.2 Hz, 1H), 6.81 (m, 2H), 6.54 (t, 1H), 6.46 (m, 2H), 5.31 (d, J=16.5 Hz, 1H), 4.23–4.13 (m, 2H), 4.17 (d, J=16.5 Hz, 1H), 4.02 (t, 2H), 3.82 (m, 1H), 3.58 (s, 3H), 3.36 (m, 2H), 3.01 (dd, 1H), 2.72 (dd, 1H), 2.68 (dd, 1H), 2.50 (dd, 1H), 1.96 (ddd, 2H).

c) (S)-3-Oxo-8-[3-(pyridin-2-ylamino)-1-propyloxy]-2-(2,2,2-trifluoroethyl)-2,3,4,5-tetrahydro-1H-2-benzazepine-4-acetic acid To a stirred solution of methyl (S)-3-oxo-8-[3-(pyridin-2-ylamino)-1-propyloxy]-2-(2,2,2-trifluoroethyl)-2,3,4,5-tetrahydro-1H-2-benzazepine-4-acetate (19.50 g, 42 mmol) in dioxane (150 mL) was added aqueous 1 N NaOH (75 mL, 75 mmol). The cloudy reaction was stirred at RT for 2 h, then the resulting homogeneous solution was neutralized with aqueous 1 N HCl (75 mL, 75 mmol). The solution was concentrated to near dryness by rotary evaporation to precipitate out the product. The supernatant was decanted off and the remaining gummy solid was redissolved in methanol. The clear solution was then reconcentrated by rotary evaporation. The remaining solid was triturated with a small volume of water, filtered and dried under vacuum to give the title compound (16.38 g, 86%) as a white powder. HPLC (Hamilton PRP-1®, 25% CH₃CN/H₂O containing 0.1% TFA) k'=3.1; [α]_D –112.3° (c, 1.0, MeOH); MS (ES) m/e 452.3 (M+H)⁺; ¹H NMR (400 MHz, DMSO-d₆) δ 7.95 (dd, 1H), 7.34 (dt, 1H), 7.02 (d, J=9.2 Hz, 1H), 6.81 (m, 2H), 6.58 (t, 1H), 6.47 (m, 2H), 5.30 (d, J=16.5 Hz, 1H), 4.27–4.13 (m, 2H), 4.15 (d, J=16.5 Hz, 1H), 4.02 (t, 1H), 3.78 (m, 1H), 3.37 (m, 2H), 3.00 (dd, 1 H), 2.69 (dd, 1H), 2.65 (dd, 1H), 2.41 (dd, 1H), 1.96 (ddd, 2 H). Anal. Calcd for $C_{22}H_{24}F_3N_3O_4$: C, 58.53; H, 5.36; N, 9.31. Found: C, 58.37; H, 5.42; N, 9.20.

Example 38

Preparation of (R)-3-oxo-8-[3-(pyridin-2-ylamino)-1-propyloxy]-2-(2,2,2-trifluoroethyl)-2,3,4,5-tetrahydro-1H-2-benzazepine-4-acetic acid a) Methyl (R)-3-oxo-8-[3-(1-oxopyridin-2-ylamino)-1-propyloxy]-2-(2,2,2-trifluoroethyl)-2,3,4,5,-tetrahydro-1H-2-benzazepine-4-acetate A solution of 2-[(3-hydroxy-1-propyl)amino]pyridine-N-oxide (0.33 g, 2 mmole) and diethyl azodicarboxylate (0.3 mL, 2 mmole) in anhydrous DMF (10 mL) was added slowly dropwise to a solution of methyl (R)-8-hydroxy-3-oxo-2-(2,2,2-trifluoroethyl)-2,3,4,5-tetrahydro-1H-2-benzazepine-4-acetate (0.3 g, 1 mmole) and triphenylphosphine (0.485 g, 26 mmole) in anhydrous CH₂Cl₂ (10 mL) at RT. After 17 hr, the reaction was concentrated. Silica gel chromatography (gradient: 0.5%–5% MeOH/CH₂Cl₂) gave the title compound (0.35 g, 80%) as a colorless oil: MS (ES) m/e 482.3 (M+H)⁺.

b) Methyl (R)-3-oxo-8-[3-(pyridin-2-ylamino)-1-propyloxy]-2-(2,2,2-trifluoroethyl)-2,3,4,5-tetrahydro-1H-2-benzazepine-4-acetate A mixture of methyl (R)-3-oxo-8-[3-(1-oxopyridin-2-ylamino)-1-propyloxy]-2-(2,2,2-trifluoroethyl)-2,3,4,5-tetrahydro-1H-2-benzazepine-4-acetate (0.35 g, 0.7 mmole), cyclohexene (0.75 mL, 7 mmole), 10% Pd/C (88 mg, 0.07 mmole), and isopropanol (9 mL) was heated to reflux under argon. After 18 hr, additional 10% Pd/C (36 mg, 0.03 mmole) and cyclohexene (0.75 mL, 7 mmole) were added. After 36 hr, the reaction was hot-filtered through celite®, and the filter pad was washed with hot EtOAc. Concentration left a yellow oil. Silica gel chromatography (1%–5% MeOH in CH₂Cl₂) gave the title compound (0.26 g, 77%) as a colorless oil: MS (ES) m/e 466.2 (M+H)⁺.

c) (R)-3-Oxo-8-[3-(pyridin-2-ylamino)-1-propyloxy]-2-(2,2,2-trifluoroethyl)-2,3,4,5-tetrahydro-1H-2-benzazepine-4-acetic acid LiOH.H₂O (25 mg, 0.6 mmole) was added to a solution of methyl (R)-8-[3-(2-pyridylamino)-1-propyloxy]-3-oxo-2-(2,2,2-trifluoroethyl)-2,3,4,5-tetrahydro-1H-2-benzazepine-4-acetate (0.25 g, 0.54 mmole) in THF (5 mL) and H₂O (2 mL) at RT. After 18 hr, the reaction was concentrated to dryness and the residue was dissolved in H₂O (4 mL). The solution was carefully brought to pH≈4 with 3.0 N HCl. The precipitate was collected and dried in high vacuum at 40–45° C. to afford the title compound (0.15 g, 62%) as an off-white solid: MS (ES) m/e 452.1 (M+H)⁺. Anal. Calcd for $C_{22}H_{24}F_3N_3O_4$. 0.5 H₂O: C, 57.38; H, 5.47; N, 9.12. Found: C, 57.72; H, 5.24; N, 8.92.

Example 39

Preparation of (S)-8-[3-(4-methylpyridin-2-ylamino)-1-propyloxy]-3-oxo-2-(2,2,2-trifluoroethyl)-2,3,4,5-1H-2-benzazepine-4-acetic acid a) Methyl (S)-8-[3-(4-methyl-1-oxopyridin-2-ylamino)-1-propyloxy]-3-oxo-2-(2,2,2-trifluoroethyl)-2,3,4,5-tetrahydro-1H-2-benzazepine-4-acetate A solution of 2-[(3-hydroxy-1-propyl)amino]-4-methylpyridine-N-oxide (0.60 g, 3.6 mmole) and diethyl azodicarboxylate (0.6 mL, 3.6 mmole) in anhydrous CH₂Cl₂ (12 mL) was added dropwise over 3–4 min to a solution of methyl (S)-8-hydroxy-3-oxo-2-(2,2,2-trifluoroethyl)-2,3,4,5-tetrahydro-1H-2-benzazepine-4-acetate (0.60 g, 1.8 mmole) and triphenylphosphine (0.95 g, 3.6 mmole) in anhydrous CH₂Cl₂ (6 mL) at RT. After 17 hr, the reaction was concentrated. Silica gel chromatography (gradient: 1%–5% MeOH/CH₂Cl₂) gave the title compound (0.45 g, 49%) as an off-white foam: MS (ES) m/e 496.3 (M+H)⁺.

b) Methyl(S)-8-[3-(4-methylpyridin-2-ylamino)-1-propyloxy]-3-oxo-2-(2,2,2-trifluoroethyl)-2,3,4,5-tetrahydro-1H-2-benzazepine-4-acetate A mixture of methyl (S)-8-[3-(4-methyl-1-oxopyridin-2-ylamino)-1-propyloxy]-3-oxo-2-(2,2,2-trifluoroethyl)-2,3,4,5-tetrahydro-1H-2-benzazepine-4-acetate (0.45 g, 0.9 mmole), cyclohexene (0.93 mL, 9 mmole), 10% Pd/C (0.2 g, 0.18 mmole), and isopropanol (9 mL) was heated to reflux under argon. After 18 hr, additional 10% Pd/C (0.2 g, 0.18 mmole) and cyclohexene (0.27 mL, 2.65 mmole) were added. After 36 hr, the reaction was hot-filtered through celite®, and the filter pad was washed with hot EtOAc. Concentration left a yellow oil. Silica gel chromatography (1%–3% MeOH in CH₂Cl₂) gave the title compound (0.32 g, 74%) as a white foam: MS (ES) m/e 480.2 (M+H)⁺.

c) (S)-8-[3-(4-Methylpyridin-2-ylamino)-1-propyloxy]-3-oxo-2-(2,2,2-trifluoroethyl)-2,3,4,5-tetrahydro-1H-2-benzazepine-4-acetic acid LiOH.H₂O (33 mg, 0.79 mmole) was added to a solution of methyl (S)-8-[3-(4-methylpyridin-2-ylamino-1-propyloxy]-3-oxo-2-(2,2,2-trifluoroethyl)-2,3,4,5-tetrahydro-1H-2-benzazepine-4-acetate (0.32 g, 0.67 mmole) in THF (5 mL) and H₂O (2 mL) at RT. After 18 hr, the reaction was concentrated to dryness and the residue was dissolved in H₂O (4 mL). The solution was extracted with ethyl acetate, then was carefully brought to pH≈5 with 3.0 N HCl. The precipitate was collected and dried in high vacuum at 40–45° C. to afford the title compound (0.22 g, 71%) as an off-white solid: MS (ES) m/e 466.1 (M+H)⁺. Anal. Calcd for $C_{23}H_{26}F_3N_3O_4$: C, 59.35; H, 5.63; N, 9.03. Found: C, 58.97; H, 5.55; N, 8.73.

Example 40

Preparation of (S)-8-[2-[6-(methylamino)pyridin-2-yl]-1-ethoxy]-3-oxo-2-(2,2,2-trifluoroethyl)-2,3,4,5-tetrahydro-1H-2-benzazepine-4-acetic acid a) Methyl (S)-8-[2-[6-(methylamino)pyridin-2-yl]-1-ethoxy]-3-oxo-2-(2,2,2-trifluoroethyl)-2,3,4,5-tetrahydro-1H-2-benzazepine-4-acetate According to the method of Example 37(a), except substituting 6-(methylamino)-2-pyridylethanol for the 2-[(3-hydroxy-1H-propyl)amino]pyridine-N-oxide, and substituting (S)-8-hydroxy-3-oxo-2-(2,2,2-trifluoroethyl)-2,3,4,5-tetrahydro-1H-2-benzazepine-4-acetate for the (R)-8-hydroxy-3-oxo-2-(2,2,2-trifluoroethyl)-2,3,4,5-tetrahydro-1H-2-benzazepine-4-acetate, the title compound was prepared as a colorless oil: MS (ES) m/e 466.2 (M+H)⁺.

b) (S)-8-[2-[6-(Methylamino)pyridin-2-yl]-1-ethoxy]-3-oxo-2-(2,2,2-trifluoroethyl)-2,3,4,5-tetrahydro-1H-2-benzazepine-4-acetic acid According to the method of Example 37(c), except substituting methyl (S)-8-[2-[6-(methylamino)pyridin-2-yl]-1-ethoxy]-3-oxo-2-(2,2,2-trifluoroethyl)-2,3,4,5-tetrahydro-1H-2-benzazepine-4-acetate for the methyl (R)-8-[3-(2-pyridylamino)-1-propyloxy]-3-oxo-2-(2,2,2-trifluoroethyl)-2,3,4,5-tetrahydro-1H-2-benzazepine-4-acetate, the title compound was prepared as a white solid: MS (ES) m/e 452.2 (M+H)⁺. Anal. Calcd for $C_{22}H_{24}F_3N_3O_4$.0.7 H₂O: C, 56.94; H, 5.52; N, 9.05. Found: C, 56.80; H, 5.19; N, 8.85.

Example 41

Preparation of (S)-3-oxo-8-[3-(pyridin-2-ylamino)-1-propyloxy]-2-(2-phenylethyl)-2,3,4,5-tetrahydro-1H-2-benzazepine-4-acetic acid a) Methyl (S)-3-oxo-8-[3-(1-oxopyridin-2-ylamino)-1-propyloxy]-2-(2-phenylethyl)-2,3,4,5-tetrahydro-1H-2-benzazepine-4-acetate A solution of 2-[(3-hydroxy-1-propyl)amino]pyridine-N-oxide (336 mg, 2.0 mmole) and diethyl azodicarboxylate (0.3 mL, 2.0 mmole) in anhydrous DMF (10 mL) was added to a solution of methyl (S)-8-hydroxy-3-oxo-2-(2-phenylethyl)-2,3,4,5-tetrahydro-1H-2-benzazepine-4-acetate (350 mg, 1.0 mmole) and triphenylphosphine (525 mg, 2.0 mmole) in anhydrous DMF (10 mL) at RT. After 24 hr the mixture was concentrated. Flash silica gel chromatography (gradient: EtOAc (500 mL) then 5% MeOH/CHCl₃) gave the title compound as an orange foam (288 mg, 57%): MS (ES) m/e 504 (M+H)⁺.

b) Methyl (S)-3-oxo-8-[3-(pyridin-2-ylamino)-1-propyloxy]-2-(2-phenylethyl)-2,3,4,5-tetrahydro-1H-2-benzazepine-4-acetate A mixture of methyl (S)-3-oxo-8-[3-(1-oxopyridin-2-ylamino)-1-propyloxy]-2-(2-phenylethyl)-2,3,4,5-tetrahydro-1H-2-benzazepine-4-acetate (288 mg, 0.57 mmole), cyclohexene (0.6 mL, 5.8 mmole), 10% Pd/C (62 mg, 0.58 mmole), and 2-propanol (6 mL) was heated to reflux under argon. After 31 hr the mixture was hot filtered through a pad of celite®, the filter pad was washed with hot 1:1 MeOH/CHCl₃ (200 mL), and the filtrate was concentrated. Flash silica gel chromatography (5% MeOH/CHCl₃) followed by a second flash silica gel chromatography (50% THF/cyclohexane) gave the title compound as an off-white foam (133 mg, 48%): MS (ES) m/e 488 (M+H)⁺.

c) (S)-3-Oxo-8-[3-(pyridin-2-ylamino)-1-propyloxy]-2-(2-phenylethyl)-2,3,4,5-tetrahydro-1H-2-benzazepine-4-acetic acid 1.0 N LiOH (0.3 mL, 0.3 mmole) was added to a solution of methyl (S)-3-oxo-8-[3-(pyridin-2-ylamino)-1-propyloxy]-2-(2-phenylethyl)-2,3,4,5-tetrahydro-1H-2-benzazepine-4-acetate (133 mg, 0.27 mmole) in THF (1.5 mL) and H₂O (1.2 mL) at 0° C. The mixture was allowed to warm to RT over 18 hr. The mixture was washed with Et₂O (2×5 mL) then a mild vacuum was applied to remove residual organic solvents. The aqueous layer was passed through a 0.45 μm Acrodisk filter, then was carefully acidified to pH 6 using 10% HCl in H₂O at 0° C. The precipitate was collected, washed with H₂O, and dried under vacuum at 50° C. to give the title compound as a white solid (62 mg, 48%): MS (ES) m/e 474 (M+H)⁺. Anal. Calcd for $C_{28}H_{31}N_3O_4 \cdot 0.75 H_2O$: C, 69.05; H, 6.75; N, 8.63. Found: C, 69.05; H, 6.66; N, 8.55.

Example 42
Preparation of (S)-8-[2-[6-(methylamino)pyridin-2-yl]ethoxy]-3-oxo-2-(2-phenylethyl)-2,3,4,5-tetrahydro-1H-2-benzazepine-4-acetic acid a) Methyl (S)-8-[2-[6-(methylamino)pyridin-2-yl]ethoxy]-3-oxo-2-(2-phenylethyl)-2,3,4,5-tetrahydro-1H-2-benzazepine-4-acetate Diisopropyl azodicarboxylate (0.3 mL, 1.5 mmole) was added to a solution of (S)-8-hydroxy-3-oxo-2-(2-phenylethyl)-2,3,4,5-tetrahydro-1H-2-benzazepine-4-acetate (350 mg, 1.0 mmole), 6-(methylamino)-2-pyridylethanol (228 mg, 1.5 mmole), and triphenylphosphine (393 mg, 1.5 mmole) in anhydrous THF (10 mL) at 0° C. The mixture was allowed to warm to RT over 72 hr then was concentrated. Flash silica gel chromatography (50% EtOAc/hexanes) followed by a second flash silica gel chromatography (25% EtOAc/hexanes) gave the title compound as a white foam (250 mg, 51%): MS (ES) m/e 488 (M+H)⁺.

b) (S)-8-[2-[6-(Methylamino)pyridin-2-yl]ethoxy]-3-oxo-2-(2-phenylethyl)-2,3,4,5-tetrahydro-1H-2-benzazepine-4-acetic acid 1.0N LiOH (0.62 mL, 0.62 mmole) was added to a solution of methyl (S)-8-[2-[6-(methylamino)pyridin-2-yl]ethoxy]-3-oxo-2-(2-phenylethyl)-2,3,4,5-tetrahydro-1H-2-benzazepine-4-acetate (250 mg, 0.51 mmole) in THF (2.5 mL) and $H_2O$ (1.9 mL) at 0°0 C., and the reaction was allowed to stir at RT for 18 hr. The mixture was washed with $Et_2O$ (2×5 mL) then a mild vacuum was applied to remove residual organic solvents. The aqueous layer was passed through a 0.45 μm Acrodisk filter then was carefully acidified to pH 6 using 10% HCl in $H_2O$ at 0° C. The precipitate was collected, washed with $H_2O$, and dried under vacuum at 50° C. to give the title compound (134 mg, 55%) as a white solid: MS (ES) m/e 474 (M+H)⁺. Anal. Calcd for $C_{28}H_{31}N_3O_4 \cdot 0.75 H_2O$: C, 69.05; H, 6.73; N, 8.63. Found: C, 69.23; H, 6.59; N, 8.55.

Example 43
Preparation of (S)-8-[2-[6-(methylamino)pyridin-2-yl]-1-ethoxy]-3-oxo-2-[4-(trifluoromethyl)benzyl]-2,3,4,5-tetrahydro-1H-2-benzazepine-4-acetic acid a) Methyl (S)-8-[2-[6-(methylamino)pyridin-2-yl]-1-ethoxy]-3-oxo-2-[4-(trifluoromethyl)benzyl]-2,3,4,5-tetrahydro-1H-2-benzazepine-4-acetate To a solution of methyl (S)-8-hydroxy-3-oxo-2-[4-(trifluoromethyl)benzyl]-2,3,4,5-tetrahydro-1H-2-benzazepine-4-acetate (0.18 g, 0.44 mmol) and $Ph_3P$ (0.23 g, 0.88 mmol) in $CH_2Cl_2$ (2 mL) was added a solution of 6-(methylamino)-2-pyridylethanol (0.13 g, 0.88 mmol) and diethylazodicarboxylate (0.14 mL, 0.89 mmol) in $CH_2Cl_2$ (2 mL). After 2 days at RT, the solvent was removed under reduced pressure. Radial chromatography on silica gel (6 mm plate, 5% MeOH/CHCl₃) gave a clear oil (0.63 g) which contained a mixture of the title compound together with unreacted methyl (S)-8-hydroxy-3-oxo-2-[4-(trifluoromethyl)benzyl]-2,3,4,5-tetrahydro-1H-2-benzazepine-4-acetate. This material was further purified by radial chromatography on silica gel (6 mm plate, 50% EtOAc/hexanes) to give the title compound (0.12 g) as a clear oil: MS (ES) m/e 542.3 (M+H)⁺.

b) (S)-8-[2-[6-(Methylamino)pyridin-2-yl]-1-ethoxy]-3-oxo-2-[4-(trifluoromethyl)benzyl]-2,3,4,5-tetrahydro-1H-2-benzazepine-4-acetic acid To a solution of methyl (S)-8-[2-[6-(methylamino)pyridin-2-yl]-1H-ethoxy]-3-oxo-2-[4-(trifluoromethyl)benzyl]-2,3,4,5-tetrahydro-1H-2-benzazepine-4-acetate (0.12 g, 0.22 mmol) in EtOH (2 mL) was added 1 N NaOH (0.50 mL). After 3.5 h at RT, the bulk of the solvent was removed under reduced pressure to give a white residue. This was dissolved in water and the solution was neutralized to pH=7 with 1 N HCl. The resulting precipitate was collected and dried under vacuum to give the title compound (28.1 mg) as a white solid: $[\alpha]_D$ −74.0° (c 0.05, EtOH); MS (ES) m/e 528.3 (M+H)⁺. Anal. Calcd for $C_{28}H_{28}F_3N_3O_4 \cdot 0.5 H_2O$: C, 62.68; H, 5.45; N, 7.83. Found: C, 62.60; H, 5.35; N, 7.66.

Example 44
Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 45
Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 46
Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A compound which is (S)-3-oxo-8-[3-(pyridin-2-ylamino)-1-propyloxy]-2-(2,2,2-trifluoroethyl)-2,3,4,5-tetrahydro-1H-2-benzazepine-4-acetic acid or (S)-8-[2-[6-(methylamino)pyridin-2-yl]-1-ethoxy]-3-oxo-2-(2,2,2-trifluoroethyl)-2,3,4,5-tetrahydro-1H-2-benzazepine-4-acetic acid; or a pharmaceutically acceptable salt thereof.

2. A pharmaceutical composition which comprises a compound according to claim 1 and a pharmaceutically acceptable carrier.

3. A method of treating osteoporosis which comprises administering to a subject in need thereof a compound according to claim 1.

* * * * *